US008121694B2

(12) United States Patent
Molnar et al.

(10) Patent No.: US 8,121,694 B2
(45) Date of Patent: Feb. 21, 2012

(54) THERAPY CONTROL BASED ON A PATIENT MOVEMENT STATE

(75) Inventors: Gregory F. Molnar, Fridley, MN (US); Steven S. Gill, Bristol (GB); Keith A. Miesel, St. Paul, MN (US); Mark S. Lent, Brooklyn Park, MN (US); Timothy J. Denison, Minneapolis, MN (US); Eric J. Panken, Edina, MN (US); Carl D. Wahlstrand, Lino Lakes, MN (US); Jonathan C. Werder, Corcoran, MN (US)

(73) Assignee: Medtronic, Inc., Minneapolis, MN (US)

( * ) Notice: Subject to any disclaimer, the term of this patent is extended or adjusted under 35 U.S.C. 154(b) by 568 days.

(21) Appl. No.: 12/237,799

(22) Filed: Sep. 25, 2008

(65) Prior Publication Data
US 2009/0099627 A1   Apr. 16, 2009

Related U.S. Application Data

(60) Provisional application No. 60/999,096, filed on Oct. 16, 2007, provisional application No. 60/999,097, filed on Oct. 16, 2007.

(51) Int. Cl.
*A61N 1/18* (2006.01)
(52) U.S. Cl. .......................................................... 607/45
(58) Field of Classification Search ...................... 607/45
See application file for complete search history.

(56) References Cited

U.S. PATENT DOCUMENTS

| | | | |
|---|---|---|---|
| 3,780,725 A | 12/1973 | Goldberg | |
| 4,013,068 A | 3/1977 | Settle et al. | |
| 4,776,345 A | 10/1988 | Cohen et al. | |
| 5,335,657 A | 8/1994 | Terry, Jr. et al. | |
| 5,489,759 A | 2/1996 | Litt et al. | |
| 5,769,877 A | 6/1998 | Barreras, Sr. | |
| 5,833,709 A | 11/1998 | Rise et al. | |

(Continued)

FOREIGN PATENT DOCUMENTS
DE   19649991 A1   6/1998
(Continued)

OTHER PUBLICATIONS

Avestruz et al., "A 5 µW/Channel Spectral Analysis IC for Chronic Bidirectional Brain-Machine Interfaces," IEEE Journal of Solid-State Circuits, vol. 43, No. 12, Dec. 2008, 19 pages.

(Continued)

*Primary Examiner* — Carl H Layno
*Assistant Examiner* — Paula J Stice
(74) *Attorney, Agent, or Firm* — Shumaker & Sieffert, P.A.

(57) ABSTRACT

A movement state of a patient is detected based on brain signals, such as an electroencephalogram (EEG) signal. In some examples, a brain signal within a dorsal-lateral prefrontal cortex of a brain of the patient indicative of prospective movement of the patient may be sensed in order to detect the movement state. The movement state may include the brain state that indicates the patient is intending on initiating movement, initiating movement, attempting to initiate movement or is actually moving. In some examples, upon detecting the movement state, a movement disorder therapy is delivered to the patient. In some examples, the therapy delivery is deactivated upon detecting the patient is no longer in a movement state or that the patient has successfully initiated movement. In addition, in some examples, the movement state detected based on the brain signals may be confirmed based on a signal from a motion sensor.

34 Claims, 28 Drawing Sheets

U.S. PATENT DOCUMENTS

| | | | |
|---|---|---|---|
| 5,840,040 A * | 11/1998 | Altschuler et al. | 600/545 |
| 5,995,868 A | 11/1999 | Dorfmeister et al. | |
| 6,024,700 A | 2/2000 | Nemirovski et al. | |
| 6,066,163 A | 5/2000 | John | |
| 6,094,598 A | 7/2000 | Elsberry et al. | |
| 6,157,857 A | 12/2000 | Dimpfel | |
| 6,315,740 B1 | 11/2001 | Singh | |
| 6,356,784 B1 | 3/2002 | Lozano et al. | |
| 6,366,813 B1 | 4/2002 | DiLorenzo | |
| 6,459,936 B2 | 10/2002 | Fischell et al. | |
| 6,463,328 B1 | 10/2002 | John | |
| 6,468,234 B1 | 10/2002 | Van der Loos et al. | |
| 6,605,038 B1 | 8/2003 | Teller et al. | |
| 6,658,287 B1 | 12/2003 | Litt et al. | |
| 6,954,524 B2 | 10/2005 | Gibson et al. | |
| 7,110,820 B2 | 9/2006 | Tcheng et al. | |
| 7,120,486 B2 | 10/2006 | Leuthardt et al. | |
| 7,151,961 B1 | 12/2006 | Whitehurst et al. | |
| 7,209,788 B2 | 4/2007 | Nicolelis et al. | |
| 7,299,088 B1 | 11/2007 | Thakor et al. | |
| 2002/0002390 A1 * | 1/2002 | Fischell et al. | 607/45 |
| 2002/0103512 A1 | 8/2002 | Echauz et al. | |
| 2002/0177882 A1 * | 11/2002 | DiLorenzo | 607/45 |
| 2003/0046254 A1 | 3/2003 | Ryu et al. | |
| 2003/0105409 A1 | 6/2003 | Donoghue et al. | |
| 2003/0149457 A1 | 8/2003 | Tcheng et al. | |
| 2003/0158587 A1 | 8/2003 | Esteller et al. | |
| 2003/0171791 A1 | 9/2003 | KenKnight et al. | |
| 2004/0015211 A1 | 1/2004 | Nurmikko et al. | |
| 2004/0082875 A1 | 4/2004 | Donoghue et al. | |
| 2004/0122483 A1 | 6/2004 | Nathan et al. | |
| 2004/0176809 A1 | 9/2004 | Cho et al. | |
| 2004/0215286 A1 | 10/2004 | Stypulkowski | |
| 2004/0249302 A1 | 12/2004 | Donoghue et al. | |
| 2004/0249422 A1 | 12/2004 | Gliner et al. | |
| 2005/0007091 A1 | 1/2005 | Makeig et al. | |
| 2005/0043652 A1 | 2/2005 | Lovett et al. | |
| 2005/0081847 A1 | 4/2005 | Lee et al. | |
| 2005/0113744 A1 | 5/2005 | Donoghue et al. | |
| 2005/0143635 A1 | 6/2005 | Donoghue et al. | |
| 2005/0197588 A1 | 9/2005 | Freeberg | |
| 2005/0203366 A1 | 9/2005 | Donoghue et al. | |
| 2005/0209511 A1 | 9/2005 | Heruth et al. | |
| 2005/0209512 A1 | 9/2005 | Heruth et al. | |
| 2005/0209644 A1 | 9/2005 | Heruth et al. | |
| 2006/0049957 A1 | 3/2006 | Surgenor et al. | |
| 2006/0058627 A1 | 3/2006 | Flaherty et al. | |
| 2006/0135879 A1 | 6/2006 | Liley | |
| 2006/0149338 A1 | 7/2006 | Flaherty et al. | |
| 2006/0167530 A1 | 7/2006 | Flaherty et al. | |
| 2006/0169282 A1 | 8/2006 | Izumi et al. | |
| 2006/0173259 A1 | 8/2006 | Flaherty et al. | |
| 2006/0173494 A1 | 8/2006 | Armstrong et al. | |
| 2006/0189899 A1 | 8/2006 | Flaherty et al. | |
| 2006/0206167 A1 | 9/2006 | Flaherty et al. | |
| 2006/0206174 A1 | 9/2006 | Honeycutt et al. | |
| 2006/0212090 A1 | 9/2006 | Lozano et al. | |
| 2006/0212093 A1 | 9/2006 | Pless et al. | |
| 2006/0253166 A1 | 11/2006 | Flaherty et al. | |
| 2006/0253168 A1 | 11/2006 | Wyler et al. | |
| 2006/0258930 A1 | 11/2006 | Wu et al. | |
| 2006/0259099 A1 | 11/2006 | Goetz et al. | |
| 2006/0293604 A1 | 12/2006 | Carlson et al. | |
| 2007/0016095 A1 | 1/2007 | Low et al. | |
| 2007/0032738 A1 | 2/2007 | Flaherty et al. | |
| 2007/0032834 A1 | 2/2007 | Gliner et al. | |
| 2007/0038265 A1 | 2/2007 | Tcheng et al. | |
| 2007/0046486 A1 | 3/2007 | Donoghue et al. | |
| 2007/0073355 A1 | 3/2007 | DiLorenzo | |
| 2007/0123758 A1 | 5/2007 | Miesel et al. | |
| 2007/0150025 A1 | 6/2007 | Dilorenzo et al. | |
| 2007/0213785 A1 | 9/2007 | Osorio et al. | |
| 2008/0154111 A1 | 6/2008 | Wu et al. | |
| 2008/0269812 A1 | 10/2008 | Gerber et al. | |
| 2009/0118786 A1 | 5/2009 | Meadows et al. | |
| 2009/0118787 A1 | 5/2009 | Moffitt et al. | |

FOREIGN PATENT DOCUMENTS

| | | |
|---|---|---|
| EP | 0438945 A1 | 7/1991 |
| EP | 1943944 A1 | 7/2008 |
| GB | 2447640 A | 9/2008 |
| JP | 2008154681 | 7/2008 |
| KR | 20010096372 | 11/2001 |
| RU | 2144310 C1 | 1/2000 |
| WO | WO 97/10747 | 3/1997 |
| WO | WO 00/10455 | 3/2000 |
| WO | WO 02/49500 A2 | 6/2002 |
| WO | WO 02/058536 A2 | 8/2002 |
| WO | 2003101532 A2 | 12/2003 |
| WO | 2003101532 A3 | 12/2003 |
| WO | 2005001707 A2 | 1/2005 |
| WO | 2005001707 A3 | 1/2005 |
| WO | 2005046469 A2 | 5/2005 |
| WO | 2005046469 A3 | 5/2005 |
| WO | WO 2005/089646 A1 | 9/2005 |
| WO | 2005092183 A1 | 10/2005 |
| WO | 2006015002 A1 | 2/2006 |
| WO | 2006020794 A2 | 2/2006 |
| WO | 2006020794 A3 | 2/2006 |
| WO | 2006073915 A2 | 7/2006 |
| WO | 2006073915 A3 | 7/2006 |
| WO | 2006074029 A2 | 7/2006 |
| WO | 2006074029 A3 | 7/2006 |
| WO | 2006076164 A2 | 7/2006 |
| WO | WO2006/121455 A1 | 11/2006 |
| WO | WO 2006/126186 A2 | 11/2006 |
| WO | WO 2007/112092 A2 | 10/2007 |
| WO | WO 2009/059041 A1 | 5/2009 |

OTHER PUBLICATIONS

Office Action for U.S. Appl. No. 11/974,931, mailed Sep. 16, 2010, 11 pages.

Responsive Amendment to Office Action for U.S. Appl. No. 11/974,931, filed Dec. 16, 2010, 15 pages.

Brown et al., "Basal ganglia local field potential activity: Character and functional significance in the human," Clinical Neurology, vol. 116, 2005, pp. 2510-2519.

Peter Brown, M.D., "Oscillatory Nature of Human Basal Ganglia Activity: Relationship to the Pathophysiology of Parkinson's Disease," Movement Disorders, vol. 18, No. 4, 2003, pp. 357-363.

Silberstein et al., "Patterning of globus pallidus local field potentials differs between Parkinson's disease and dystonia," Brain, vol. 126, 2003, pp. 2597-2608.

Harrison et al., "Local Field Potential Measurement with Low-Power Analog Integrated Circuit", Proceedings of the 26th Annual International Conference of the IEEE EMBS, Sep. 1-5, 2004, 4 pages.

Wingeier et al., "Intra-operative STN DBS attenuates the prominent beta rhythm in the STN in Parkinson's disease," Experimental Neurology, 2005, 8 pages.

U.S. Patent Application entitled, "Patient Directed Therapy Control", U.S. Appl. No. 11/974,931, filed Oct. 16, 2007.

U.S. Patent Application entitled, "Frequency Selective Monitoring of Physiological Signals," U.S. Appl. No. 12/237,868, filed Sep. 25, 2008.

Sanes et al., "Plasticity and Primary Motor Cortex", Annual Review of Neuroscience, vol. 23, 2000, pp. 393-415.

Serruya et al., "Robustness of neuroprosthetic decoding algorithms", Biological Cybernetics, vol. 88, 2003, pp. 219-228.

Acuna et al., "Frontal and Parietal Lobe Activation during Transitive Inference in Humans", Cerebral Cortex, vol. 12, No. 12, Dec. 2002, pp. 1312-1321.

Wood et al., "Inferring Attentional State and Kinematics from Motor Cortical Firing Rates", Proceedings of the 2005 IEEE, Engineering in Medicine and Biology 27th Annual Conference, Sep. 1-4, 2005, pp. 149-152.

Hatsopoulos et al., "Cortically controlled brain-machine interface", Proceedings of the 2005 IEEE, Engineering in Medicine and Biology 27th Annual Conference, Sep. 1-4, 2005, pp. 7660-7663.

Wu et al., "Closed-Loop Neural Control of Cursor Motion using a Kalman Filter", Proceedings of the 26th Annual International Conference of the IEEE EMBS, San Francisco, CA, USA, Sep. 1-5, 2004, pp. 4126-4129.

Song et al., "Development of an Integrated Microelectrode/Microelectronic Device for Brain Implantable Neuroengineering Applications", Proceedings of the 26th Annual International Conference of the IEEE EMBS, San Francisco, CA, USA, Sep. 1-5, 2004, pp. 4053-4056.

Eden et al., "Reconstruction of Hand Movement Trajectories from a Dynamic Ensemble of Spiking Motor Cortical Neurons", Proceedings of the 26th Annual International Conference of the IEEE EMBS, San Francisco, CA, USA, Sep. 1-5, 2004, pp. 4017-4020.

Wood et al., "Automatice Spike Sorting for Neural Decoding", Proceedings of the 26th Annual International Conference of the IEEE EMBS, San Francisco, CA, USA, Sep. 1-5, 2004, pp. 4009-4012.

Acuna et al., "Cognitive mechanisms of transitive inference", Exp Brain Res, Sep. 2002, vol. 146, pp. 1-10.

Hochberg et al., "Sensors for Brain-Computer Interfaces: Options for Turning Thought into Action", IEEE Engineering in Medicine and Biology Magazine, Sep./Oct. 2006, pp. 32-38.

Shoham et al., "Statistical Encoding Model for a Primary Motor Cortical Brain-Machine Interface", IEEE Transactions on Biomedical Engineering, vol. 52, No. 7, Jul. 2005, pp. 1312-1322.

Patterson et al., "A Microlectrode/Microelectronic Hybrid Device for Brain Implantable Neuroprosthesis Applications", IEEE Transactions on Biomedical Engineering, vol. 51, No. 10, Oct. 2004, pp. 1845-1853.

Wu et al., "Modeling and Decoding Motor Cortical Activity Using a Switching Kalman Filter", IEEE Transactions on Biomedical Engineering, vol. 51, No. 6, Jun. 2004, pp. 933-942.

Wood et al., "On the Variability of Manual Spike Sorting", IEEE Transactions on Biomedical Engineering, vol. 51, No. 6, Jun. 2004, pp. 912-918.

Suner et al., "Reliability of Signals From a Chronically Implanted, Silicon-Based Electrode Array in Non-Human Primate Primary Motor Cortex", IEEE Transactions on Neural Systems and Rehabilitation Engineering, vol. 13, No. 4, Dec. 2005, pp. 524-541.

Song et al., "Development of a Chipscale Integrated Microelectrode/Microelectronic Device for Brain Implantable Neuroengineering Applications", IEEE Transactions on Neural Systems and Rehabilitation Engineering, vol. 13, No. 2, Jun. 2005, pp. 220-226.

Aaron et al., "Horizons in Prosthesis Development for the Restoration of Limb Function", Journal of the American Academy of Orthopaedic Surgeons, vol. 14, No. 10, 2006, pp. S198-S204.

Ojakangas et al, "Decoding movement intent from human premotor cortex neurons for neural prosthetic applications", Journal of Clinical Neurophysiology, vol. 23, No. 6, Dec. 2006, 14 pages.

Donoghue et al., "Motor Areas of the Cerebral Cortex", Journal of Clinical Neurophysiology. vol. 11, No. 4, pp. 382-396, 1994.

Paninski et al., "Spatiotemporal Tuning of Motor Cortical Neurons for Hand Position and Velocity", Journal of Neurophysiology, vol. 91, 2004, pp. 515-532.

Hess et al., "Long-Term Potentiation of Horizontal Connections Provides a Mechanism to Reorganize Cortical Motor Maps", Journal of Neurophysiology, vol. 71, No. 6, Jun. 1994, pp. 2543-2547.

Paninski et al., "Superlinear Population Encoding of Dynamic Hand Trajectory in Primary Motor Cortex", The Journal of Neuroscience, vol. 24, No. 39, Sep. 29, 2004, pp. 8551-8561.

Maynard et al., "Neuronal Interactions Improve Cortical Population Coding of Movement Direction", The Journal of Neuroscience, vol. 19, No. 18, Sep. 15, 1999, pp. 8083-8093.

Donoghue et al., "Assistive technology and robotic control using motor cortex ensemble-based neural interface systems in humans with tetraplegia", Journal of Physiology 579.3, 2007, pp. 603-611.

Donoghue, "Connecting cortex to machines: recent advances in brain interfaces", Nature Neuroscience, supplement, vol. 5, Nov. 2002, pp. 1085-1088.

Hochberg et al., "Neuronal ensemble control of prosthetic devices by a human with tetraplegia", Nature, vol. 442, Jul. 2006, pp. 164-171.

Serruya et al., "Instant neural control of a movement signal", Nature, vol. 416, Mar. 2002, pp. 141-142.

Wu et al., "Bayesian Population Decoding of Motor Cortical Activity Using a Kalman Filter", Neural Computation, vol. 18, No. 1, 2006, pp. 80-118.

Friehs et al., "Brain-Machine and Brain-Computer Interfaces", Stroke, vol. 35, No. 11, Supplement 1, Nov. 2004, pp. 2702-2705.

Donoghue et al., "Development of neuromotor prostheses for humans", Advances in Clinical Neurophysiology, Supplements to Clinical Neurophysiology, vol. 57, 2004, pp. 592-606.

Schwartz, "Useful signals from motor cortex", Journal of Physiology, vol. 579, No. 3, 2007, pp. 581-601.

Wolpaw, "Brain-computer interfaces as new brain output pathways", Journal of Physiology, vol. 579, No. 3, 2007, pp. 613-619.

Cohen et al., "The physiology of brain-computer interfaces", Journal of Physiology, vol. 579, No. 3, 2007, p. 570.

Fetz, "Volitional control of neural activity: implications for brain-computer interfaces", Journal of Physiology, vol. 579, No. 3, 2007, pp. 571-579.

Heldman et al., "Local Field Potential Spectral Tuning in Motor Cortex During Reaching", IEEE Transactions on Neural Systems and Rehabilitation Engineering, vol. 14, No. 2, Jun. 2006, pp. 180-183.

U.S. Patent Application entitled "Chopper-Stabilized Instrumentation Amplifier", U.S. Appl. No. 11/700,404, filed Jan. 31, 2007, Denison et al.

U.S. Patent Application entitled "Sleep Stage Detection", U.S. Appl. No. 12/238,105, filed Sep. 25, 2008, Wu et al.

U.S. Patent Application entitled "Therapy Adjustment",U.S. Appl. No. 11/799,035, filed Apr. 30, 2007, Gerber et al.

U.S. Patent Application entitled "Shifting Between Electrode Combinations in Electrical Stimulation Device", U.S. Appl. No. 11/401,100, filed Apr. 10, 2006, Goetz et al.

Tornqvist et al., "Effects of Different Electrical Parameter Settings on the Intelligibility of Speech in Patients with Parkinson's Disease Treated With Subthalamic Deep Brain Stimulation", Movement Disorders, vol. 20, No. 4, 2005, pp. 416-423.

U.S. Appl. No. 61/049,166, filed Apr. 30, 2008, entitled, "Sleep Stage Detection".

U.S. Appl. No. 61/023,522, filed Jan. 25, 2008, entitled, "Therapy Program Selection".

U.S. Appl. No. 60/999,096, filed Oct. 16, 2007, entitled, "Device Control Based on Prospective Movement".

U.S. Appl. No. 60/999,097, filed Oct. 16, 2007, entitled, "Frequency Selective Monitoring of Physiological Signals".

U.S. Appl. No. 12/238,025, filed Sep. 25, 2008, entitled, "Therapy Program Selection".

U.S. Appl. No. 60/975,372, filed Sep. 26, 2007, entitled, "Patient Directed Therapy Control".

U.S. Appl. No. 61/025,503, filed Feb. 1, 2008, entitled, "Frequency Selective Monitoring of Physiological Signals".

U.S. Appl. No. 12/237,799, filed Sep. 25, 2008, entitled, "Therapy Control Based on a Patient Movement State".

U.S. Appl. No. 61/083,381, filed Jul. 24, 2008, entitled, "Frequency Selective Monitoring of Physiological Signals".

U.S. Appl. No. 11/700,404, filed Jan. 31, 2007, entitled, "Chopper-Stabilized Instrumentation Amplifier".

Notification of Transmittal of the International Search Report and the Written Opinion of the International Searching Authority for corresponding patent application No. PCT/US2008/011109, 13 pages.

Foffani et al., "Analysis of local field potentials from the human subthalamic nucleus," Proceedings of the 25th Annual International Conference of the IEEE EMBS, Sep. 17-21, 2003, 3 pages.

Notification Concerning Transmittal of International Preliminary Report on Patentability for corresponding patent application No. PCT/US2008/011109, mailed Apr. 29, 2010, 8 pages.

Response to Office Action dated Apr. 4, 2011, from U.S. Appl. No. 11/974,931, filed Aug. 4, 2011, 12 pp.

Office action for U.S. Appl. No. 12/238,025, mailed Mar. 11, 2011, 11 pages.

Office action for U.S. Appl. No. 11/974,931, mailed Apr. 4, 2011, 10 pages.

Response to office action for U.S. Appl. No. 12/238,025, filed Jun. 13, 2011, 13 pages.

* cited by examiner

THERAPY CONTROL BASED ON A PATIENT MOVEMENT STATE

This application claims the benefit of U.S. Provisional Application No. 60/999,096 to Molnar et al., entitled, "DEVICE CONTROL BASED ON PROSPECTIVE MOVEMENT" and filed on Oct. 16, 2007 and U.S. Provisional Application No. 60/999,097 to Denison et al., entitled, "RESPONSIVE THERAPY SYSTEM" and filed on Oct. 16, 2007. The entire contents of above-identified U.S. Provisional Application Nos. 60/999,096 and 60/999,097 are incorporated herein by reference.

TECHNICAL FIELD

The disclosure relates to therapy systems, and, more particularly, controlling a therapy system.

BACKGROUND

Patients afflicted with movement disorders or other neurodegenerative impairment, whether by disease or trauma, may experience muscle control and movement problems, such as rigidity, bradykinesia (i.e., slow physical movement), rhythmic hyperkinesia (e.g., tremor), nonrhythmic hyperkinesia (e.g., tics) or akinesia (i.e., a loss of physical movement). Movement disorders may be found in patients with Parkinson's disease, multiple sclerosis, and cerebral palsy, among other conditions. Delivery of electrical stimulation and/or a fluid (e.g., a pharmaceutical drug) to one or more sites in a patient, such as a brain, spinal cord, leg muscle or arm muscle, in a patient may help alleviate, and in some cases, eliminate symptoms associated with movement disorders.

In some cases, delivery of an external cue, such as a visual, auditory or somatosensory cue, to the patient may also help control some conditions of a movement disorder. For example, delivery of an external cue to the patient may help a patient susceptible to gait freeze or akinesia to initiate movement.

SUMMARY

In general, the disclosure is directed toward controlling therapy delivery to a patient based on a determination of whether a patient is in a movement state based on a brain signal of the patient. For example, some systems and techniques in accordance with this disclosure may determine whether a patient is in a rest (i.e., non-movement) state or a movement state based on a brain signal and control a device to deliver therapy to the patient or change therapy parameter values upon determining the patient is in the movement state. The movement state includes the state in which the patient is generating thoughts of movement (i.e., is intending to move), attempting to initiate movement or is actually undergoing movement.

In some examples, a device may be controlled based on detection of a brain signal within a dorsal-lateral prefrontal (DLPF) cortex of a patient that is indicative of prospective movement of the patient. The device may include, for example, a non-medical appliance (e.g., a lamp), a patient transport device (e.g., a wheelchair or a prosthetic limb) or a therapy delivery device.

In one aspect, the disclosure is directed to a method that includes monitoring a bioelectrical signal from a brain of a patient, determining whether the bioelectrical brain signal indicates the patient is in a movement state, at a first time, controlling delivery of therapy to the patient if the bioelectrical signal indicates the patient is in the movement state, at a second time following the first time, determining whether the patient is in the movement state, and controlling the delivery of the therapy to the patient based on whether the patient is in the movement state at the second time following the first time. For example, the method may include at a second time following the first time, confirming that the patient is in the movement state based on a signal other than the brain signal.

In another aspect, the disclosure is directed to a system comprising a sensing module to monitor a bioelectrical brain signal of a patient and a processor that determines whether the bioelectrical brain signal indicates the patient is in a movement state and, at a first time, controls delivery of therapy to the patient if the bioelectrical brain signal indicates the patient is in a movement state. The processor, at a second time following the first time, determines whether the patient is in the movement state and controls the delivery of the therapy to the patient based on whether the patient is in the movement state at the second time following the first time.

In another aspect, the disclosure is directed to a computer-readable medium comprising instructions. The instructions cause a programmable processor to receive a bioelectrical brain signal, determine whether the bioelectrical brain signal indicates the patient is in a movement state, at a first time, control operation of a therapy device if the bioelectrical brain signal indicates the patient is in a movement state, at a second time following the first time, determine whether the patient is in the movement state, and control the operation of the therapy device based on whether the patient is in the movement state at the second time following the first time.

In another aspect, the disclosure is directed to a method comprising monitoring an EEG signal from a brain of a patient, determining whether the EEG signal indicates the patient is in a movement state, controlling delivery of a sensory cue to the patient if the EEG signal indicates the patient is in the movement state, and confirm the patient is in the movement state based on a motion sensor.

In another aspect, the disclosure is directed to a method comprising means for monitoring a bioelectrical brain signal from a brain of a patient, means for determining whether the brain signal indicates the patient is in a movement state, means for controlling delivery of therapy to the patient if the brain signal indicates the patient is in the movement state at a first time; means for determining whether the patient is in the movement state at a second time following the first time, and means for controlling the delivery of the therapy to the patient based on whether the patient is in the movement state at the second time following the first time.

In another aspect, the disclosure is directed to a method comprising sensing a brain signal indicative of prospective movement of a patient within a dorsal-lateral prefrontal cortex of a brain of the patient, and controlling delivery of movement disorder therapy to the patient based on the sensed brain signal.

In another aspect, the disclosure is directed to a system comprising a sensing module to sense a brain signal indicative of prospective movement of a patient within a dorsal-lateral prefrontal cortex of a brain of the patient, and a controller to control delivery of movement disorder therapy to the patient based on the sensed brain signal.

In another aspect, the disclosure is directed to a method comprising sensing a brain signal indicative of prospective movement of a patient within a dorsal-lateral prefrontal cortex of a brain of the patient, and controlling operation of a device based on the sensed brain signal.

In another aspect, the disclosure is directed to a system comprising a sensing module to sense a brain signal indicative of prospective movement of a patient within a dorsal-lateral prefrontal cortex of a brain of the patient, and a controller that controls a device based on the sensed brain signal.

In another aspect, the disclosure is directed to a system comprising means for sensing a brain signal indicative of prospective movement of a patient within a dorsal-lateral prefrontal cortex of a brain of the patient, and means for controlling operation of a device based on the sensed brain signal.

In another aspect, the disclosure is directed to a computer-readable medium containing instructions. The instructions cause a programmable processor to receive input indicating a signal from a dorsal-lateral prefrontal cortex of a brain of a patient, determine whether the signal indicates prospective movement of the patient, and control operation of a device if the signal indicates prospective movement.

In other aspects, the disclosure is directed toward a computer-readable medium containing instructions. The instructions cause a programmable processor to perform any part of the techniques described herein.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1A:
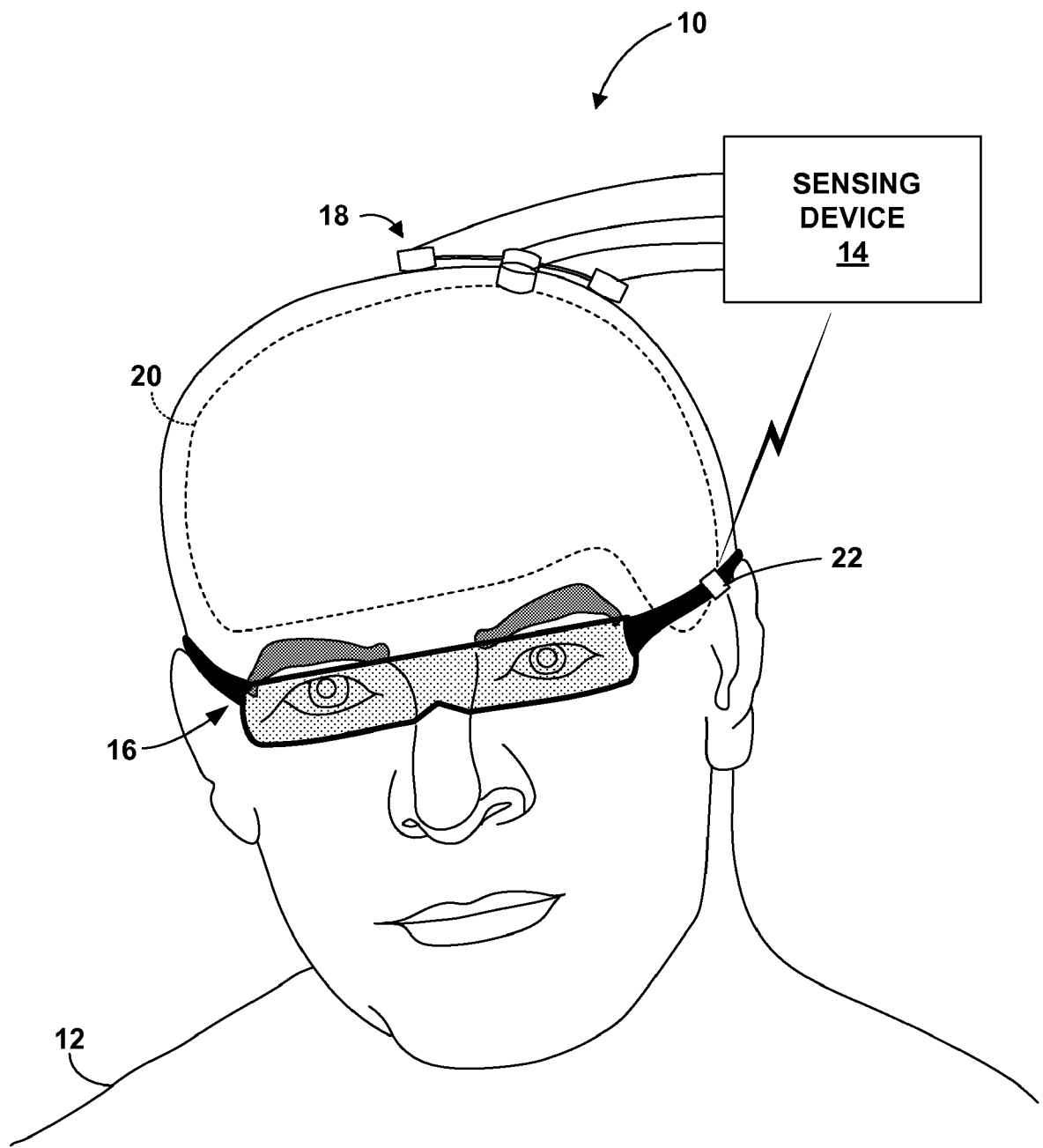
FIG. 1A is a schematic diagram illustrating an example therapy system that delivers therapy to control a movement disorder of a patient.

Therapy delivery to a patient may be controlled based on a determination of whether a patient is in a movement state based on a brain signal of the patient. The brain signal may include a bioelectrical signal, such as an electroencephalogram (EEG) signal, an electrocorticogram (ECoG) signal, a signal generated from measured field potentials within one or more regions of a patient's brain and/or action potentials from single cells within the patient's brain. In some examples, the brain signal may be detected within a dorsal-lateral prefrontal (DLPF) cortex of the patient's brain. The movement state includes the state in which the patient is generating thoughts of movement (i.e., is intending to move), initiating movement, attempting to initiate movement or is actually undergoing movement. The therapy may include, for example, electrical stimulation, fluid delivery or a sensory cue (e.g., visual, somatosensory or auditory cue) delivered to the patient via an external or implanted device. The therapy delivery may help the patient control symptoms of a movement disorder or other neurodegenerative impairment. For example, in one example, delivery of an external sensory cue may help the patient initiate movement or more effectively undertake or continue movement.

In order to determine whether the bioelectrical signal indicates the patient is in a movement state or a rest state, the bioelectrical signal may be analyzed for comparison of a voltage or amplitude value with a stored value, temporal or frequency correlation with a template signal, a particular power level within a particular frequency band of the bioelectrical signal, or combinations thereof. In one example, a processor of a bioelectrical sensing device may monitor the power level of the mu rhythm within an alpha frequency band (e.g., about 5 Hertz (Hz) to about 10 Hz) of an EEG signal. If the power level of the mu rhythm falls below a particular threshold, which may be determined during a trial period, the EEG signal may indicate the patient is in a movement state. The sensing device may then control a therapy device to deliver a therapy to the patient to mitigate the effects of a movement disorder. For example, the sensing device may generate a control signal that is transmitted to the therapy device and causes the therapy device to initiate therapy delivery or adjust one or more therapy delivery parameter values.

In some examples, the therapy systems and methods also include deactivating the delivery of therapy or changing therapy parameters upon determining the patient is in the rest state (i.e., as stopped moving) or has successfully initiated movement, depending upon the type of movement disorder symptom the therapy system is implemented to address. In addition, in some examples, a first determination that the patient is in a movement stated based on brain signals may be confirmed by a second determination that is based on another source that is independent of the brain signals, such as a motion sensor.

FIG. 1A is a schematic diagram illustrating an example therapy system 10 that delivers therapy to control a movement disorder or a neurodegenerative impairment of patient 12. Patient 12 ordinarily will be a human patient. In some cases, however, the systems and techniques described herein may be applied to non-human patients. The movement disorder or other neurodegenerative impairment may include, for example, muscle control, motion impairment or other movement problems, such as rigidity, bradykinesia, rhythmic hyperkinesia, nonrhythmic hyperkinesia, akinesia. In some cases, the movement disorder may be a symptom of Parkinson's disease. However, the movement disorder may be attributable to other patient conditions. Although movement disorders are primarily referred to throughout the remainder of the application, the therapy systems and methods described herein are also useful for controlling symptoms of other conditions, such as neurodegenerative impairment.

Therapy system 10, which includes sensing device 14 and external cue device 16, may improve the performance of motor tasks by patient 12 that may otherwise be difficult. These tasks include at least one of initiating movement, maintaining movement, grasping and moving objects, improving gait associated with narrow turns, and so forth. External cue device 16 generates and delivers a sensory cue, such as a visual, auditory or somatosensory cue, to patient 12 in order to help control at least one symptom of a movement disorder. For example, if patient 12 is prone to gait freeze or akinesia, a sensory cue may help patient 12 initiate or maintain movement. In other examples, external cues delivered by external cue device 16 may be useful for controlling other movement disorder conditions, such as, but not limited to, rigidity, bradykinesia, rhythmic hyperkinesia, and nonrhythmic hyperkinesia.

Rather than requiring patient 12 to manually activate external cue device 16, therapy system 10 automatically activates external cue device 16 in response to a sensed state, condition or event. In some cases, therapy system 10 also automatically deactivates external cue device 16 upon determining that active therapy delivery is no longer desirable, e.g., upon determining patient 12 is no longer in a movement state or has successfully initiated movement. Sensing device 14 detects a movement state of patient 12 based on a brain signal of brain 20 of patient 12 and transmits a signal to external cue device 16 in response to detecting the movement state. The brain signal may be a bioelectrical signal within one or more regions of brain 20 that indicate patient 12 is intending on initiating movement, attempting to initiate movement, or is actually moving. Accordingly, the "movement state" generally indicates a brain state in which patient 12 is intending on initiating movement, attempting to initiate movement (e.g., patient 12 is attempting to move, but because of the movement disorder, patient 12 cannot successfully initiate the movement) or is actually moving. Thus, detecting a movement state includes detecting a patient's intention to move. In contrast, a "rest state" generally indicates a brain state in which patient 12 is at rest, i.e., is not intending on moving and is not actually moving.

Examples of bioelectrical signals include an electroencephalogram (EEG) signal, an electrocorticogram (ECoG) signal, a signal generated from measured field potentials within one or more regions of brain 20 or action potentials from single cells within brain 20 (referred to as "spikes"). Determining action potentials of single cells within brain 20 may require resolution of bioelectrical signals to the cellular level and provides fidelity for fine movements, i.e., a bioelectrical signal indicative of fine movements (e.g., slight movement of a finger). While the remainder of the disclosure primarily refers to EEG signals, in other examples, sensing device 14 may be configured to determine whether patient 12 is in a movement state based on other types of bioelectrical signals from within brain 20 of patient 12.

After sensing device 14 determines that patient 12 is in a movement state, external cue device 16 may deliver a sensory cue, such as a visual, somatosensory or auditory cue, to patient 12 in order to help control the movement disorder. Automatic activation of external cue device 16 may help provide patient 12 with better control and timing of therapy delivery by external cue device 16 by eliminating the need for patient 12, who exhibits some difficulty with movement, to manually activate external cue device 16. In addition, automatically initiating the delivery of a sensory cue in response to detecting a movement state may enable therapy system 10 to minimize the time between when patient 12 needs the therapy and when the therapy is actually delivered.

Therapy system 10 provides a responsive system for controlling the delivery of therapy to patient 12. As one example of the responsiveness of therapy system 10, therapy system 10 times the delivery of therapy to patient 12 such that patient 12 receives the therapy at a relevant time, i.e., when it is particularly useful to patient 12. In contrast, an external cue device that requires patient 12 to purposefully initiate the delivery of a sensory cue by interacting with an input mechanism (e.g., a programmer or a button on device 16 or another device) may be less useful. For example, if patient 12 exhibits motion impairment, patient 12 may find it difficult to initiate the movement to activate external cue device 16 (e.g., via a button or another input mechanism). Thus, in some cases, therapy system 10 may improve a quality of life of patient 12. While akinesia is the movement disorder primarily discussed herein during the description of therapy system 10, as well as the other therapy system examples herein, in other examples, the therapy systems described herein may be useful for treating other movement disorders or other conditions that may affect the patient's ability to move.

Sensing device 14 is electrically coupled to electrode array 18, which is positioned on a surface of the cranium of patient 12 proximate to a motor cortex of brain 20. In the example shown in FIG. 1, sensing device 14, via electrode array 18, is configured to generate an EEG signal that indicates the electrical activity within the motor cortex of brain 20, which is indicative of whether patient 12 is in a rest state or a movement state. The signals from the EEG are referred to as "EEG signals." The motor cortex is defined by regions within the cerebral cortex of brain 20 that are involved in the planning, control, and execution of voluntary motor functions, such as walking and lifting objects. Typically, different regions of the motor cortex control different muscles. For example, different "motor points" within the motor cortex may control the movement of the arms, trunk, and legs of patient. Accordingly, electrode array 18 may be positioned to sense the EEG signals within particular regions of the motor cortex depending on what type of therapy the system 10 is designed to deliver. For example, if patient 12 has difficulty initiating movement of arms, electrode array 18 may be positioned to sense the EEG signals at a motor point that is associated with the movement of the arms in order to detect the patient's arm movement, attempted arm movement or intention to move arms. In other examples, electrode array 18 may be positioned proximate to other relevant regions of brain 20, such as, but not limited to, the sensory motor cortex, cerebellum or the basal ganglia.

An EEG is typically a measure of voltage differences between different parts of brain 20, and, accordingly, electrode array 18 may include two or more electrodes. Sensing device 14 may measure the voltage across at least two electrodes of array 18. As described in further detail below, in one example, sensing device 14 includes a processor that determines whether the EEG signals indicate patient 12 is in a movement state, and if so, controls external cue device 16 to deliver a cue to patient 12 to help patient 12 initiate movement or maintain movement. In one example, a processor within sensing device 14 determines whether the alpha frequency band component of the EEG signal detected within the occipital cortex of patient 12 indicates whether patient 12 is in a relaxed state, indicating a lack of movement or a lack of an intention to move, or a movement state, which indicates patient 12 intends to move, is intending to move, is attempting to move or is moving.

It has been found that the alpha band component (referred to as the "alpha waves" of the EEG signal) exhibits a detectable increase in amplitude when patient 12 undergoes a transition from a movement state to a relaxed state. Thus, if sensing device 14 detects a decrease in the power level of the alpha waves, the EEG signal may indicate patient 12 is intending on moving, and, thus, is in a movement state. In response to detecting the movement state, sensing device 14 may deliver an external cue to patient 12 via external cue device 16. In another example, sensing device 14 relays the EEG signals to another device, which includes a processor that determines the EEG signals indicate patient 12 is in a movement state.

While certain symptoms of a patient's movement disorder may generate detectable changes within a monitored EEG signal, the symptomatic EEG signal changes are not indicative of a movement state or rest state, as the terms are used herein. Rather than monitoring the EEG signal for detecting a patient's symptom, sensing device 14 detects a volitional intention by the patient to move or an actual volitional movement via the EEG signals. Sensing device 14 detects an EEG signal (or other brain signal) that is generated in response to a volitional patient movement (whether it is just the mere intention of the movement or actual movement), which differs from an EEG signal that is generated because of a symptom of the patient's condition. Thus, the EEG signals and other brain signals in the methods and systems described herein are non-symptomatic. Furthermore, the EEG signal and other brain signals that provides the feedback to control a therapy device results from a volitional patient movement or intention to move, rather than an incidental electrical signal within the patient's brain that the patient did not voluntarily or intentionally generate. Thus, sensing device 14 detects a brain signal that differs from involuntary neuronal activity that may be caused by the patient's condition (e.g., a tremor or a seizure).

External cue device 16 is any device configured to deliver an external cue to patient 12. As previously described, the external cue may be a visual cue, auditory cue or somatosensory cue (e.g., a pulsed vibration). Visual cues, auditory cues or somatosensory cues may have different effects on patient 12. For example, in some patients with Parkinson's disease, an auditory cue may help the patients grasp moving objects, whereas somatosensory cues may help improve gait and general mobility. Although external cue device 16 is shown as an eyepiece worn by patient 12 in the same manner as glasses, in other examples, external cue device 16 may have different configurations. For example, if an auditory cue is desired, an external cue device may take the form of an ear piece (e.g., an ear piece similar to a hearing aid or head phones). As another example, if a somatosensory cue is desired, an external cue device may take the form of a device worn on the patient's arm or legs (e.g., as a bracelet or anklet), around the patient's waist (e.g., as a belt) or otherwise attached to the patient in a way that permits the patient to sense a somatosensory cue. A device coupled to the patient's wrist may, for example, provide a pulse, pulsed vibration, or other tactile stimulus.

External cue device 16 includes receiver 22 that is configured to communicate with sensing device 14 via a wired or wireless signal. Accordingly, sensing device 14 may include a telemetry module that is configured to communicate with receiver 22. Examples of local wireless communication techniques that may be employed to facilitate communication between sensing device 14 and receiver 22 of device 16 include radiofrequency (RF) communication according to the 802.11 or Bluetooth specification sets, infrared communication, e.g., according to the IrDA standard, or other standard or proprietary telemetry protocols.

Upon detecting a movement state based on EEG signals, sensing device 14 may transmit a signal to receiver 22. A controller within external cue device 16 may initiate the delivery of the external cue in response to receiving the signal from receiver 22. In some cases, external cue device 16 may also include a motion detection element (or a motion sensor), such as an accelerometer, that determines when patient 12 has stopped moving. In such examples, external cue device 16 may transmit the signals from the motion detection element to sensing device 14, which may process the signals to determine whether patient 12 has stopped moving. Alternatively, the motion detection element may be separate from external cue device 16 and may transmit electrical signals indicative of patient movement to sensing device 14.

Upon detecting patient 12 has stopped moving, sensing device 14 may provide a control signal to external cue device 16 via transmitter 22 that deactivates the delivery of the cue. In other examples, external cue device 16 may include a processor that process the signals from the motion detection element and a controller that deactivates the cue delivery upon detecting patient 12 has stopped moving, i.e., is in a rest state. For example, external cue device 16 may repeatedly deliver a sensory cue to patient 12 until movement stoppage is detected. In some examples the relevant determination for terminating the cue delivery may be whether patient 12 has successfully initiated movement. For example, if patient 12 exhibits akinesia, therapy system 10 may be implemented to help patient 12 initiate movement, and once movement is initiated, further therapy may not necessarily be useful.

As described in further detail below with respect to FIG. 12, the motion detection element of external cue device 16 or another motion detection element that is separate from external cue device 16 may also be used to make an independent determination that patient 12 is in a movement state (e.g., confirm patient 12 is actually moving). This independent determination of whether patient 12 is in the movement state may be useful for detecting false positive movement state detections and minimizing unnecessary delivery of therapy to patient 12. In effect, a motion detection element may support a cross-correlation with the movement state detected from the patient's brain signal to confirm movement with greater confidence.

In addition, in some examples, a second determination as to whether patient 12 is in a movement state based on the motion detection element may also be used to further control external cue device 16, such as to deactivate device 16 if patient 12 is not in a movement state or deliver therapy according to a different set of therapy parameter values. The different set of therapy parameter values may be used to help control a different symptom of a movement disorder. For example, the initial therapy delivery by external cue device 16 based on the EEG signals may be used to help patient 12 initiate movement, and a second set of therapy parameters may be implemented upon determining that patient 12 is in fact in the movement state, e.g., to help improve patient gait.

Sensing device 14 may employ an algorithm to suppress false positives, i.e., the detection of a bioelectrical brain signal falsely indicating a movement state. For example, sensing device 14 may implement an algorithm that identifies particular attributes of the biosignal (e.g., certain frequency characteristics of the biosignal) that are unique to the patient's movement state. As another example, sensing device 14 may monitor the characteristics of the biosignal in more than one frequency band, and correlate a particular pattern in the power of the brain signal within two or more frequency bands in order to determine whether the brain signal is indicative of the volitional patient input. The specific characteristics may include, for example, a pattern or behavior of the frequency characteristics of the bioelectrical brain signal, and so forth.

Figure 1B:
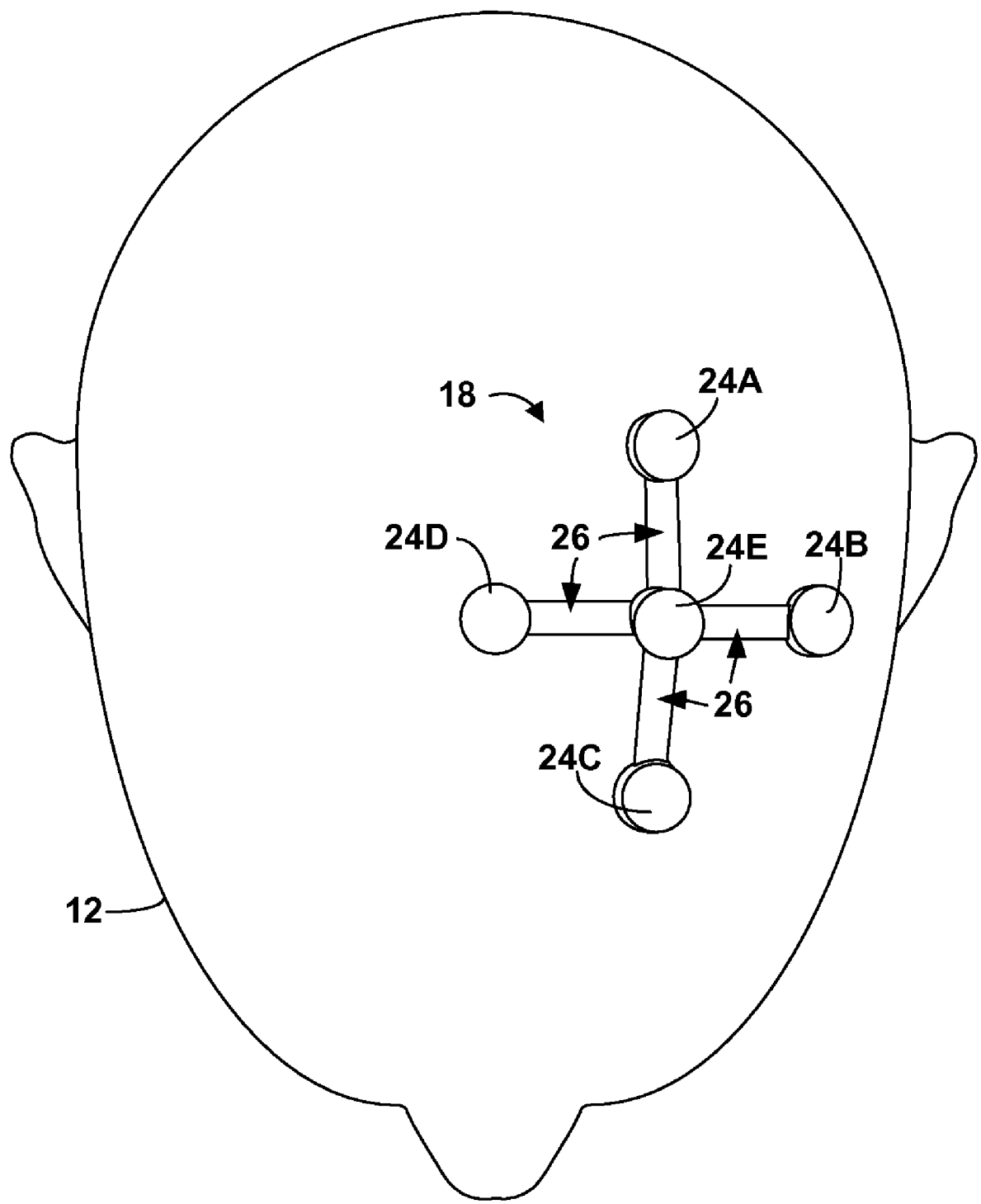
FIG. 1B is a top view of the head of the patient shown in FIG. 1A and illustrates an example electrode array.

FIG. 1B is a top view of the patient's head and illustrates an example electrode array 18, which includes electrodes 24A-24E coupled together via connecting members 26. Electrodes 24A-24E may comprise any suitable surface electrodes that may measure electrical activity within brain 20 of patient 12. Although five electrodes are shown in FIG. 1B, in other examples, electrode array 18 may include any suitable number of electrodes. It may be desirable to minimize the number of electrodes 24A-24E for aesthetic purposes, while maintaining enough electrodes 24A-24E to generate a useful EEG for detecting a movement state of patient 12.

Connecting members 26 may be made out of any suitable flexible or rigid material, such as, but not limited to stainless steel, titanium, silicone, polyimide or another polymer. Electrodes 24A-24E of array 18 are arranged relative to each other in order to adapt to the curvature of the patient's head, as well as cover a large enough portion of the relevant region of brain 20 to measure the electrical activity. Electrode array 18 may be flexible to adapt to the particular curvature of a patient's head, or may have a predetermined curvature that is based on the average curvature of multiple patients' heads. Electrode array 18 may be positioned above the patient's scalp or implanted below the patient's scalp. Electrode array 18 may be coupled to sensing device 14 via wireless telemetry or via a wired connection (e.g., a cable or lead). In this way, sensing device 14 may sense brain signals of patient 12 via electrodes 24A-24E of electrode array 18.

Electrodes 24A-24E may be attached to the patient's head via any suitable technique. For example, a conductive adhesive, such as, but not limited to, tragacanth gum, karaya gum, acrylates, and conductively loaded hydrogels may be used and positioned between electrodes 24A-24E and the surface of the patient's head. A clinician may locate the target site for electrode array 18 on the patient's head via any suitable technique. The target site is typically selected to correspond to the region of brain 20 that generates an EEG signal indicative of the relevant motion. As previously described, different parts of the motor cortex of brain 20 may correspond to different types of movement (e.g., movement of an arm or leg). Thus, if the clinician is primarily concerned with detecting a movement state of the patient's legs, the clinician may select a target site on the cranium of patient 12 that corresponds to the region within the motor cortex associated with leg movement.

In one example, the clinician may initially place electrode array 18 on the patient's head based on the general location of the target region (e.g., it is known that the motor cortex is a part of the cerebral cortex, which may be near the front of the patient's head) and adjust the location of electrodes 24A-24E as necessary to capture the electrical signals from the target region. In another example, the clinician may rely on the "10-20" system, which provides guidelines for determining the relationship between a location of an electrode and the underlying area of the cerebral cortex.

In addition, if electrodes 24A-24E are used to detect movement of specific limbs (e.g., fingers, arms or legs) of patient 12, the clinician may locate the particular location for detecting movement of the specific limb via any suitable technique. In one example, the clinician may utilize an imaging device, such as magnetoencephalography (MEG), positron emission tomography (PET) or functional magnetic resonance imaging (fMRI) to identify the region of the motor cortex of brain 20 associated with movement of the specific limb. In another example, the clinician may map EEG signals from different parts of the motor cortex and associate the EEG signals with movement of the specific limb in order to identify the motor cortex region associated with the limb. For example, the clinician may attach electrodes 24A-24E over the region of the motor cortex that exhibited the greatest detectable change in EEG signal at the time patient 12 actually moved the limb.

Figure 2:
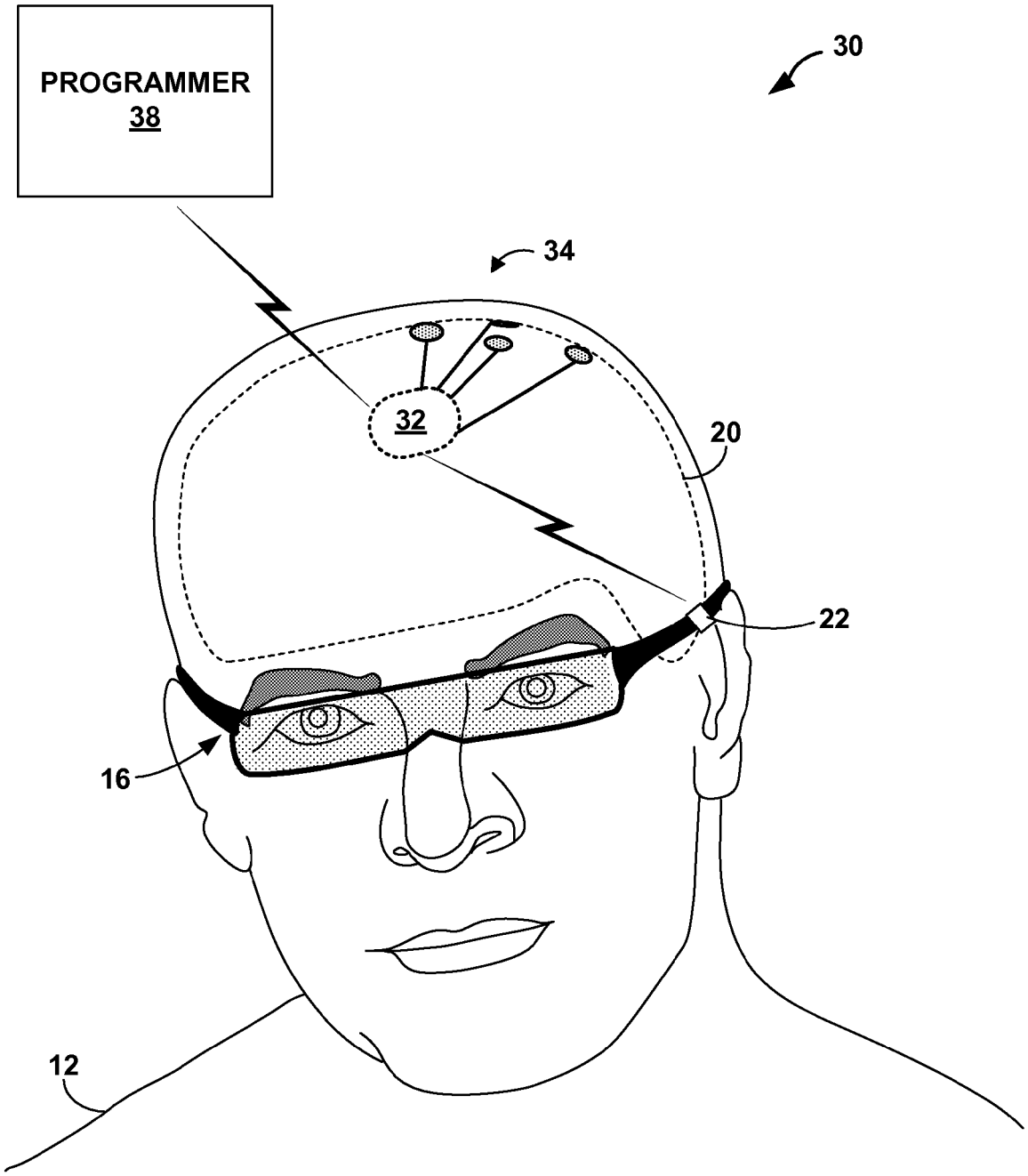
FIG. 2 is a schematic diagram of another example therapy system, which includes an external cue device, an implanted medical device, and a programmer.

FIG. 2 is a schematic diagram of another example of therapy system 30, which includes external cue device 16, an implantable medical device (IMD) 32 coupled to an array 34 of implanted electrodes, and programmer 38. IMD 32 is similar to sensing device 14 shown in FIG. 1, but is implanted within patient 12. In the example of FIG. 2, IMD 32 may be subdurally implanted (e.g., in a hollowed-out or recessed area of the skull or under the skull) in patient 12. In other examples, IMD 32 may be implanted in another region of patient 12, such as in a subcutaneous pocket in a chest cavity or back of patient 12. In some examples, a housing of IMD 32 may include or otherwise define another electrode for measuring the EEG signal. IMD 32 is configured to communicate with transmitter 22 of external cue device via wireless communication techniques, such as RF telemetry techniques.

Electrode array 34 is also similar to electrode array 18 of FIG. 1, but is implanted within the head of patient 12. In some examples, electrode array 34 may be surgically implanted under the dura matter of brain 20 or within the cerebral cortex of brain 20 via a burr hole in a skull of patient 12, and electrically coupled to IMD 32 via one or more leads. If IMD 32 is implanted in a region of patient 12 other than the head, the lead coupling the electrode array 34 to IMD 32 may be surgically implanted through a burr hole in the skull and routed through subcutaneous tissue to the implanted IMD 32. In some cases, electrodes 34 implanted closer to the target region of brain 20 may help generate an EEG signal that provides more useful information than an EEG generated via a surface electrode array 18 because of the proximity to brain 20. The EEG signal that is generated from implanted electrode array may also be referred to as an electrocorticograph (ECoG).

Programmer 38 may be a handheld computing device that permits a clinician to communicate with IMD 32 during initial programming of IMD 32, and for collection of information and further programming during follow-up visits to the clinician's office. Programmer 38 supports telemetry (e.g., RF telemetry or telemetry via the Medical Implant Communication Service (MICS)) with IMD 32 to, for example, download EEG data or other data stored, and sometimes collected, by IMD 32 or upload information (e.g., operating software) to IMD 32. Programmer 38 may also be a handheld computing device for use by patient 12 to interact with IMD 32. Patient 12 may also retrieve information collected by IMD 32 via patient programmer 38.

Programmer 38 may also be configured to communicate with external cue device 16 via any of the aforementioned local wireless communication techniques, such as RF telemetry techniques. Patient 12 or a clinician may modify the external cues delivered by external cue device 16 with the aid of programmer 38. For example, patient 12 may decrease or increase the contrast or brightness of a visual cue, increase or decrease the longevity of the visual cue, increase or decrease the volume of an auditory cue, increase or decrease the intensity of a somatosensory cue (e.g., the intensity of vibration) and so forth.

Programmer 38 may include a user interface comprising an input mechanism, such as a keypad or peripheral device (e.g., a stylus or mouse), and a display, such as a liquid crystal display (LCD) or a light emitting diode (LED) display. In some examples, the display of programmer 38 may comprise a touch screen display, and a user may interact with programmer 38 via the touch screen display. Programmer 38 is not limited to a hand-held computing device, but in other examples, may be any sort of computing device, such as a tablet-based computing device, a desktop computing device, or a workstation.

Figure 3:
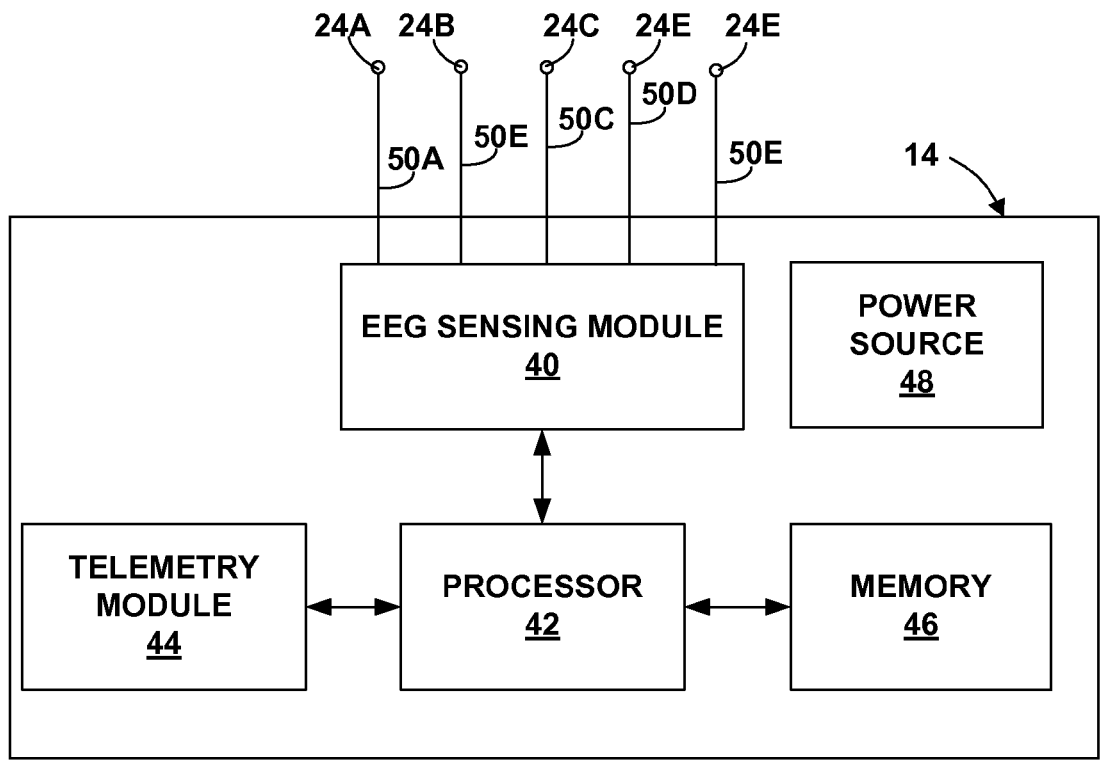
FIG. 3 is a block diagram illustrating an example sensing device.

FIG. 3 is a block diagram illustrating an example sensing device 14, which monitors an EEG signal via electrodes 24A-24E (FIG. 1B) of electrode array 18 and controls external cue device 16 to deliver a cue to patient 12 to help control the effects of a movement disorder, e.g., to help initiate movement. Sensing device 14 includes EEG sensing module 40, which is coupled to electrodes 24A-24E via leads 50A-50E, respectively, processor 42, telemetry module 44, memory 46, and power source 48. Two or more of leads 50A-50E may be bundled together (e.g., as separate conductors within a common lead body) or may include separate lead bodies.

EEG sensing module 40, processor 42, as well as other components of sensing device 14 requiring power may be coupled to power source 48. Power source 48 may take the form of a rechargeable or non-rechargeable battery. Processor 42 controls telemetry module 44 to exchange information with programmer 38 and/or external cue device 16. In some examples, sensing module 14 may include separate telemetry modules for communicating with programmer 38 and external cue device 16. Telemetry module 44 may operate as a transceiver that receives telemetry signals from external cue device 16 and transmits telemetry signals to an external cue device 16. External cue device 16 may provide information to sensing device 14, such as a confirmation that a cue was delivered to patient 12 or information regarding the operation of external cue device 16, such as a battery level of external cue device 16.

In some examples, processor 42 stores monitored EEG signals in memory 46, and/or transmits the values to programmer 38 via telemetry module 44. Memory 46 of sensing device 14 may include any volatile or non-volatile media, such as a random access memory (RAM), read only memory (ROM), non-volatile RAM (NVRAM), electrically erasable programmable ROM (EEPROM), flash memory, and the like. Memory 46 may also store program instructions that, when executed by processor 42, cause processor 42 and the components of sensing device 14 to provide the functionality ascribed to them herein, e.g., cause EEG sensing module 40 to monitor the EEG signal of brain 20. Accordingly, computer-readable media storing instructions may be provided to cause processor 42 to provide functionality as described herein.

EEG sensing module 40 includes circuitry that measures the electrical activity of a particular region, e.g., motor cortex, within brain 20 via electrodes 24A-24E. EEG sensing module 40 may acquire the EEG signal substantially continuously or at regular intervals, such as at a frequency of about 1 Hz to about 200 Hz. EEG sensing module 40 includes circuitry for determining a voltage difference between two electrodes 24A-24E, which generally indicates the electrical activity within the particular region of brain 20. One of the electrodes 24A-24E may act as a reference electrode, and, with respect to IMD 32 (FIG. 2), a housing of IMD 32 may act as a reference electrode. An example circuit that EEG sensing module 40 may include is shown and described below with reference to FIGS. 15-20. In some cases, the EEG signals measured from via external electrodes 24A-24E may generate a voltage in a range of about 5 microvolts ($\mu$V) to about 100 $\mu$V.

The output of EEG sensing module 40 may be received by processor 42. Processor 42 may apply additional processing to the signals, e.g., convert the output to digital values for processing and/or amplify the EEG signal. In some cases, a gain of about 90 decibels (dB) is desirable to amplify the EEG signals. In some examples, EEG sensing module 40 or processor 42 may filter the signal from electrodes 24A-24E in order to remove undesirable artifacts from the signal, such as noise from electrocardiogram (ECG) signals, electromyogram (EMG) signals, and electro-oculogram signals generated within the body of patient 12.

Processor 42 may also control the frequency with which EEG sensing module 40 generates an EEG signal. Processor 42 may include any one or more of a microprocessor, a controller, a digital signal processor (DSP), an application specific integrated circuit (ASIC), a field programmable gate array (FPGA), discrete logic circuitry or the like. The functions attributed to processor 42 herein may be embodied as software, firmware, hardware or any combination thereof.

Processor 42 also controls the delivery of an external cue to patient 12 based on the output of EEG sensing module 40. In one example, processor 42 determines whether the EEG signal indicates patient 12 is in a rest state or a movement state. If processor 42 determines the EEG signal indicates patient 12 is in a movement state, processor 42 may generate a movement indication. The movement indication may be a value, flag, or signal that is stored or transmitted to indicate the movement state. Processor 42 may transmit the movement indication to receiver 22 of external cue device 16, which, in response, may deliver the external cue to patient 12. In this way, the movement indication may be a control signal for activating external cue device 16. In some examples, processor 42 may record the movement indication in memory 46 for later retrieval and analysis by a clinician. For example, movement indications may be recorded over time, e.g., in a loop recorder, and may be accompanied by the relevant EEG signal.

Processor 42 may determine whether the EEG signal from EEG sensing module 40 indicates patient 12 is in a movement state or a rest state via any suitable technique. If processor 42 determines that the EEG signal indicates patient 12 is in a rest state, the EEG signal likewise indicates patient 12 is not in a movement state. As various examples of signal processing techniques that processor 42 may employ, the EEG signals may be analyzed for a particular relationship of the voltage or current amplitude of the EEG waveform to a threshold value, temporal correlation or frequency correlation with a template signal, or combinations thereof. For example, the instantaneous or average amplitude of the EEG signal over a period of time may be compared to an amplitude threshold. For example, in one example, when the amplitude of the EEG signal is greater than or equal to the threshold value, processor 42 may control external cue device 16 to deliver the external cue to patient 12.

As another example, a slope of the amplitude of the EEG signal over time or timing between inflection points or other critical points in the pattern of the amplitude of the EEG signal over time may be compared to trend information. A correlation between the inflection points in the amplitude waveform of the EEG signal or other critical points and a template may indicate a movement state or a rest state. Processor 42 may implement an algorithm that recognizes a trend of the EEG signals that characterize a brain state that indicates patient 12 is intending on moving. If the trend of the EEG signals matches or substantially matches the trend template, processor 42 may control external cue device 16 to deliver the external cue to patient 12.

As another example, processor 42 may perform temporal correlation by sampling the EEG signal with a sliding window and comparing the sampled waveform with a stored template waveform. For example, processor 42 may perform a correlation analysis by moving a window along a digitized plot of the amplitude waveform of EEG signals at regular intervals, such as between about one millisecond to about ten millisecond intervals, to define a sample of the EEG signal. The sample window is slid along the plot until a correlation is detected between the waveform of the template and the waveform of the sample of the EEG signal defined by the window. By moving the window at regular time intervals, multiple sample periods are defined. The correlation may be detected by, for example, matching multiple points between the template waveform and the waveform of the plot of the EEG signal over time, or by applying any suitable mathematical correlation algorithm between the sample in the sampling window and a corresponding set of samples stored in the template waveform.

Different frequency bands are associated with different activity in brain 20. One example of the frequency bands is shown in Table 1 below:

TABLE 1

| Frequency (f) Band Hertz (Hz) | Frequency Information |
|---|---|
| $f < 5$ Hz | $\delta$ (delta frequency band) |
| $5$ Hz $\leq f \leq 10$ Hz | $\alpha$ (alpha frequency band) |
| $10$ Hz $\leq f \leq 30$ Hz | $\beta$ (beta frequency band) |
| $50$ Hz $\leq f \leq 100$ Hz | $\gamma$ (gamma frequency band) |
| $100$ Hz $\leq f \leq 200$ Hz | high $\gamma$ (high gamma frequency band) |

It is believed that some frequency bands of the EEG signal may be more revealing of the patient's movement state than other frequency bands. In one example, the patient's movement state is detected by looking at particular frequency components of the EEG signal. Various frequency bands of the EEG signal are associated with particular stages of movement. For example, the alpha band from Table 1 may be more revealing of a rest state, in which patient 12 is awake, but not active, than the beta band. EEG signal activity within the alpha band may attenuate with an increase or decrease in physical activity. A higher frequency band, such as the beta or gamma bands, may also attenuate with an increase or decrease in physical activity. For example, the "high" gamma band, which may include a frequency band of about 100 Hz to about 200 Hz, such as about 150 Hz, may be revealing of the patient's movement state. The relative power levels within the high gamma band (e.g., about 100 Hz to about 200 Hz) of an EEG signal, as well as other bioelectric signals, has been shown to be both an excellent biomarker for motion intent, as well as flexible to human control. That is, a human patient may control activity within the high gamma band with volitional thoughts, e.g., relating to initiating movement.

Either EEG sensing module 40 or processor 42 may tune the EEG signal to a particular frequency band that is indicative of the patient's intention to move. In some examples, EEG sensing module 40 or processor may tune the EEG signal to the alpha and/or high gamma bands. The power level within the selected frequency band may be indicative of whether the EEG signal indicates patient 12 is in a movement state. For example, a relatively low power level within the alpha band or a relatively high power level within the high gamma band may indicate the movement state. The high gamma band component of the EEG signal or another bioelectrical signal of interest may be easier to extract than the alpha band component because the gamma band includes less noise than the alpha band. The noise may be due to, for example, other bioelectrical signals. In another example, the ratio of power levels within two or more frequency bands may be compared to a stored value in order to determine whether the EEG signal indicates patient 12 is in a movement state.

In another example, the correlation of changes of power between frequency bands may be compared to a stored value to determine whether the EEG signal indicates patient 12 is in a movement state. For example, if the power level within the alpha band (e.g., a mu wave power) decreases and indicates patient 12 is in a movement state, and within a certain amount of time or at substantially the same time, the power level within the high gamma band of the EEG signal increases, processor 42 may confirm that patient 12 is in the movement state. This correlation of changes in power of different frequency bands may be implemented into an algorithm that helps processor 42 eliminate false positive detections of the movement state, i.e., by providing confirmation that the low power level (e.g., as compared to a stored value or trend template) within the alpha band or high power level within the gamma band (e.g., as compared to a stored value or trend template) indicates patient 12 is in the movement state.

In some examples, the EEG signal may be analyzed in the frequency domain to compare the power level of the EEG signal within one or more frequency bands to a threshold or to compare selected frequency components of an amplitude waveform of the EEG signal to corresponding frequency components of a template signal. The template signal may indicate, for example, a trend in the power level within one or more frequency bands that indicates patient 12 is in a movement state. Specific examples of techniques for analyzing the frequency components of the EEG signal are described below with reference to FIGS. 8 and 9.

In various examples, processor 42 may monitor different frequency components of an EEG signal to determine whether patient 12 is in a movement state. A mu rhythm, which is also referred to as a "mu wave," is one component of the EEG signal that is present in the alpha frequency band. Mu waves are a particular wave of electromagnetic oscillations in the alpha frequency band. In some examples, processor 42 monitors the mu rhythm to determine whether patient 12 is in a movement state, and thus, whether to control external cue device 16 to deliver a cue to patient 12. When the power level of the mu rhythm oscillations is relatively high, the EEG signal may indicate patient 12 is in a rest state and is not in a movement state. On the other hand, when the power level of the mu rhythm is relatively low in the alpha band, the EEG signal may indicate patient 12 is in a movement state, e.g., is actually moving, thinking about moving or attempting to move.

Figure 4:
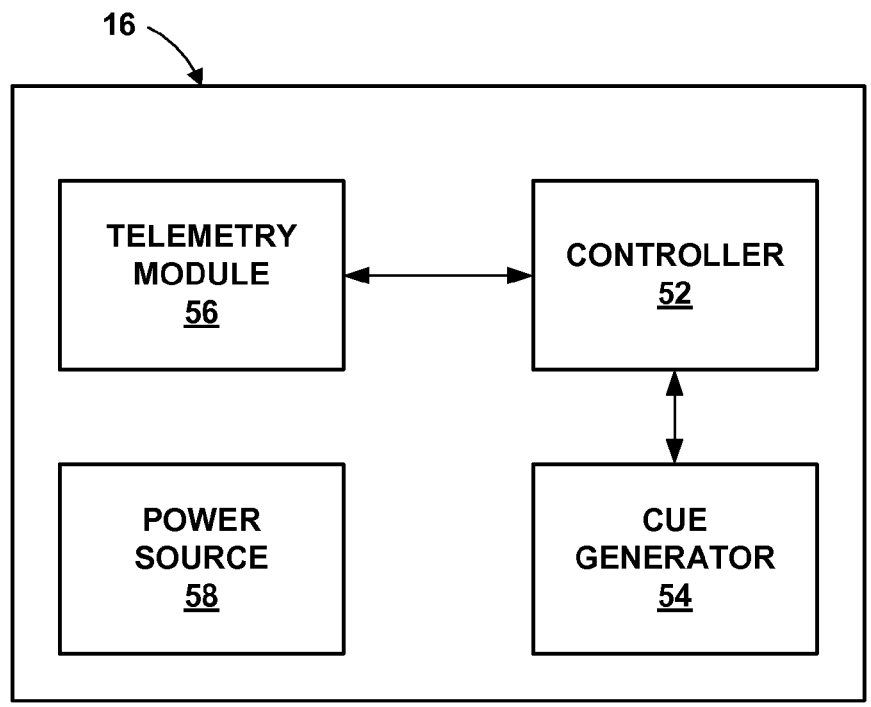
FIG. 4 is a block diagram illustrating various components of an example external cue device.

FIG. 4 is a block diagram illustrating various components of external cue device 16. External cue device 16 includes controller 52, cue generator 54, telemetry module 56, and power source 58. Power source 58 may be similar to power source 48 of sensing device 14, and provides power to components of external cue device 16. Cue generator 54 generates the external cue that is delivered to patient 12. In the case of a visual cue, for example, cue generator 54 may include a light source. In the case of an auditory cue, cue generator 54 may include components that generate a noise that is audible to patient 12. In the case of a somatosensory cue, cue generator 54 may include components that generate a vibration, cause external cue device 16 to noticeably change in temperature to patient 12 or another sensory experience by patient 12 (e.g., another tactile signal).

Controller 52 controls cue generator 54. For example, controller 52 may control the initiation of an external cue by cue generator 54. In some cases, controller 52 may also control the deactivation of the delivery of an external cue to patient 12. Controller 52 may include software executing on a processing device, hardware, firmware or combinations thereof. For example, controller 52 may comprise any one or more of a microprocessor, a controller, a DSP, an ASIC, a FPGA, discrete logic circuitry or the like. The functions attributed to controller 52 herein may be embodied as software, firmware, hardware or any combination thereof.

Controller 52 is configured to receive a control signal from sensing device 14 via telemetry module 56 (which may include a wired or wireless connection to telemetry module 44 of sensing device 14), which includes the receiver 22 (FIG. 1). Telemetry module 56 may comprise receiver 22 (FIG. 1A) or may otherwise be coupled to receiver 22. In some cases, controller 52 may also transmit signals to another device, e.g., programmer 38, via telemetry module 56. For example, if power source 58 has a low level of remaining power, controller 52 may alert patient 12 by sending a signal to programmer 38. Other types of alerts are also contemplated, such as a visible alert or an audible alert that differs from the visual or auditory cue. In addition, controller 52 may also send a signal to programmer 38 or sensing device 14 each time an external cue is delivered to patient 12, and programmer 38 or sensing device 14 may record the signal in the respective memory. Alternatively or in addition to storing data within a memory of programmer 38 or sensing device 14, external cue device 16 may include a memory.

Figure 5:
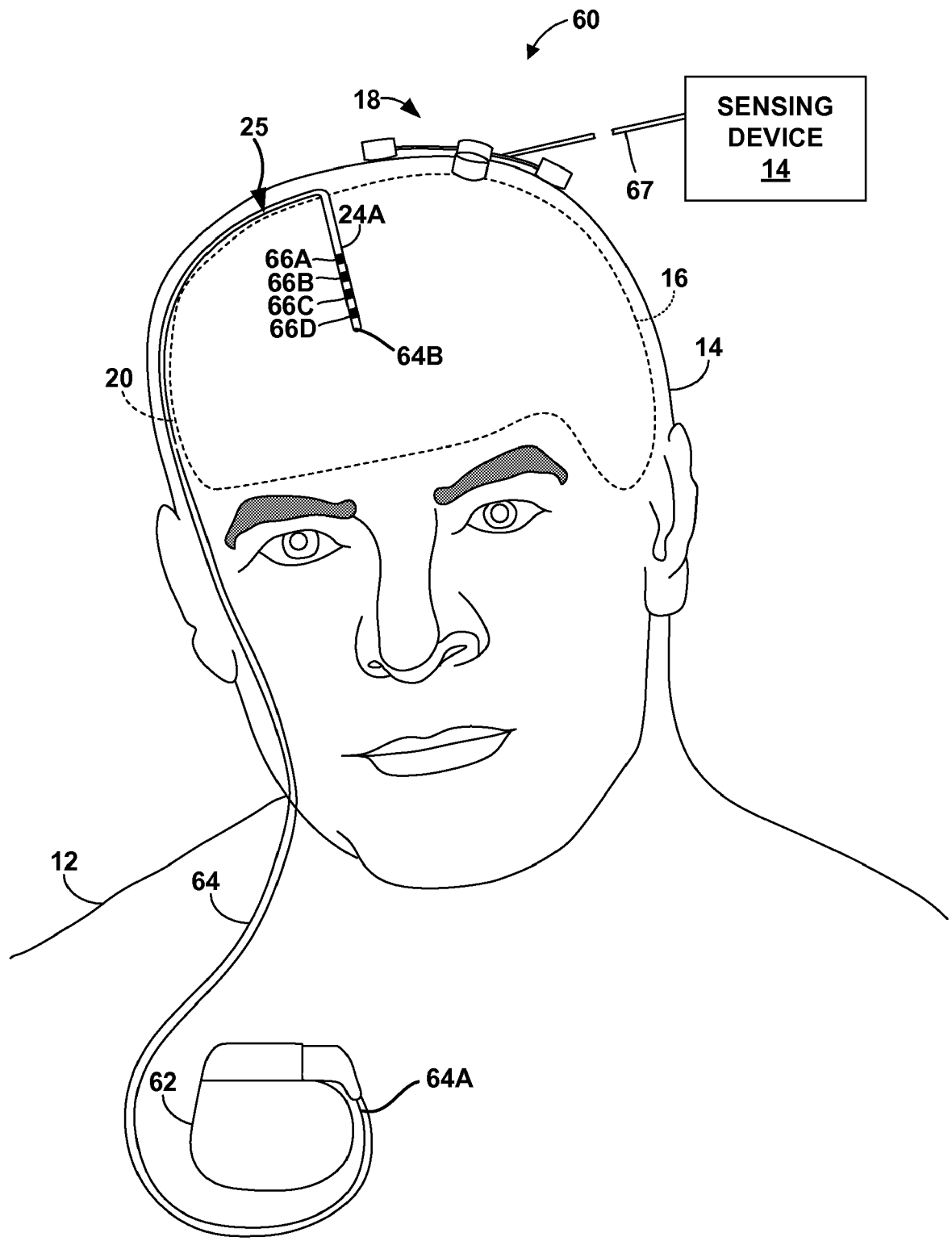
FIG. 5 is a schematic diagram of another example therapy system, which includes an external sensing device and an implanted therapy delivery device.

FIG. 5 is a conceptual diagram of another example therapy system 60, which includes external sensing device 14 that communicates with IMD 62. Rather than delivering an external cue to patient 12 upon detecting patient 12 is in a movement state, therapy system 60 delivers stimulation therapy to patient 12. In the example shown in FIG. 5, IMD 62 delivers electrical stimulation therapy to a stimulation site within brain 20 in order to help mitigate the symptoms of movement disorders. The target stimulation site within brain 20 which may depend upon the physiological condition that is being addressed by the electrical stimulation therapy. For example, suitable target therapy delivery sites within brain 20 for controlling a movement disorder of patient 12 include the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, and/or the Field of Forel (thalamic fasciculus). The PPN may also be referred to as the pedunculopontine tegmental nucleus. However, the target therapy delivery site may depend upon the patient disorder or condition being treated.

Electrical stimulation is delivered from IMD 62 to brain 20 by electrodes 66A-66D, which are carried by implantable medical lead 64. Lead 64 may be any suitable type of lead, such as a paddle lead or a lead having a cylindrical shaped body. At least some of the electrodes 66A-66D may comprise ring electrodes. In other examples, at least some of the electrodes 66A-66D may comprise segmented or partial ring electrodes, each of which extends along an arc less than 360 degrees (e.g., 90-120 degrees) around the outer circumference of lead 64. The configuration, type, and number of electrodes 66A-66D illustrated in FIG. 5 are merely exemplary. Although four electrodes 66A-66D are shown, lead 64 may carry any suitable number of electrodes in other examples, such as, but not limited to, two electrodes, six electrodes or eight electrodes. In addition, in some examples, multiple leads may be coupled to IMD 62 to deliver stimulation therapy to patient 12.

IMD 62 may deliver stimulation therapy to patient 12 according to one or more therapy parameter values. The values for the therapy parameters may be organized into a group of parameter values referred to as a "therapy program" or "therapy parameter set." "Therapy program" and "therapy parameter set" are used interchangeably herein. In the case of electrical stimulation, the therapy parameters may include an electrode combination, and an amplitude, which may be a current or voltage amplitude, and, if IMD 62 delivers electrical pulses, a pulse width, and a pulse rate for stimulation signals to be delivered to the patient. An electrode combination may include a selected subset of one or more electrodes 66A-66D. The electrode combination may also refer to the polarities of the electrodes in the selected subset. By selecting particular electrode combinations, a clinician may target particular anatomic structures within brain 20 of patient 12. In some cases, IMD 62 may deliver stimulation to patient 14 according to a program group that includes more than one therapy program. The stimulation signals according to the different therapy programs in a therapy group may be delivered on a time-interleaved basis or substantially simultaneously.

In one example, IMD 62 delivers electrical stimulation to a brain stem of patient 12, where the stimulation parameter values include a voltage amplitude of about 4 volts, a frequency of about 100 Hz, and a pulse rate of about 200 microseconds (μs). However, other stimulation parameter values may be useful, depending on the particular target stimulation site within patient 12. For example, an example range of electrical stimulation parameter values likely to be effective in deep brain stimulation, for example, are listed below.

1. Frequency: between approximately 0.5 Hz and approximately 500 Hz, such as between approximately 5 Hz and 250 Hz, or between approximately 70 Hz and approximately 120 Hz.

2. Amplitude: between approximately 0.1 volts and approximately 50 volts, such as between approximately 0.5 volts and approximately 20 volts, or approximately 5 volts. In other examples, a current amplitude may be defined as the biological load in the voltage is delivered.

3. Pulse Width: between approximately 10 microseconds and approximately 5000 microseconds, such as between approximately 100 microseconds and approximately 1000 microseconds, or between approximately 180 microseconds and approximately 450 microseconds.

Other ranges of therapy parameter values may be used when the therapy is directed to other tissues. While stimulation pulses are described, stimulation signals may be of any forms such as sine waves or the like.

An example range of electrical stimulation parameter values likely to be effective in treating chronic pain, e.g., when IMD 62 is configured to deliver spinal cord stimulation, is provided below. Again, while stimulation pulses are described, stimulation signals may be of any forms such as sine waves or the like.

1. Frequency: between approximately 0.5 Hz and approximately 500 Hz, such as between approximately 5 Hz and approximately 250 Hz, or between approximately 10 Hz and approximately 50 Hz.

2. Amplitude: between approximately 0.1 volts and approximately 50 volts, such as between approximately 0.5 volts and 20 volts, such as about 5 volts. In other examples, a current amplitude may be defined as the biological load in the voltage is delivered.

3. Pulse Width: between approximately 10 microseconds and approximately 5000 microseconds, such as between approximately 100 microseconds and approximately 1000 microseconds, or between approximately 180 microseconds and approximately 450 microseconds.

A proximal end of lead 64 may be directly or indirectly electrically and mechanically coupled to a connector block of IMD 62. In particular, conductors disposed within a lead body of lead 64 electrically connects stimulation electrodes 66A-66D located adjacent to distal end 64B of lead 64 to IMD 62. In other examples, multiple leads may be attached to IMD 62. In the example shown in FIG. 5, IMD 62 is an electrical stimulator implanted within patient 12. For example, IMD 62 may be subcutaneously implanted in the body of patient 12 (e.g., in a chest cavity, lower back, lower abdomen, buttocks or brain 20 of patient 12). IMD 62 provides a programmable stimulation signal (e.g., in the form of electrical pulses or substantially continuous-time signals) that is delivered to a target stimulation site within brain 20 by one or more stimulation electrodes 66A-66D carried by implantable medical lead 64. The stimulation administered by IMD 62 to brain 20 may be selected based on the specific movement disorder that is to be controlled by therapy system 60 and the effect of the stimulation on other parts of brain 20.

Lead 64 may be implanted within brain 20 or another target stimulation site within brain 20 of patient 12 via any suitable technique. In the example shown in FIG. 5, lead 64 is implanted through a cranium of patient 12. For example, in one example, lead 64 may be surgically implanted through a burr hole in a skull of patient 12, where lead 64 extends between IMD 62 and target site within brain 20 through the skull and scalp. Alternatively, lead 64 may be surgically implanted through a burr hole in the skull and routed through subcutaneous tissue to IMD 62. In other examples, therapy system 60 may include an external stimulator that is coupled to percutaneous leads that are implanted within patient 12.

Sensing device 14 may monitor an EEG signal via external sensing electrode array 18 and process the signals to determine if the signals indicate patient 12 is in a movement state. In the example shown in FIG. 5, sensing device 14 is coupled to external electrode array 18 via external lead 67. In other examples, sensing device 14 may be wirelessly coupled to external electrode array 18. Upon detecting an EEG signal indicative of prospective movement, sensing device 14 may provide an input to IMD 62 via wireless telemetry, such as with RF communication techniques. In response to receiving the input from sensing device 14, IMD 62 may control therapy delivery to patient 12, such as initiating the delivery of electrical stimulation to patient 12 or adjusting one or more stimulation parameter values. Stimulation therapy may be delivered to patient 12 according to a therapy program, which defines one or more stimulation parameter values.

In this way, sensing device 14 and IMD 62 define a responsive therapy system for providing on demand stimulation or stimulation adjustment to patient 12. Providing stimulation on demand, when movement-specific activation is desired, may be more beneficial to patient 12 than providing continuous or substantially continuous stimulation to patient 12. In some cases, continuous or substantially continuous delivery of stimulation to the brain 20 may interfere with other brain functions, such as activity within subthalamic nucleus, as well as therapeutic deep brain stimulation in other basal ganglia sites. In addition, providing stimulation intermittently or upon the sensing of movement by patient 12 may be a more efficient use of energy, particularly given finite battery power resources that may be used by IMD 62 or other components. Delivering movement order-related stimulation on demand, e.g., when patient 12 is in a movement state may help conserve the power source within IMD 62, which may be an important consideration with an implanted electrical stimulator.

It has also been found that patient 12 may adapt to deep brain stimulation provided by IMD 62 over time. That is, a certain level of electrical stimulation provided to brain 20 may be less effective over time. This phenomenon may be referred to as "adaptation." As a result, any beneficial effects to patient 12 from the deep brain stimulation may decrease over time. While the electrical stimulation levels (e.g., amplitude of the electrical stimulation signal) may be increased to overcome such adaptation, the increase in stimulation levels may consume more power, and may eventually reach undesirable or harmful levels of stimulation.

When stimulation is provided on demand, rather than continuously or substantially continuously, the rate at which patient adaptation to the therapy, whether electrical stimulation, drug delivery or otherwise, may occur may decrease. Similarly, when one or more stimulation parameter values (e.g., amplitude, voltage or frequency) are increased on demand, when a patient movement state is detected, both the rate at which patient 12 adapts to the stimulation therapy and the power consumed by IMD 62 may decrease as compared to continuous or substantially continuous stimulation at the elevated parameter values. Thus, therapy system 60 enables the therapy provided to patient 12 via IMD 62 to be more effective for a longer period of time as compared to systems in which therapy is delivered continuously or substantially continuously to patient 12. In addition, providing therapy on demand may help reduce the power requirements of IMD 62.

IMD 62 may also be configured to deliver stimulation to other regions within patient 12, in addition to or as an alternative to delivering stimulation to brain 20. As examples, IMD 62 may deliver electrical stimulation therapy to the spinal cord of patient 12, nerves, muscles or muscle groups of patient 12, or another suitable site within patient 12 in order to help patient 12 better control muscle movement. In some examples, after determining that an EEG signal indicates patient 12 in a movement state, sensing device 14 may provide input to IMD 62, which may initiate functional electrical stimulation (FES) or transcutaneous electrical stimulation (TENS) of a muscle or muscle group of patient 12 in order to help initiate movement or help patient 12 control movement of a limb or other body part. In the case of FES, IMD 62 may be implanted to deliver stimulation to a muscle, rather than the brain 20 of patient 12, as shown in FIG. 5. Alternatively, IMD 62 may take the form of one or more microstimulators implanted within a muscle of patient 12.

In other examples, IMD 62 may be configured to deliver a sensory cue to patient 12. For example, IMD 62 may deliver stimulation to a visual cortex of brain 20 of patient 12 in order to simulate an external visual cue. Stimulating the visual cortex may generate a visible signal to patient 12 that provides a substantially similar effect as an external visual cue. A sensory cue provided via IMD 62, however, may be more discreet than a sensory cue provided by external cue device 16.

In other examples, the EEG signal sensed by sensing device 14 may be used in a therapy system to control other types of therapy. For example, fluid (e.g., a drug) may be delivered to one or more regions of brain 20, the spinal cord, muscle, muscle group or another site within patient 12 in order to help patient 12 initiate muscle movement. As another example, a sensory cue may be delivered to patient via an external device or an implanted device to help patient 12 initiate muscle movement. In general, the delivery of electrical stimulation, drug therapy or sensory cue may help alleviate, and in some cases, eliminate symptoms associated with movement disorders. Furthermore, although external sensing device 14 is shown in FIG. 5, in other examples, therapy system 60 may include an implanted sensing device 32 and implanted electrode array 34, as shown in FIG. 2. In some examples, the implanted sensing device 32 and IMD 62 may be incorporated within a common housing and may, in some examples, share electrodes or leads that carry electrodes for sensing EEG signals and delivering electrical stimulation therapy to patient 12.

Figure 6:
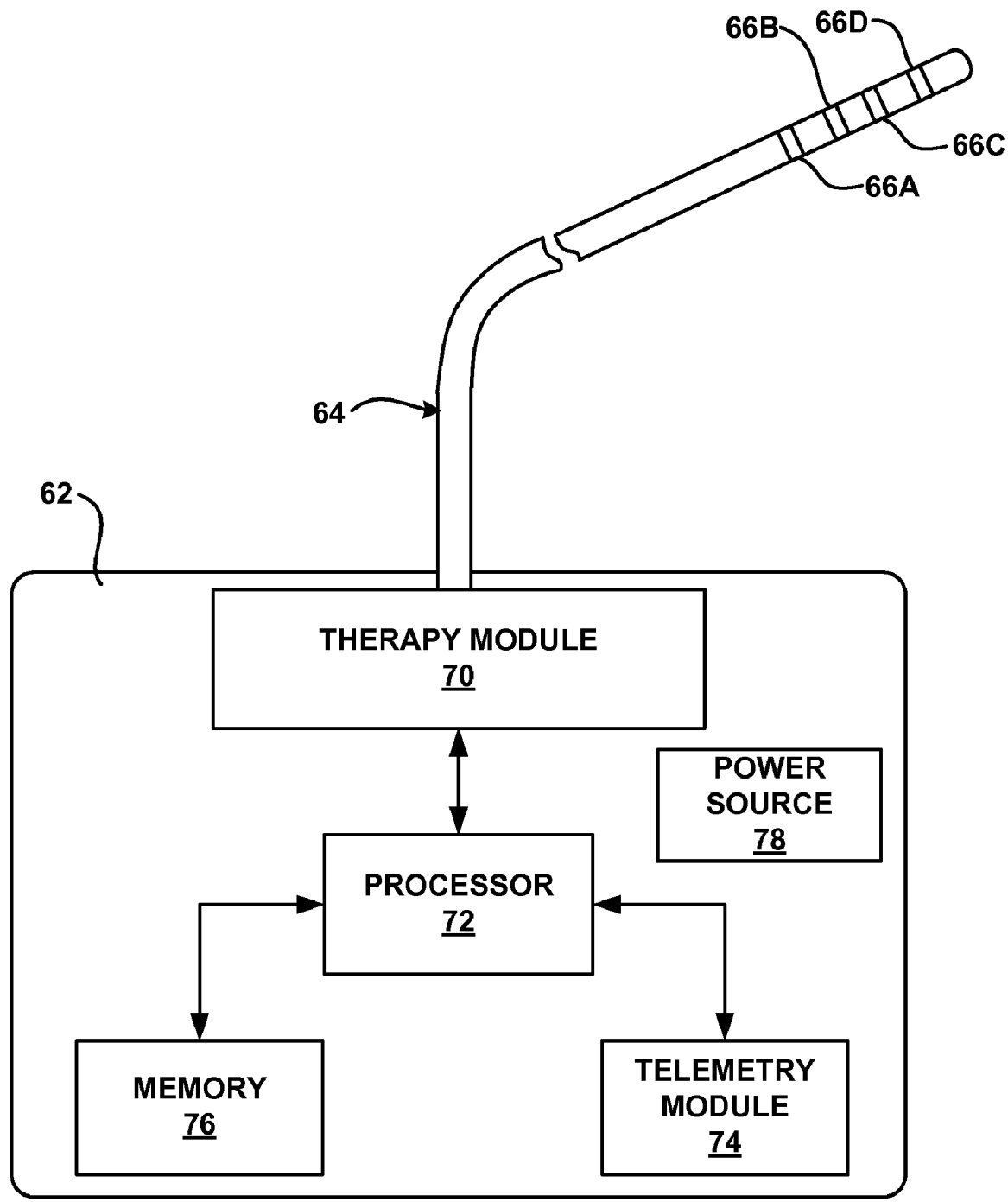
FIG. 6 is a block diagram illustrating various components of the implanted therapy delivery device of FIG. 5.

FIG. 6 is a block diagram illustrating various components of IMD 62 and an implantable medical lead 64 carrying one or more sense and/or stimulation electrodes. IMD 62 includes therapy delivery module 70, processor 72, telemetry module 74, memory 76, and power source 78. In some examples, IMD 62 may also include a sensing circuit (not shown in FIG. 2), e.g., for sensing brain signals (e.g., EEG or ECoG signals) or other physiological parameters of patient 12. Implantable medical lead 64 is coupled to therapy module 70 either directly or indirectly, e.g., via an extension. In particular, electrodes 66A-66D, which are disposed near a distal end of lead 64, are electrically coupled to a therapy delivery module 70 of IMD 62 via conductors within lead 64.

In one example, an implantable signal generator or other stimulation circuitry within therapy delivery module 70 generates and delivers electrical signals (e.g., pulses or substantially continuous-time signals, such as sinusoidal signals) to a target stimulation site within patient 12 via at least some of electrodes 66A-66D under the control of processor 72. The signals may be delivered from therapy delivery module 70 to electrodes 66A-66D via a switch matrix and conductors carried by lead 64 and electrically coupled to respective electrodes 66A-D. However, in some examples, electrodes 66A-66D may be independently activatable (e.g., stimulation may be selectively delivered to one or more electrodes 66A-66D at a time) without the aid of a switch matrix.

The implantable signal generator may be coupled to power source 78. Power source 78 may take the form of a small, rechargeable or non-rechargeable battery, or an inductive power interface that transcutaneously receives inductively coupled energy. In the case of a rechargeable battery, power source 78 similarly may include an inductive power interface for transcutaneous transfer of recharge power.

Processor 72 may include any one or more microprocessors, controllers, DSPs, ASICs, FPGAs, discrete logic circuitry, or the like. The functions attributed to processor 72 herein may be embodied as software, firmware, hardware or any combination thereof. Processor 72 controls the implantable signal generator within therapy delivery module 70 to deliver electrical stimulation therapy according to selected stimulation parameter values, which may be stored as a set of parameter values in a therapy program. Specifically, processor 72 may control therapy delivery module 70 to deliver electrical signals with selected amplitudes, pulse widths (if applicable), and rates specified by the therapy programs, which may be stored within memory 76. In addition, processor 72 may also control therapy delivery module 70 to deliver the stimulation signals via selected subsets of electrodes 66A-66D with selected polarities. For example, electrodes 66A-66D may be combined in various bipolar or multi-polar combinations to deliver stimulation energy to selected sites, such as nerve sites adjacent the spinal column or brain 20.

Processor 72 may also control therapy delivery module 70 to deliver each stimulation signal according to a different program, thereby interleaving programs to simultaneously treat different symptoms or provide a combined therapeutic effect. For example, in addition to treatment of one symptom, such as akinesia, IMD 62 may be configured to deliver stimulation therapy to treat other symptoms such as pain or incontinence.

Memory 76 of IMD 62 may include any volatile or non-volatile media, such as a RAM, ROM, NVRAM, EEPROM, flash memory, and the like. In some examples, memory 76 of IMD 62 may store multiple sets of stimulation parameter values that are available to be selected by patient 12 or clinician via programmer 38 (FIG. 3) for delivery of stimulation therapy. For example, memory 76 may store stimulation parameter values transmitted by programmer 38 (FIG. 1). Memory 76 also stores program instructions that, when executed by processor 72, cause IMD 62 to deliver neurostimulation therapy. Accordingly, computer-readable media storing instructions may be provided to cause processor 72 to provide functionality as described herein.

Processor 72 may also control telemetry module 74 to exchange information with an external programmer, such as programmer 38, and sensing device 14 or 32 (FIGS. 1 and 2) by wireless telemetry. For example, sensing device 14 may transmit a control signal to processor 72 upon detecting patient 12 is in a movement state, and, in response to receiving the control signal, processor 72 may control therapy module 70 to deliver stimulation to patient 12 or increase or otherwise adjust the electrical stimulation parameters (e.g., pulse width, pulse rate, amplitude, and so forth).

While FIGS. 5 and 6 relate to examples in which IMD 62 and sensing device 14 are disposed in separate housings, in other examples, IMD 62 and sensing device 14 may be incorporated into a common housing. For example, IMD 62 and sensing device 14 may be incorporated into a common housing that is implanted within patient 12 or a common housing that is carried external to patient 12. As one example, IMD 62 may be modified to include EEG sensing module 40 that is coupled to processor 72 of IMD 62, and processor 72 may be configured to detect a movement state from the EEG signal monitored by EEG sensing module 40. Furthermore, if IMD 62 and sensing device 14 are incorporated into a common housing, IMD 62 and sensing device 14 may share processors, memories, and so forth, as well as one or more leads that carry electrodes for sensing EEG signals and electrodes for delivering stimulation.

Figure 7:
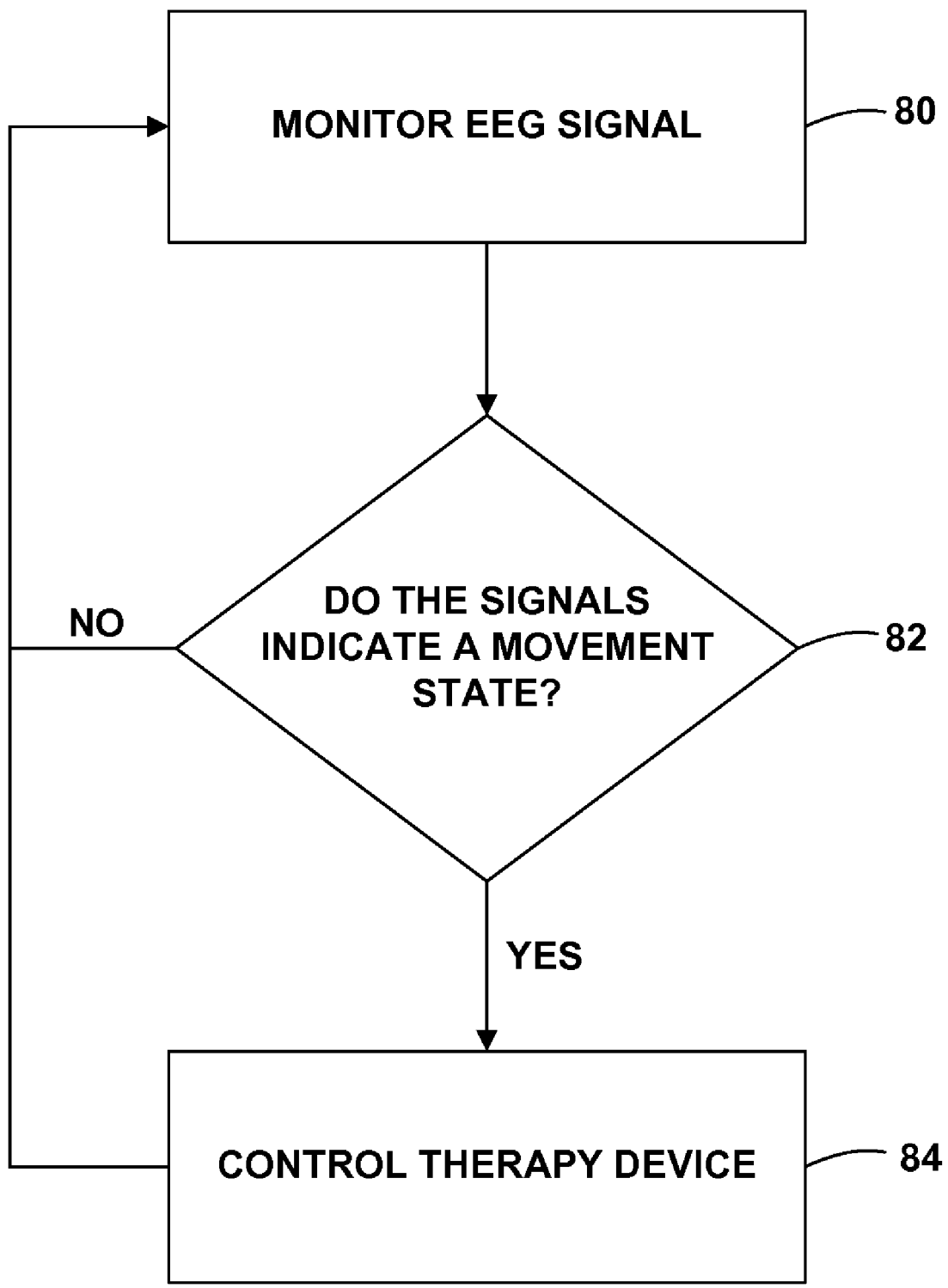
FIG. 7 is a flow diagram of an example technique for controlling a therapy device based on an electroencephalogram (EEG) signal.

FIG. 7 illustrates a flow diagram of a technique for controlling a therapy device, such as an external cue device 16 (FIG. 1) or IMD 62 (FIG. 5) based on an EEG signal. Sensing device 14 monitors the EEG signal within the motor cortex of brain 20 via surface electrode array 18 continuously or at regular intervals (80). In other examples, sensing device 14 may monitor the EEG signal within another part of brain 20. While external sensing device 14 is primarily referred to throughout the remainder of the application, the techniques described herein with respect to FIG. 7, as well as the other figures, may also be implemented by implanted sensing device 32. In addition, while EEG signals are primarily referred to with respect to the description of FIGS. 7-12, the movement state of patient 12 may also be detected based on other types of brain signals, such as a signal generated from measured field potentials within one or more regions of a patient's brain and/or action potentials from single cells within the patient's brain Processor 42 (FIG. 3) of sensing device 14 receives sensor signals from EEG sensing module 40 and processes the EEG signals to determine whether the EEG signals indicate patient 12 is in a movement state (82). A signal processor within processor 42 or sensing module 40 of sensing device 14 may determine whether the EEG signals are indicative of a movement state using any suitable technique, such as the techniques described above (e.g., voltage, amplitude, temporal correlation or frequency correlation with a template signal, or combinations thereof). If the EEG signals do not indicate a movement state, sensing module 40 may continue monitoring the EEG signal under the control of processor 42 (80). If the sensor signals indicate a movement state, processor 42 may control a therapy device (84). As previously discussed, the therapy device may be external cue device 16 shown in FIG. 1, an electrical stimulation device (e.g., IMD 62) or a fluid delivery device.

For example, in the case of external cue device 16, processor 42 of sensing device 14 may provide a signal to controller 52 of external cue device 16 via telemetry module 56, and controller 52 may cause cue generator 54 to generate and deliver a visual cue to patient 12. As another example, in the case of IMD 62 of FIGS. 5 and 6, upon processing the signals received from sensing module 40 and determining that patient 12 is in a movement state, processor 42 may provide a signal to processor 72 of IMD 62 via the respective telemetry modules 46 and 74. Processor 72 of IMD 62 may then initiate therapy delivery via therapy module 70 or adjust therapy (e.g., increase an intensity of therapy in order to help patient 12 initiate muscle movement).

In some examples of the therapy systems described herein, the therapy system may provide feedback to patient 12 to indicate that the movement state was detected and therapy was adjusted accordingly. For example, the sensory cortex of brain 16 may be stimulated to provide the sensation of a visible light. Other forms of sensory feedback are also possible, such as an audible sound or a somatosensory cue. In some examples, programmer 38 may include a feedback mechanism, such a LED, another display or a sound generator, which indicates that the therapy system received the volitional patient input and that the appropriate therapy adjustment action was taken. By learning which patient actions resulted in the movement state being detected and therapy being adjusted accordingly, patient 12 may learn to control the EEG signal to trigger therapy adjustment.

Figure 8:
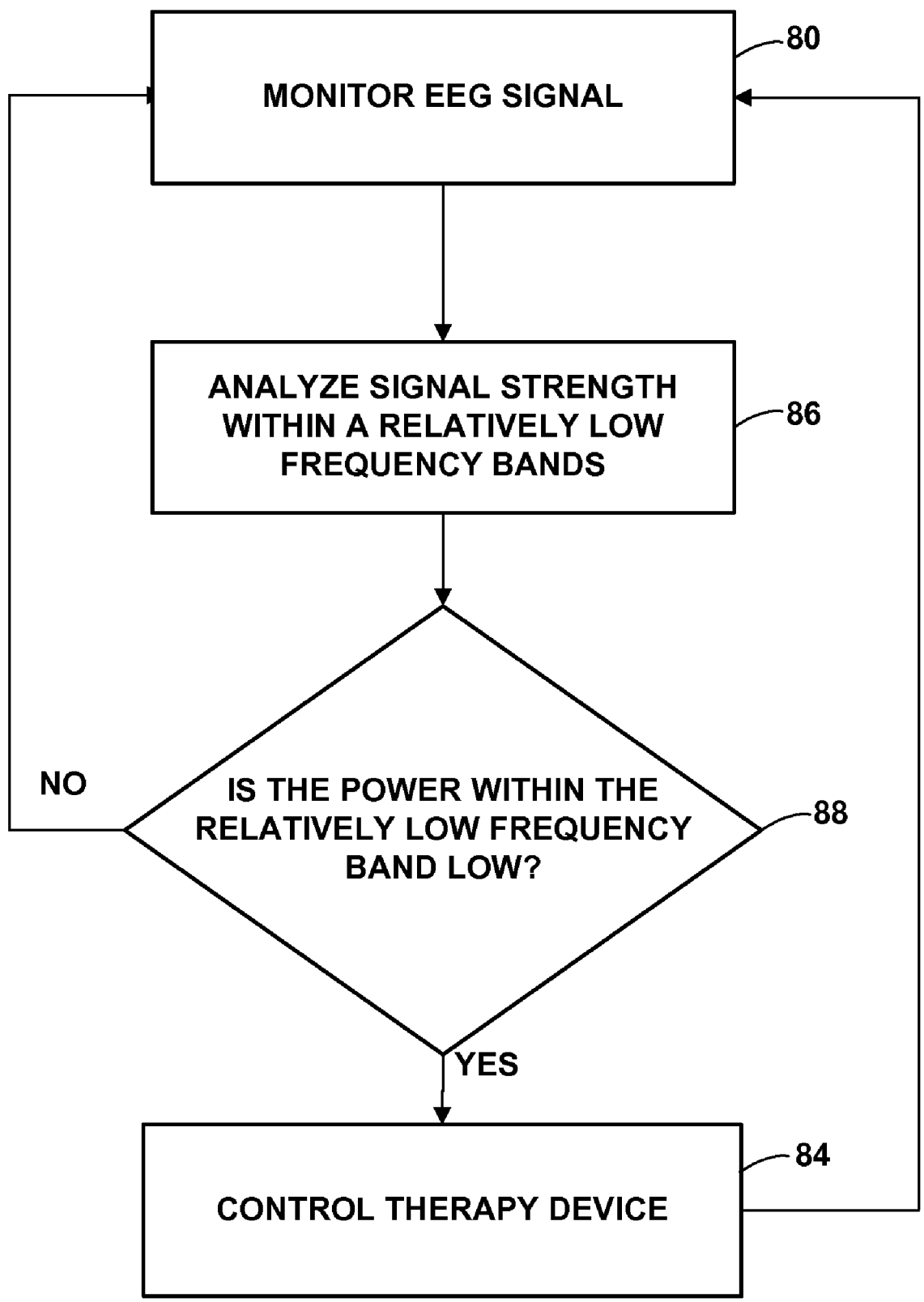
FIG. 8 is a flow diagram of an example technique for controlling a therapy device based on one or more frequency characteristics of an EEG signal.

FIG. 8 is a flow diagram of an example technique for controlling a therapy device based on one or more frequency characteristics of an EEG signal. Sensing device 14 monitors an EEG signal from the motor cortex of brain 20 of patient 12 via surface electrode array 18 (FIG. 1) (80). The discussion of FIG. 8 will primarily refer to sensing device 14. However, in other examples, IMD 32 (FIG. 2) may measure the EEG signal via an implanted electrode array 34 (FIG. 2).

A signal processor within processor 42 of sensing device 14 analyzes the strength of the monitored EEG signal within a relatively low frequency band (e.g., the alpha or delta frequency bands from Table 1 above) (86). If the power level (also referred to as "energy" or an indication of the signal strength) within the low frequency band is relatively low (88), the brain signals may indicate that the power level is ramping up to a higher frequency band (e.g., the beta or gamma frequency bands from Table 1 above) and patient 12 is in a movement state. That is, an EEG signal that includes a relatively low power level within a low frequency band may be indicative of the movement state of patient 12. The "low" power level may be determined during a trial stage, which is described with reference to FIG. 14. The power level within the low frequency band may be compared to a threshold value to determine whether the power level indicates patient 12 is in a movement state. A power level falling below the threshold value may indicate patient 12 is in a movement state.

Alternatively, processor 42 may perform a temporal analysis of the power within the low frequency band to determine whether the power within the low frequency band increased or decreased relatively quickly over time. A decrease in the power in the low frequency band over time may indicate patient 12 is entering a movement state because the power level is ramping up to a higher frequency band, which is associated with movement. In one example, processor 42 compares the strength of an EEG signal within the low frequency band to a mean signal strength of the EEG signal from a previous time span, such as about 5 seconds to about 20 seconds, in order to determine whether the power within the low frequency band increased or decreased relatively quickly over time.

In response to detecting the signal indicative of prospective movement, processor 42 may control a therapy device (84), such as external cue device 16 shown in FIG. 1, an electrical stimulation device or a fluid delivery device. On the other hand, if the power in the lower frequency band is relatively high, patient 12 may be in a rest state, and processor 42 may not take any action, while sensing module 40 may continue monitoring the EEG signal (80).

Rather than monitoring a power of a low frequency band, in some examples, sensing module 40 of sensing device 14 may monitor the power level within a high frequency band (e.g., gamma or beta bands), and an increased power level in the high frequency band may indicate patient 12 is in a movement state. In general, if the strong (i.e., relatively high power) signals fall within a high frequency band (e.g., the beta or gamma bands from Table 1), or otherwise do not fall within the lower frequency band, processor 42 may generate a control signal to activate or otherwise control a therapy delivery device (84). As another alternative, sensing module 38 may monitor the power level within both the low and high frequency bands.

As another example, sensing module 40 may monitor both the power level within a low frequency band and a high frequency band. A correlation in the pattern of power levels within the low and high frequency bands may indicate patient 12 is in a movement state. For example, sensing module 40 may implement an algorithm that determines whether the power level within the low frequency band decreases, and, at substantially the same time or during a subsequent time period, determines whether the power level within the high frequency band decreases. The correlation or association of the trends in power level or power levels within more than one frequency band may help suppress false positives, i.e., false detections of the movement state, by providing two avenues for detecting the movement state of patient 12.

Figure 9:
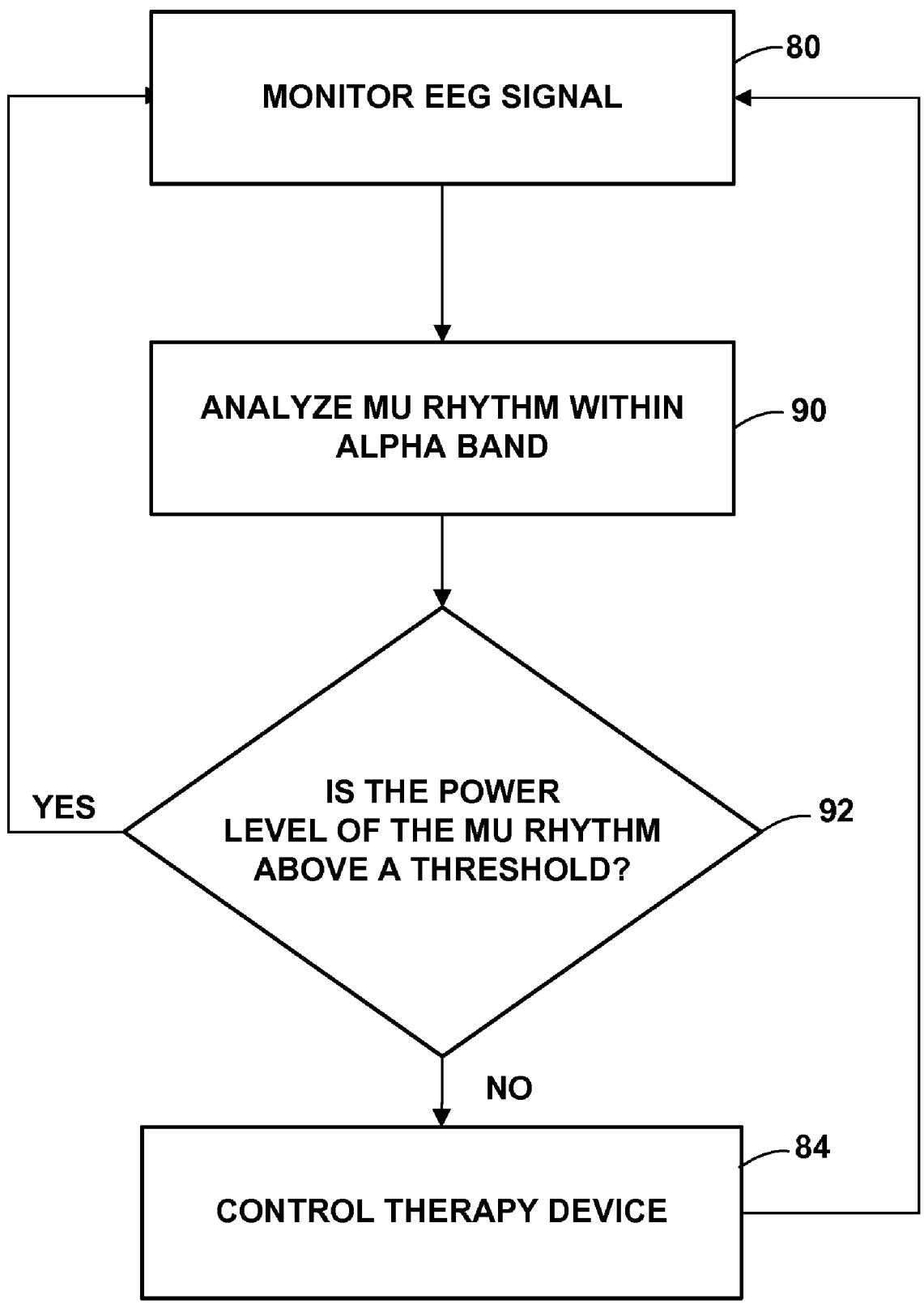
FIG. 9 is a flow diagram of another example of the technique shown in FIG. 8.

FIG. 9 is a flow diagram of another example of the technique shown in FIG. 8. Processor 42 of sensing device 14 may monitor the mu rhythm in the alpha band of the EEG signal from the motor cortex of brain 20 of patient 12 (80, 90). As previously described, a mu rhythm (or a mu wave) is a particular wave of electromagnetic oscillations in the alpha frequency band of an EEG signal. Processor 42 may analyze the power level of the mu rhythm in the alpha band. For example, processor 42 may determine whether the power level of the mu rhythm is above a threshold (92), which may be determined during a trial phase of the therapy system 10. If the power level of the mu rhythm is above the threshold, the EEG signal may indicate patient 12 is in a rest state. In some cases, when patient 12 is in a rest state, therapy is typically not necessary to help patient 12 initiate movement or otherwise control symptoms of a movement disorder. Thus, processor 42 may continue monitoring the mu rhythm in the alpha band of the EEG signal from the occipital cortex (80, 90). However, if the power level of the mu rhythm is below the threshold, the mu rhythm may indicate patient 12 is in a movement state, and processor 84 may control a therapy device (84).

In each of the examples described above in which processor 42 of sensing device 14 provides a control signal that is transmitted to external cue device 16 or IMD 62 to initiate therapy delivery to patient 12 or otherwise adjust therapy delivery to patient 12 in response to detecting a movement state, the therapy delivery may be initiated or delivered at adjusted therapy parameter values for a predetermined amount of time or until processor 42 receives an indication that patient 12 has successfully initiated movement or has stopped moving, depending upon the type of movement disorder that is treated. For example, if therapy system 10 is used to control akinesia, the therapy may be deactivated after patient 12 has successfully initiated movement or after a predetermined amount of time.

The predetermined amount of time may be selected to be sufficient to initiate patient movement or otherwise gain control of muscle movement. For example, if initiation of patient movement is desired, the predetermined amount of time may be relatively short (e.g., less than five seconds). On the other hand, if therapy system 10 is used to control gait freeze, which may occur at many possible points during a movement state, the therapy may be deactivated after patient 12 has stopped moving, i.e., has entered a rest state. In the case of a movement disorder, it may be useful to deliver therapy to patient 12 for a defined period of time, rather than substantially continuously, in order to help patient 12 initiate movement, while conserving the power source 58 of external cue device 16 or power source 78 of IMD 62. As described in further detail below, a motion sensor may be used to determine when therapy should be deactivated or otherwise adjusted. The motion sensor may indicate, for example, that patient 12 has successfully initiated movement or is in a rest state.

In some therapy systems, therapy parameter values may be modified depending upon the type of movement that patient 12 is intending on initiating. For example, if patient 12 is afflicted with tremor, and stimulation therapy is provided to patient 12 to help alleviate the tremor, a greater amplitude or pulse rate of stimulation frequency may be delivered if patient 12 is intending on performing a task that requires better control of movement (e.g., signing his name on a piece of paper with a pen) compared to when patient 12 is performing a task that requires less control of movement (e.g., intending on reaching for an object with his arm). That is, because more precise movement and dexterity may be required for holding a pen and writing compared to reaching for an object, the stimulation therapy parameter values (e.g., pulse amplitude, pulse rate, electrode configuration, and so forth) necessary to reduce the tremor for those two actions may differ. Similarly, in the case of a sensory cue, a different sensory cue may be more useful to patient 12 if patient 12 is intending on walking compared to when patient 12 is intending on lifting his arm.

Accordingly, in some examples, therapy parameter values may be selected, i.e., therapy may be "titrated" depending on the type of movement that patient 12 intends on undertaking or is actually undertaking. Sensing device 14, external cue generator 16 or IMD 62 may store a plurality of therapy programs, which define a set of therapy parameter values, for different types of movement. The types of movement may be distinguished on the level of activity, which may be reflected by the intensity level of certain frequency band components of the EEG signal.

Figure 10:
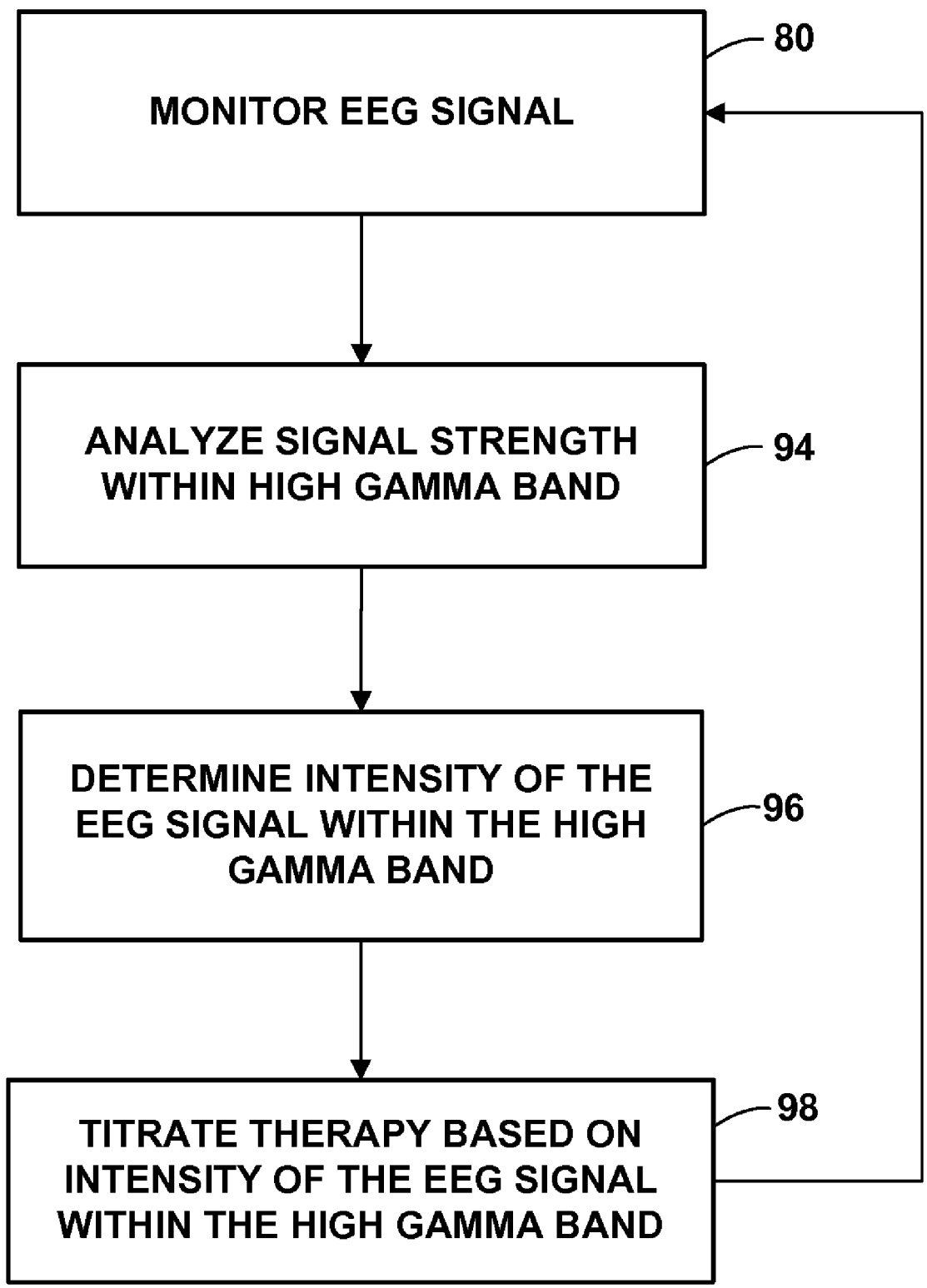
FIG. 10 is a flow diagram of an example technique for titrating therapy based on the strength of an EEG signal within a particular frequency band.

FIG. 10 is a flow diagram of an example technique that may be employed to titrate therapy based on the strength of an EEG signal within a particular frequency band, which may indicate the type of movement patient 12 intends on undertaking or is actually undertaking. While the high gamma band (e.g., between about 100 Hz to about 200 Hz) is primarily referred to in the description of FIG. 10, in other examples, other frequency bands that are revealing of the patient's intention to move may also be implemented in the technique shown in FIG. 10.

Sensing device 14 monitors an EEG signal of brain 20 of patient 12 (80), and processor 42 of sensing device 14 extracts the high gamma band component of the EEG signal in order to analyze the signal strength within the high gamma band (94). In some examples, sensing device 14 may filter out the high gamma band component of the EEG signal prior to transmitting the brain signal to processor 42. Processor 42 may determine the intensity (or strength) of the EEG signal within the high gamma band (96). Based on the intensity within the high gamma band, processor 42 may determine what type of motion patient 12 is intending on initiating, and titrate therapy accordingly (98).

The intensity within the high gamma band or within another frequency band may be associated with a particular motion or degree of motion (e.g., relative levels of activeness or precision) during a trial stage. For example, during a trial stage, sensing device 14 may monitor the EEG signal that is generated when patient 12 initiates a variety of different movements, such as movement of an arm, finger, leg, and so forth. Based on the EEG signal associated with each movement, a clinician, with the aid of a computing device, may associate a movement with the intensity level within the high gamma band at the time patient 12 initiated the thoughts directed to initiating the respective movement. The high gamma band intensity level and the associated movement may be recorded in memory 46 of sensing device 14.

Figure 11:
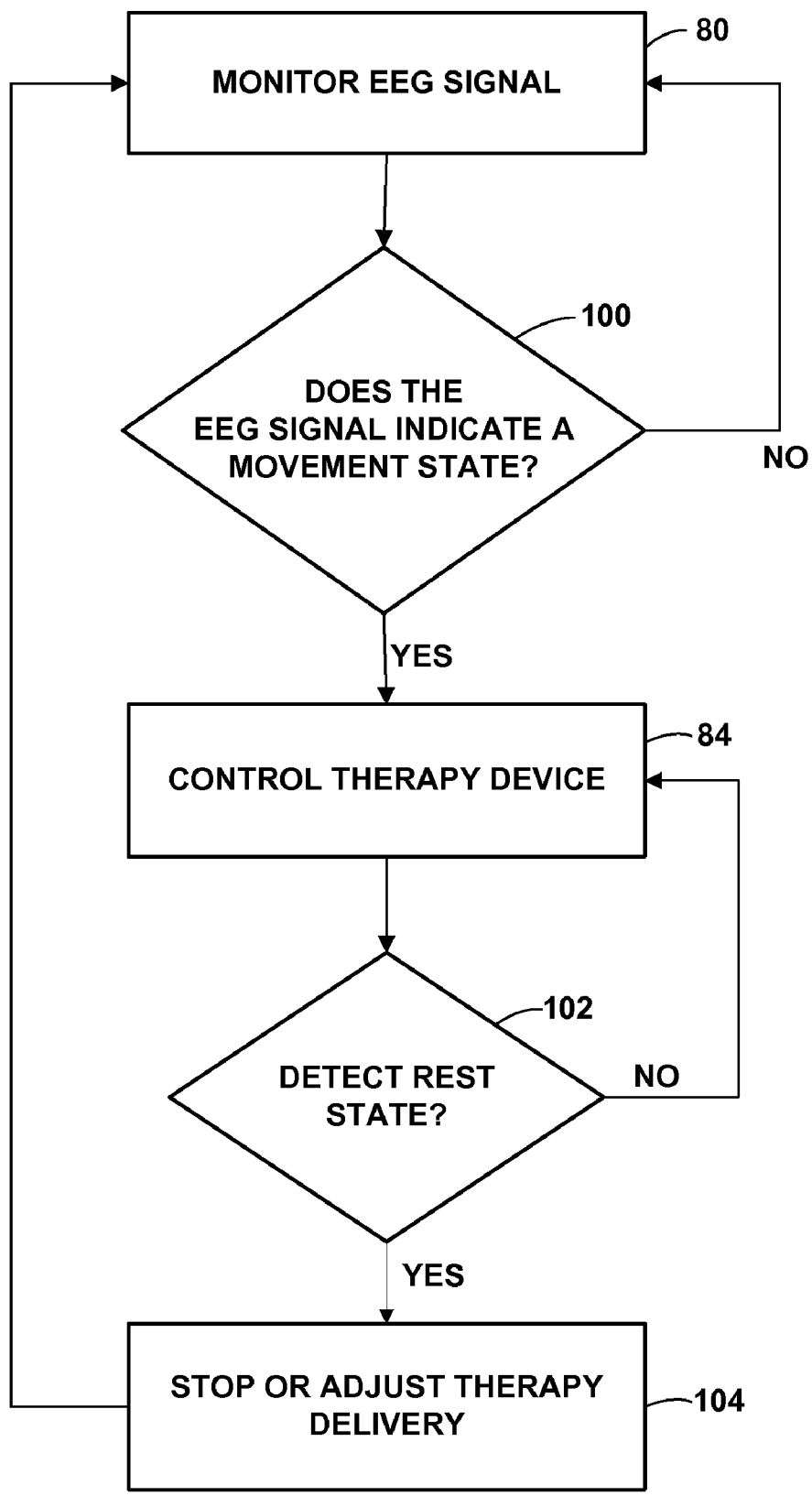
FIG. 11 is a flow diagram of an example technique for deactivating or adjusting therapy delivery in response to detecting a cessation of movement or a successfully initiation of movement.

FIG. 11 is a flow diagram of an example technique for deactivating or adjusting therapy delivery in response to detecting patient 12 has stopped moving or has successfully initiated movement. Processor 42 of sensing device 14 may monitor the EEG signal from the relevant region of the patient's brain 20, which may depend upon the type of movement being detected (80). Processor 42 may determine whether the EEG signal indicates patient 12 is in a movement state (100) using any of the techniques described above. Upon determining patient 12 is in a movement state, processor 42 may control therapy device (84). For example, processor 42 may generate a control signal that activates therapy delivery or adjusts therapy delivery.

Processor 42 may then determine whether patient 12 in a rest state (102). In other examples, processor 42 may be configured to decrease the intensity of therapy (e.g., the voltage or current amplitude of electrical stimulation, the frequency of electrical stimulation, the bolus size of a drug, the frequency of the bolus delivery, and the like) or stop therapy upon the detection of the successful initiation of patient movement. An indication that patient 12 has initiated movement or stopped moving (e.g., is in a rest state) may be generated any suitable way. In some examples, processor 42 may determine whether patient 12 is no longer in the movement state (i.e., is in the rest state) based on a signal that is independent of brain signals. As described in further detail below, the rest state or the initiation of movement may be detected via any suitable technique, such as by detecting gross movement from a motion sensor (e.g., an accelerometer) or based on the EEG signals. If the rest state is not detected, processor 42 may continue controlling the therapy device (84). However, if the rest state is detected, processor 42 may generate a control signal to stop or adjust the delivery of therapy (104).

In other examples, processor 42 may monitor the EEG signals to determine whether the EEG signals indicate patient 12 is in a rest state. In the case of a mu rhythm, for example, processor 42 may determine whether the power level of the mu rhythm exceeds the threshold, which may indicate patient 12 is in a rest state. If the therapy delivery is deactivated upon detecting patient 12 has successfully initiated movement, processor 42 may monitor the EEG signal and analyze the signal to determine whether patient 12 is still in a movement state a predetermined amount of time after the initiation of the movement state was detected, such as about 10 seconds to about two minutes. The period of time for detecting the initiation of movement should be selected to provide patient 12 with enough time to actually initiate movement.

In some examples, processor 42 of sensing device 14 (or processor 72 of IMD 62 or controller 52 of external cue device 16) may initially control therapy delivery to patient 12, e.g., initiate therapy delivery or adjust therapy parameter values, based on an EEG signal (or other brain signal) sensed by sensing device 14. Processor 42 may then make longer term adjustments to therapy based on signals from another sensor, such as a motion sensor. That is, upon determining that patient 12 is in a movement state based on EEG signals or other brain signals, processor 42 may subsequently determine whether patient 12 is still in the movement state, and, in some examples, the relative activity level of patient 12, to provide further control of therapy. The long term therapy adjustments may include, for example, continuing therapy delivery to patient 12 based on signals from a sensor that may indicate patient movement independently of any EEG signals monitored by sensing device 14, deactivating therapy delivery to patient 12, or modifying one or more therapy parameter values of the therapy that is currently being delivered to patient 12. In addition, by determining whether patient 12 is in a movement state after the movement state is detected based on the EEG signals, processor 42 may confirm that the movement state was properly detected.

Figure 12:
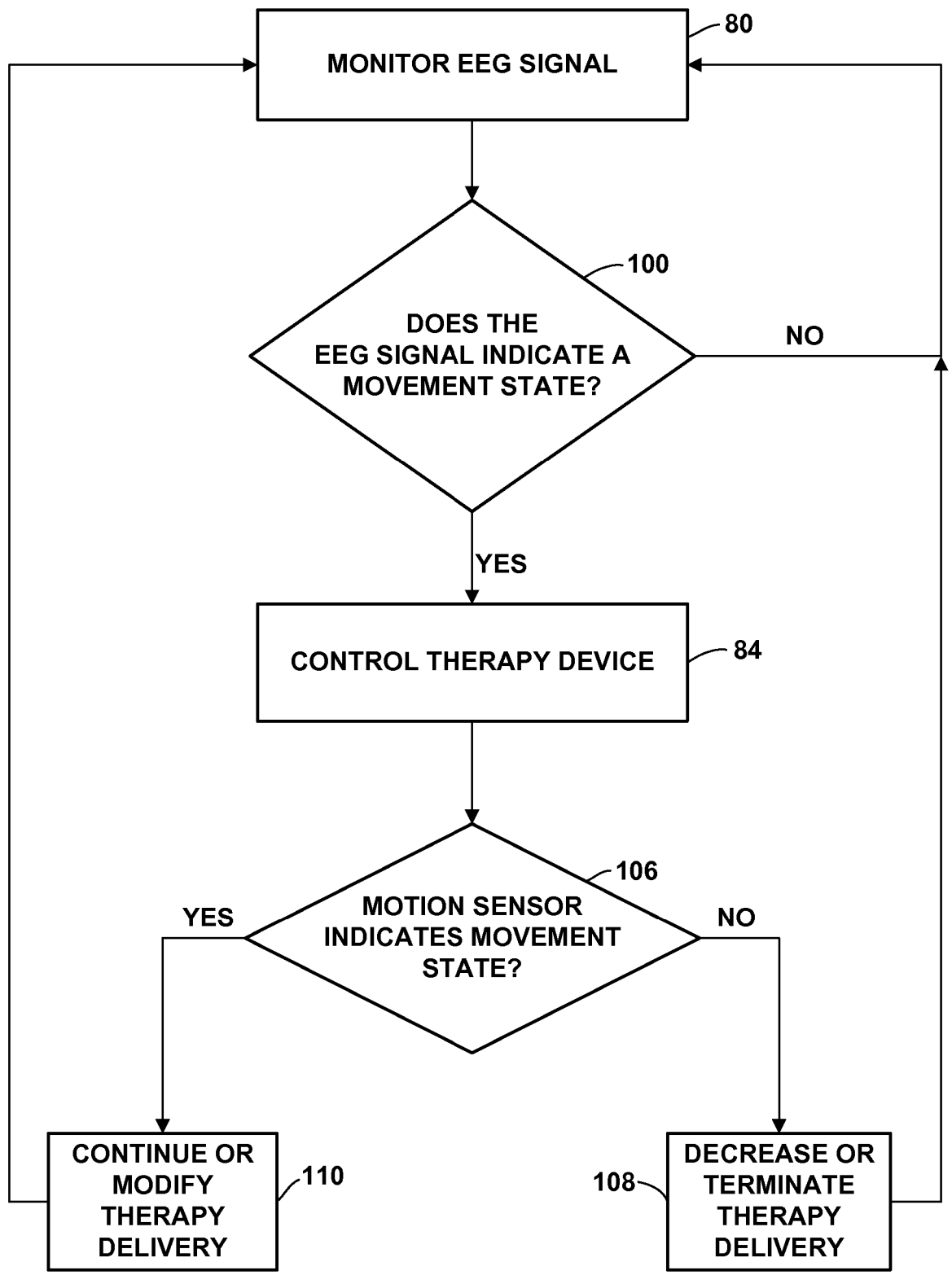
FIG. 12 is a flow diagram of an example technique for controlling a therapy device based on an EEG signal and a signal from a motion sensor.

FIG. 12 is a flow diagram of an example technique that may be implemented to control a therapy device in response to detecting patient 12 is in a movement state based on an EEG signal (or other bioelectrical brain signal) from sensing device 14 and a signal from a motion sensor. As with FIGS. 7-11, although FIG. 12 is described with respect to processor 42 of sensing device 14, in other examples, a processor of another device, such as external cue device 16, IMD 62 or implanted sensing device 32, may perform any part of the technique shown in FIG. 12.

Processor 42 of sensing device 14 may monitor the EEG signal from the relevant region of the patient's brain 20, which may depend upon the type of movement being detected (80). Processor 42 may determine whether the EEG signal indicates patient 12 is in a movement state (100) using any of the techniques described above. Upon determining patient 12 is in a movement state, processor 42 may control a therapy device (84), such as by generating a control signal that activates therapy delivery or adjusts therapy delivery for the movement state.

Processor 42 may then reference a motion sensor to determine whether patient 12 is in a movement state (106). The motion sensor generates a signal indicative of patient motion that is independent of the EEG activity or other bioelectrical brain activity of patient 12. For example, processor 42 may determine the gross or relative activity level of patient 12 based on the output from an accelerometer. The motion sensor may generate electrical signals that change at least one signal characteristic (e.g., a signal amplitude or frequency) as a function of patient motion. In some examples, processor 42 may compare an electrical signal from the motion sensor to a baseline signal (e.g., a threshold value of the signal amplitude or a slope or other component of the signal) to determine whether the electrical signal indicates patient 12 is in a movement state. The baseline signal may comprise, for example, the baseline signal of the motion sensor when patient 12 is in a rest state. The baseline signal may be adjusted over time to account for changes in the baseline signal of the motion sensor when patient 12 is in a rest state. Accordingly, the baseline signal may not have a fixed characteristic (e.g., amplitude value).

The motion sensor may be positioned to detect movement of patient 12 and may be implanted within patient 12 or may be external to patient 12. Examples of motion sensors are described with respect to FIG. 13. If the motion sensor indicates patient 12 is not a movement state (106), processor 42 may decrease the intensity of therapy delivery (e.g., by switching to a different therapy program) or terminate therapy delivery (108), and continue monitoring the EEG signal (80). If the signal generated by the motion sensor indicates patient 12 is not in a movement state, processor 42 may determine that the detection of the motion state based on the EEG signal was a false positive, and, accordingly, therapy delivery to help patient 12 initiate or maintain motion may not be necessary.

If the motion sensor indicates patient 12 is in a movement state (106), processor 42 may continue therapy delivery or modify therapy delivery (e.g., deliver therapy according to a different therapy program) (110). In some examples, processor 42 may switch therapy programs or otherwise adjust a therapy parameter value upon determining that patient 12 is still in the movement state following the initial determination of the movement state based on the EEG signal (100). For example, after determining patient 12 is in a movement state based on the EEG signals, processor 42 may generate a control signal that causes a therapy device to deliver therapy to patient 12 according to a first therapy program to help patient 12 initiate movement.

In some examples, upon determining that patient 12 is actually in a movement state based on the motion sensor (106), processor 42 may determine that patient 12 has successfully initiated movement, and, therefore, the first therapy program may no longer be as useful as another therapy program, such as therapy program that helps improve patient 12 gait or control of movement. Thus, upon determining that patient 12 is in a movement state based on the motion sensor (106), processor 42 may control a therapy device (e.g., by generating another control signal) to deliver therapy according to a second therapy program that is different than the first therapy program. Processor 42 may select the second therapy program using any suitable technique. In some examples, memory 46 of sensing device 14 or another device may store a plurality of therapy programs and associate each therapy program with an activity level, e.g., an electrical signal or a range of electrical signals generated by the motion sensor. Processor 42 may reference the stored therapy programs and select the therapy program that is best associated with the signal (or other input) received from the motion sensor. In this way, processor 42 may titrate therapy to patient 12 based on the relative activity level of patient 12.

In other examples, upon determining that patient 12 is in a movement state based on the motion sensor (106), processor 42 may control a therapy device (e.g., by generating another control signal) to continue delivering therapy according the first therapy program with which therapy was delivered following detection of the movement state based on the EEG signals.

In some examples, processor 42 may continue monitoring the EEG signals or motion sensor signals to determine whether patient 12 is in a movement state or whether patient is in a rest state. As described with respect to FIG. 11, in other examples, processor 42 may be configured to decrease an intensity of therapy (e.g., a frequency of therapy delivery or an amplitude or pulse width of an electrical stimulation signal in the case of stimulation therapy) or stop therapy upon the detection of the successful initiation of patient movement.

Confirming that patient 12 is in a movement state based on a signal other than the EEG signal, e.g., a motion sensor, may help prevent unnecessary delivery of therapy and may provide a more robust titration of therapy. For example, if patient 12 is intending to initiate movement, such that the EEG signals monitored by processor 42 indicate patient 12 is in a movement state, but patient 12 ultimately decides not to initiate movement, processor 42 may generate the control signal that activates therapy delivery or adjusts therapy delivery (84) although therapy may not be necessary to initiate or maintain movement. The motion sensor may help confirm that patient 12 followed through on an intent to move.

Processor 42 may reference the signal from the motion sensor to determine whether the motion sensor indicates patient 12 is in a movement state (106) at any suitable time. For example, processor 42 may reference the signal from the motion sensor within about 1 second to about 10 minutes after processor 42 determines patient 12 is in a movement state based on the EEG signal (100). In some examples, processor 42 may determine when to reference the signal from a motion sensor based on information provided by a predictive filter, such as a Kalman filter.

Figure 13:
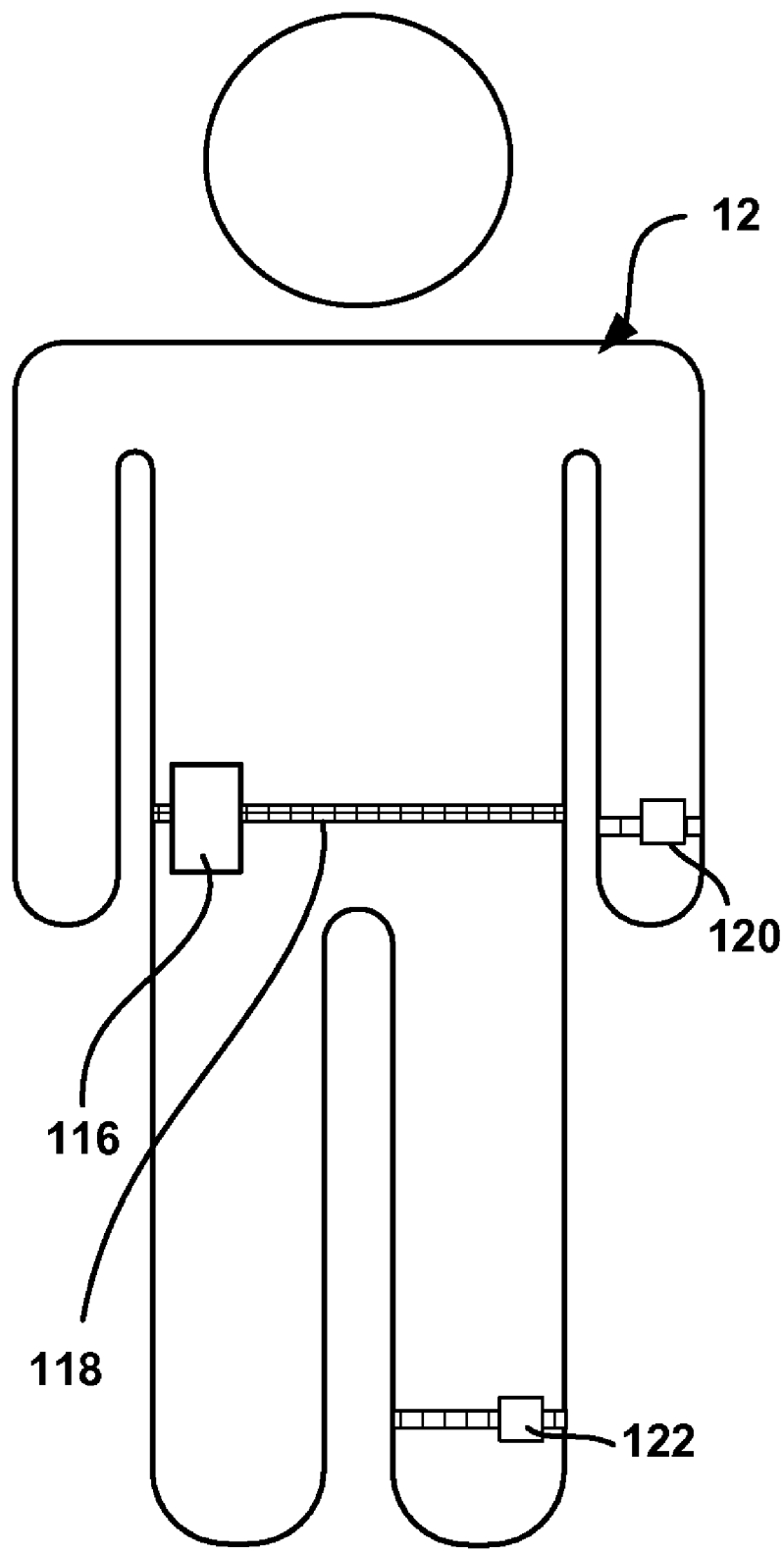
FIG. 13 is a schematic diagram illustrating example motion sensors that may be used to monitor an activity level of a patient to detect a movement state of a patient.

FIG. 13 is a schematic diagram illustrating motion sensor 116 that may be used to monitor an activity level of patient 12 to determine whether patient 12 has initiated movement, stopped moving, and/or to confirm that patient 12 is in a movement state. Processor 42 may monitor output from motion sensor 116 immediately after therapy is delivered to patient 12 or within a certain period of time after therapy is delivered, such as about 5 seconds to about 10 seconds or longer. Signals generated by motion sensor 116 may be sent to processor 42 of sensing device 14 via wireless signals or a wired connection, which may process the signals to determine whether patient 12 has initiated movement or stopped moving, and provide a control signal to external cue device 16 or IMD 62 to deactivate therapy or decrease therapy delivery parameters (e.g., stimulation amplitude, frequency, size of a drug bolus, etc.). Alternatively, the signals generated by motion sensor 116 may be sent directly to the therapy source, e.g., external cue device 16 or IMD 62 via wireless signals or a wired connection.

Motion sensor 116 is an external device that may be attached to patient 12 via a belt 118. Alternatively, motion sensor 116 may be attached to patient 12 by any other suitable technique, such as a clip that attaches to the patient's clothing, via a wristband, as shown with motion sensor 120 or via a band attached to the patient's leg, as shown with motion sensor 122. Motion sensors 116, 120, 122 may each include sensors that generate a signal indicative of patient motion, such as accelerometer or a piezoelectric crystal. Alternatively, a motion sensor may be integrated with sensing device 14, external cue device 16, IMD 32, or IMD 62 or implanted within patient 12.

In addition to or instead of a motion sensor, a sensor that generates a signal that indicates a physiological parameter that varies as a function of patient activity may be used to determine whether patient 12 has successfully initiated movement or has stopped moving, depending on the type of therapy deactivation signal desired. Suitable physiological parameters include heart rate, respiratory rate, electrocardiogram morphology, respiration rate, respiratory volume, core temperature, a muscular activity level, subcutaneous temperature or electromyographic activity of patient 12.

For example, in some examples, patient 12 may wear an ECG belt that incorporates a plurality of electrodes for sensing the electrical activity of the heart of patient 12. The heart rate and, in some examples, ECG morphology of patient 12 may monitored based on the signal provided by the ECG belt. Examples of suitable ECG belts for sensing the heart rate of patient 12 are the "M" and "F" heart rate monitor models commercially available from Polar Electro of Kempele, Finland. In some examples, instead of an ECG belt, patient 12 may wear a plurality of ECG electrodes (not shown in FIG. 11) attached, e.g., via adhesive patches, at various locations on the chest of patient 12, as is known in the art. An ECG signal derived from the signals sensed by such an array of electrodes may enable both heart rate and ECG morphology monitoring, as is known in the art.

As another example, patient movement may be detected via a respiration belt, such as a plethysmograpy belt, that outputs a signal that varies as a function of respiration of the patient. An example of a suitable respiration belt is the TSD201 Respiratory Effort Transducer commercially available from Biopac Systems, Inc of Goleta, Calif. Alternatively, a plurality of electrodes that direct an electrical signal through the thorax of patient 12, and circuitry to sense the impedance of the thorax, which varies as a function of respiration of patient 12, may used to detect a patient activity level, which indicates whether patient 12 is in a movement state. In other examples, an indication that patient 12 has initiated movement or stopped moving may be generated in other ways.

As previously described, processor 42 may determine whether an EEG signal indicates patient 12 is in a rest state or a movement state by voltage, amplitude, temporal correlation or frequency correlation with a template signal, monitoring the power level within a particular frequency band of the EEG signal, or combinations thereof. The EEG signal characteristic that indicates patient 12 is in a rest state or a movement state may differ between patients.

Figure 14:
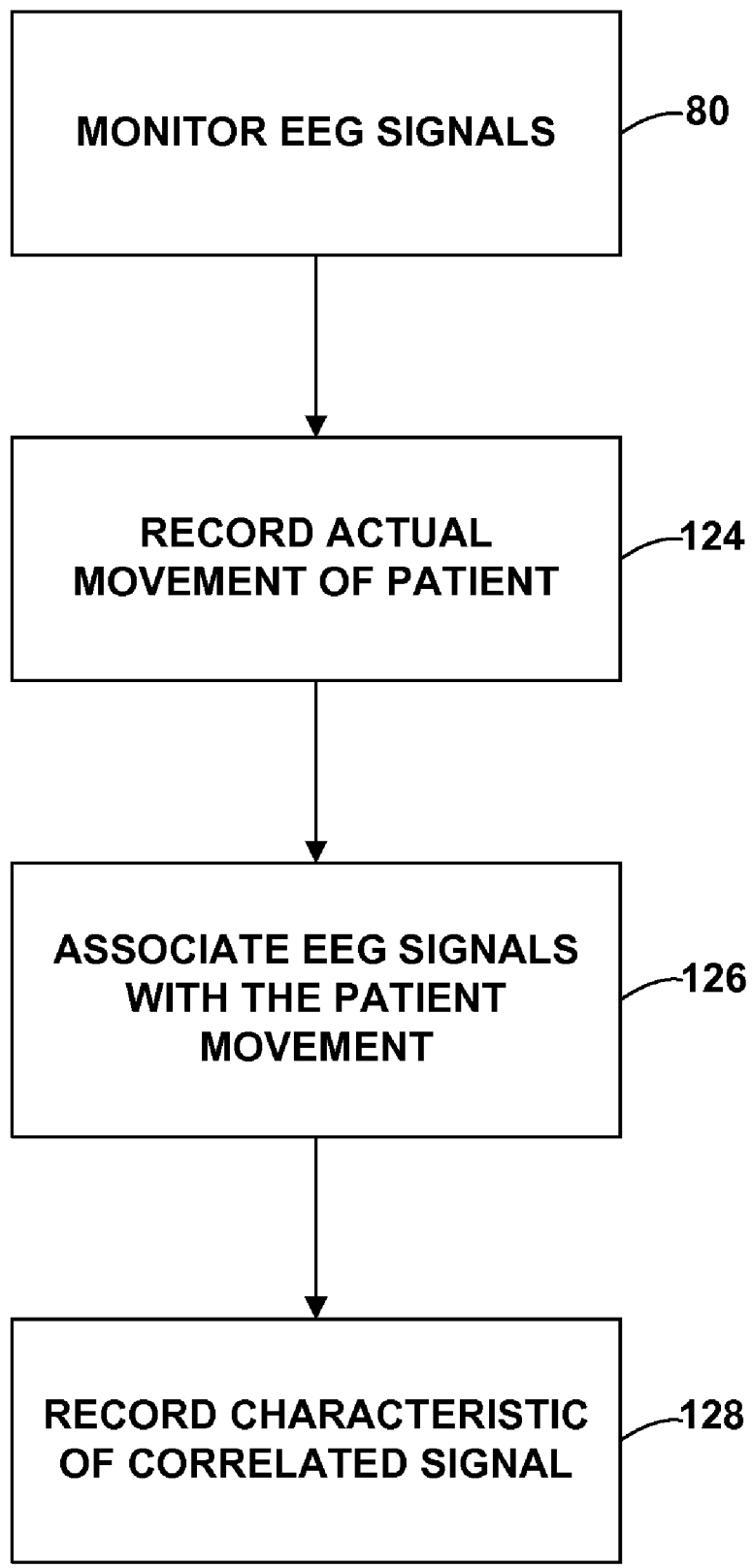
FIG. 14 is a flow diagram of an example technique for determining the EEG signal characteristic that indicates a patient is in a movement state.

FIG. 14 is a flow diagram of a technique for determining the EEG signal (or other bioelectrical brain signal) characteristic (in the time domain or frequency domain) that indicates patient 12 is in a movement state. While FIG. 14 is described with respect to processor 42 of sensing device 14, in other examples, a processor of IMD 32 or IMD 62, or a processor of another computing device, such as a trial sensing device or medical device, may be used to determine the relevant EEG signal characteristics. Factors that may affect the relevant EEG signal characteristic may include factors such as the age, size, and relative health of the patient. The relevant EEG signal characteristic may even vary for a single patient, depending on fluctuating factors such as the state of hydration, which may affect the fluid levels within the brain of the patient. Accordingly, it may be desirable in some cases to measure the EEG signal of a particular patient over a finite trial period of time that may be anywhere for less than one week to one or more months in order to tune the trending data or threshold values to a particular patient.

In some cases, it may also be possible for the relevant EEG signal characteristic to be the same for two or more patients. In such a case, one or more previously determined EEG signal characteristic may be a starting point for a clinician, who may adapt (or "calibrate" or "tune") the EEG signal characteristic value (e.g., a threshold amplitude or power value) to a particular patient. The previously generated EEG signal characteristic value may be, for example, an average of threshold values for a large number (e.g., hundreds, or even thousands) of patients.

Processor 42 of sensing device 14 monitors the EEG signal acquired by sensing module 40 from the relevant region of brain 20 of patient 12 (80). Sensing module 40 may acquire the EEG signal substantially continuously or at regular intervals, such as at a frequency of about 1 Hz to about 100 Hz. The trial period is preferably long enough to measure the EEG signal at different hydration levels and during the course of the initiation of different types of patient movements (e.g., moving an arm or leg, running, walking, and so forth). In addition, the EEG signal for more than one region of brain 20 may also be generated to determine which region of brain 20 provides the most relevant indication of the movement state. The region of brain 20 that provides the most relevant indication of the movement state may influence where electrode array 18 is positioned.

During the same trial period of time, an actual movement of patient 12 is sensed and recorded (124). Any suitable technique may be used for detecting the actual movement of the patient, such as using an external or implanted accelerometer or patient feedback via a patient programmer or another device to indicate patient 12 moved or attempted to move. If possible, patient 12 may, for example, press a button on a device (e.g., programmer 38 of FIG. 2) prior to, during or after a movement to cause the device to record the date and time, or alternatively, cause sensing device 14 to record the date and time of the movement within memory 46.

The time period that begins just prior to the actual movement and continues into the actual movement substantially correlates to the movement state of patient 12. Thus, a time period just prior to the actual movement is associated (or correlated) with the measured EEG signal (126) in order to determine the amplitude of the signal, the power level of the mu rhythm component of the EEG signal, or other EEG signal characteristics that are indicative of the movement state. In one example, a clinician or computing device may review the data relating to the actual movement of patient 12, and associate the EEG signal within a certain time range prior to the actual movement, e.g., 1 millisecond (ms) to about 3 seconds, with the actual patient movement. The clinician or computing device may compare the EEG signals for two or more recorded movements in order to confirm that the particular EEG signal characteristic is indicative of the movement state.

After correlating the EEG signal with a movement, the clinician may record the EEG signal characteristic (128) for later use by processor 42 of sensing device 14. Alternatively, a separate computing device may automatically determine the relevant EEG signal characteristic. In each of the examples described above, the relevant EEG signal characteristic, whether in the form of one or more templates or threshold values, may be stored within memory 46 of sensing device 14 or a memory of another implanted or external device, such as a programming device 38 or IMD 32.

In some cases, a clinician or computing device may also correlate a particular EEG signal with a particular movement or an EEG signal from within a particular region of the motor cortex of brain 20 with a particular movement. For example, if patient 12 is afflicted with tremor that affects the patient's arm during arm movement, and gait freeze that affects both the patient's legs, processor 42 may distinguish between an EEG signal that indicates prospective movement of the patient's arm, and an EEG signal that indicates prospective movement of the patient's legs. Cue generator 54 of external cue device 16 may be configured to deliver different external cues based on the particular movement indicated by the detected EEG signals.

Any suitable means may be used to correlate particular movement with an EEG signal or an EEG signal within a particular region of the motor cortex. For example, an accelerometer may indicate the movement during the trial period or patient 12 may record the type of movement occurring at a particular time, e.g., via a patient programmer or another portable input mechanism. The clinician or computing device may then associate the accelerometer outputs or the patient input with EEG signal of one or more regions of the motor cortex in order to associate a particular motor cortex region with a particular movement.

Brain activity within DLPF cortex of brain 20 of patient 12 may be indicative of prospective movement, and, therefore, a movement state of patient 12. In some examples, a therapy system that is useful for controlling a movement disorder may sense brain signals within the DLPF cortex of brain 20 of patient 12 and time the delivery of therapy such that the therapy is delivered prior to perception of the movement by patient 12. This timing of therapy delivery to patient 12 may help minimize perception of any movement disorder symptoms by patient 12. In some cases, the therapy system may time the delivery of therapy such that patient 12 does not substantially perceive an inability to initiate movement or another effect of a movement disorder.

The DLPF cortex is an anterior portion of the neocortex of brain 20 (i.e., the frontal lobe), and plays a role in early initiation of executive thoughts and actions. The initiation of executive thoughts and actions in the DLPF cortex may occur prior to perception of such thoughts and actions by patient 12. Thus, bioelectrical signals within the DLPF cortex may indicate prospective movement of patient 12 prior to the generation of bioelectrical signals within the premotor cortex or the primary motor cortex that indicate movement or intent of movement. Sensing activity in the DLPF cortex of brain 20 may be used to detect early, premovement signals, which may then be used to control delivery of a therapy that controls the movement disorder. In this way, electrical activity within the DLPF cortex may be a "biomarker" or "biosignal" that is indicative of prospective movement of patient 12.

In some examples described herein, biosignals within the DLPF cortex of brain 20 of patient 12 may be used to detect a movement state of patient 12, and detection of the movement state may be used to control the operation of a device, such as a therapy delivery device or a non-medical device. By continuously or intermittently sensing activity with the DLPF cortex, prospective movement of patient 12 may be detected before patient 12 moves, or even perceives the movement. In some examples, upon detecting prospective movement of patient 12, therapy delivery may be triggered or adjusted in order to help patient 12 initiate muscle movement or otherwise control any effects of the movement disorder. In some examples, the therapy is delivered to patient 12 without any recognized delays by patient 12 (e.g., without any significant amount of time between the patient's recognition of a desire and inability to move and the delivery of therapy to help initiate movement).

The brain signals sensed within the DLPF cortex of brain 20 may provide an input to control a therapy delivery device, such as external cue device 16 (FIG. 1A) or IMD 62 (FIG. 5). As an example, external sensing device 14 may sense brain signals within the DLPF cortex of brain 20 of patient 12 with the aid of external electrode array 18 (FIG. 1A). Sensing electrodes 24A-24E (FIG. 1B) may be positioned on an exterior surface of patient 12 near the cortex of brain 20. In other examples, implanted sensing device 32 (FIG. 2) may sense brain signals within the DLPF cortex of brain 20 with the aid of implanted electrode array 34. External sensing device 14 and implanted sensing device 32 may generate a control signal or otherwise communicate the sensed brain signal to a therapy delivery device, such as external cue device 16 (FIG. 1) or IMD 62 (FIG. 5), which may deliver therapy to patient 12 to help control a movement disorder of patient 12 upon determining that the brain signal is indicative of prospective movement of patient 12. In other examples, external sensing device 14 or implanted sensing device 32 may determine whether the brain signal within the DLPF cortex indicates a movement state of patient 12.

Figure 15:
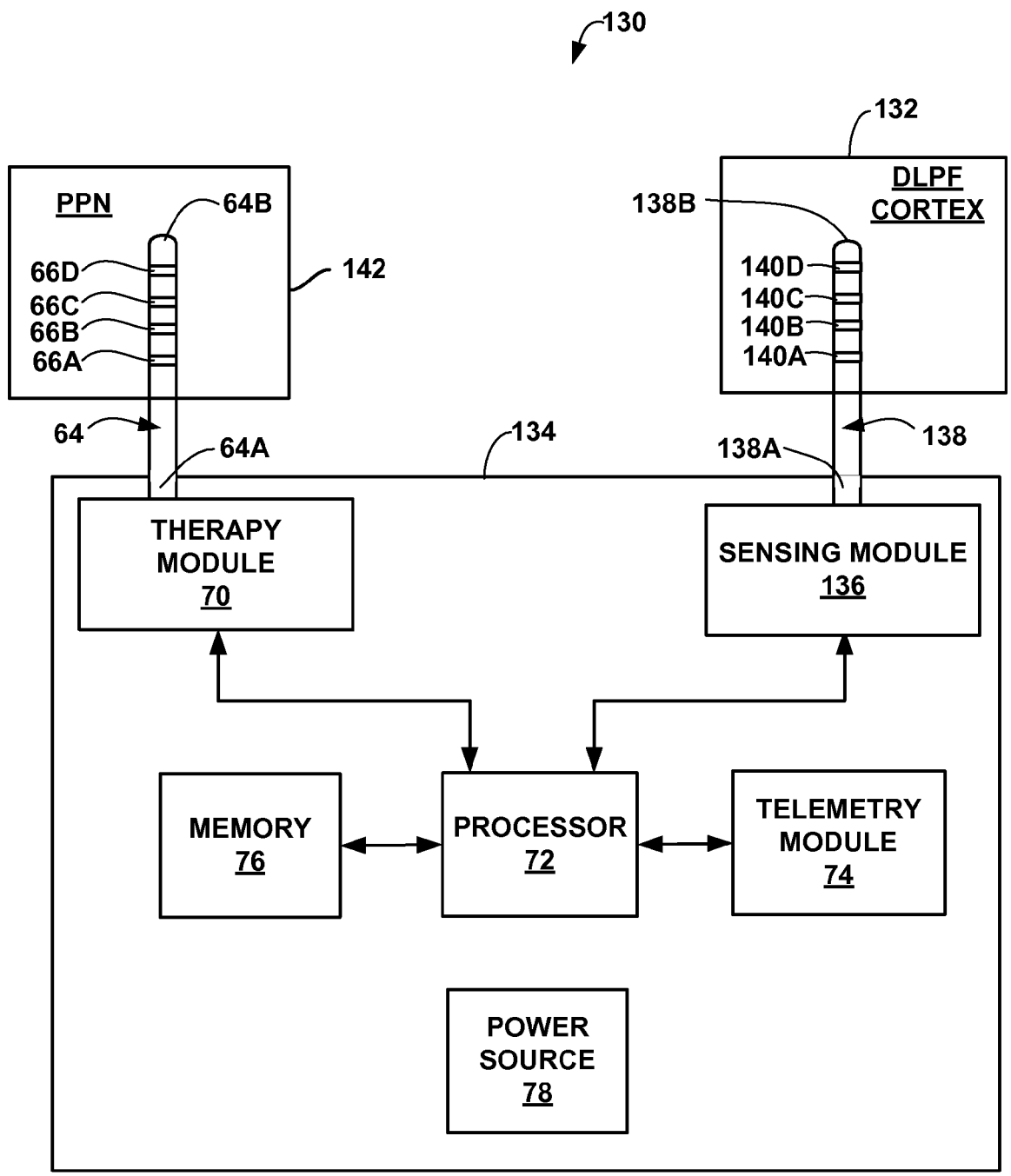
FIG. 15 is a block diagram illustrating an example therapy system for treating movement disorders and illustrates various components of a medical device.

FIG. 15 is a conceptual block diagram illustrating an example therapy system 130 that may be used to deliver therapy to brain 20 of patient 12 in response to detecting brain signals within DLPF cortex 132 that are indicative of prospective movement of patient 12. Detection of the brain signal indicative of prospective movement of patient 12 may be indicative of a movement state of patient 12. Therapy system 130 includes IMD 134, which is substantially similar to IMD 62 of FIG. 5. In addition to therapy module 70, processor 72, telemetry module 74, memory 76, and power source 78, which are described above with respect to FIG. 5, IMD 134 includes sensing module 136, which senses bioelectrical signals within brain 20 of patient 12. In the example shown in FIG. 15, sensing module 136 is electrically coupled to implantable medical lead 138, which includes electrodes 140A-140D to sense bioelectrical signals within DLPF cortex 132 of brain 20 of patient 12.

The control of modules 70, 74, 76, and 136 may be implemented as programmable features, applications or processes of processor 72, or implemented via other processors or hardware units. Furthermore, the control of modules 70, 74, 76, and 136 may be implemented in hardware, software, and/or firmware, or any combination thereof.

Sensing circuitry within sensing module 136 monitors physiological signals from DLPF cortex 132 of brain 20 via one or more sensing electrodes 140A-140D under the control of processor 72. Sensing module 136 may sense activity within DLPF cortex 132 using sensing levels of about 5 microvolts root-means-square ($\mu V$ rms) to about 200 $\mu V$ rms. In the example shown in FIG. 15, processor 72 includes a signal processor to process the signals from DLPF cortex 132, while in other examples, sensing module 136 may include the signal processor. Processor 72 may sample the signals (either digital or analog) from sensor module 136, and process the sensor signals to determine whether the signals from DLPF cortex 132 are indicative of prospective movement of patient 12. If prospective movement is detected, processor 72 may control therapy module 70 to initiate or adjust delivery of electrical stimulation therapy to PPN 48.

Processor 72 may control therapy module 70 to deliver the electrical stimulation signals via selected subsets of electrodes 66A-66D with selected polarities. For example, electrodes 66A-66D may be combined in various bipolar or multipolar combinations to deliver stimulation energy to stimulation sites within brain 20. Processor 72 may also control therapy module 70 to deliver each stimulation signal according to a different program, thereby interleaving programs to simultaneously treat different symptoms of the movement disorder, provide a combined therapeutic effect, and, in some cases, another condition that may be controlled or otherwise treated by the stimulation therapy.

In the example shown in FIG. 15, electrodes 66A-66D of lead 64 are positioned to deliver therapy to PPN 142 of brain 20 of patient 12 in response to sensing module 136 sensing a biomarker indicative of prospective movement of patient 12 within the DLPF cortex 132. In other examples, however, stimulation may be delivered to other regions of brain 20.

PPN 142 is located in the brainstem of brain 20, caudal to the substantia nigra and adjacent to the superior cerebellar peduncle. The brainstem is located in the lower part of brain 20, and is adjacent to and substantially continuous with the spinal cord of patient 12. PPN 142 is a major brain stem motor area and controls gait and balance of movement, as well as muscle tone, rigidity, and posture of patient 12.

It is believed that DLPF cortex 132 of brain 20 controls activity within PPN 142. DLPF cortex 132 control of PPN activity may be hindered in patients with Parkinson's disease (PD). Therapy delivery to PPN 142 in response to a biomarker detected within DLPF cortex 132 may be used to normalize the DLPF cortex control of PPN activity. For example, external sensing electrodes 140A-140D may sense brain activity within DLPF cortex 132 and processor 72 may determine whether the brain signals are indicative of prospective movement of patient 12. Upon determining that the brain signals within DLPF cortex 132 indicate patient 12 is in a movement state, processor 72 may control therapy module 70 initiate or adjust the delivery of stimulation to PPN 142. In this way, bioelectrical activity within DLPF cortex 132 within a certain range triggers delivery of electrical stimulation to PPN 142 by therapy module 70, and the therapy delivery may act as a surrogate to normal brain function (i.e., the "circuit" between DLPF cortex 132 and PPN 142).

The stimulation administered by IMD 134 to PPN 142 may be selected based on the specific movement disorder of patient 12, and the effect of the stimulation on other parts of brain 20. For example, stimulation using a relatively high frequency (e.g., greater than 100 Hz) to block the output of the pars compacta region of PPN 142 may decrease the excitatory input to the ventrolateral (VL) thalamus, which may be useful for treating hyperkinetic movement disorders. On the other hand, stimulation using a low frequency to facilitate the excitatory output of the pars compacta region of PPN 142 may alleviate symptoms for persons with hypokinetic movement disorders. Glutamatergic neurons within the pars dissipatus region of PPN 142 receive outputs from the main subthalamic nucleus, the internal globus pallidus, and the substantia nigra pars reticulate, and provide the main outflow of information to the spinal cord. Stimulation to influence glutamatergic neurons within the pars dissipatus region of PPN 142 may be useful to initiate or otherwise control patient movement. The stimulation parameter values may vary depending upon the type of neurons in PPN 142 that are stimulated. Continuous mid-frequency stimulation on the order of about 20 Hz to about 60 Hz may be useful for initiating patient movement, while relatively high frequency stimulation (e.g., greater than about 100 Hz) may be useful for achieving other effects, such as reducing muscle rigidity.

Providing stimulation on demand, when movement-specific activation is desired, may be more beneficial than providing continuous or substantially continuous stimulation to PPN 142 or other brain sites. In some cases, continuous or substantially continuous delivery of stimulation to PPN 142 may interfere with other brain 20 functions, such as activity within subthalamic nucleus, as well as therapeutic deep brain stimulation in other basal ganglia sites. In addition providing stimulation intermittently or upon the sensing of movement by patient 12 (or in the case of DLPF cortex sensing, the thought that precedes actual movement), may be a more efficient use of energy. Stimulation may not be necessary when, for example, patient 12 is not moving or thinking about movement. Delivering stimulation only when needed or when desirable may help conserve a power source within IMD 134. As previously described, delivering stimulation or another therapy to patient 12 on demand, e.g., when patient 12 is initiating movement or thinking about initiating movement, may help minimize the patient's adaptation to the therapy.

IMD 134 may also be configured to deliver stimulation to other regions within patient 12, in addition to or as an alternative to delivering stimulation to PPN 142. As examples, IMD 134 may deliver electrical stimulation therapy to the thalamus, basal ganglia structures (e.g., globus pallidus, substantia nigra, subthalamic nucleus), zona inserta, fiber tracts, lenticular fasciculus (and branches thereof), ansa lenticularis, and/or the Field of Forel (thalamic fasciculus) of brain, or to the spinal cord of patient 12, nerves, muscles or muscle groups of patient 12, or another suitable site within patient 12 in order to help patient 12 control muscle movement.

In addition to or instead of utilizing activity within DLPF cortex 132 as an input to control delivery of electrical stimulation or fluids (e.g., drugs), activity within DLPF cortex 132 may be useful for activating or adjust other forms of therapy, such as the delivery of a sensory cue (e.g., visual, auditory or somatosensory cue) with an implanted device or an external device. For example, upon detecting a signal within DLPF cortex 132 that is indicative of prospective movement of patient 12, processor 72 may control therapy module 70 to stimulate a visual cortex of brain 20 simulate a visual cue or deliver an internal sound in order to simulate a particular sight or sound that activates patient movement. As The particular sensory cue may differ between patients and between patient conditions. Somatosensory cutes may include a vibration or another tactile cue. Alternatively, the sensory cue may be delivered via another implanted device. As another example, processor 72 may control an external cue device 16 (FIG. 1A) to deliver the visual cue in response to detecting a movement state of patient 12 based on brain signals within DLPF cortex 132 of brain 20. An implanted sensory cue device may be more discreet than external device, but an external device may be less invasive. Other sensory cue delivery techniques are contemplated.

In some cases, if patient 12 is afflicted with Parkinson's disease, patient 12 may be susceptible to gait freeze, which may be an incapacitating symptom of Parkinson's disease. In some patients, a sensory cue may help activate PPN 142 or another portion of brain 20 that is responsible for activating movement. Delivering a sensory cue in response to detection of a brain signal within DLPF cortex 132 that is indicative of prospective patient movement may disrupt brain activity that is hindering patient movement, thereby enabling patient 12 to initiate movement. The sensory cue may be used in addition to or instead of electrical stimulation therapy or fluid delivery therapy.

In addition to controlling therapy delivery, sensing activity within DLPF cortex 132 may be useful for controlling other devices because activity within the DLPF cortex 132 may generally be a biological marker for movement. Detection of movement may be useful for activating other devices, such as the activation of a prosthetic limb, activation of a patient transport device (e.g., a wheelchair), and so forth.

In other examples, the activity detected within DLPF cortex 132 may be used in a therapy system to control other types of therapy. For example, fluid (e.g., a drug) may be delivered to one or more regions of brain 20, the spinal cord, muscle, muscle group or another site within patients 14 in order to help patient 12 initiate muscle movement. As another example, a sensory cue may be delivered to patient via an external device or an implanted device to help patient 12 initiate muscle movement. In general, the delivery of electrical stimulation or drug therapy may help alleviate, and in some cases, eliminate symptoms associated with movement disorders.

Although FIG. 15 illustrates an example in which therapy module 70 and sensing module 136 are disposed in a common housing, the disclosure is not limited to such examples. In other examples, therapy module 70 may be separate from sensing module 136. For example, therapy module 70 may be configured to deliver therapy to a region of patient 12 other than brain 20. As examples, sensing module 136 or another sensing module may detect signals within DLPF cortex 132 that are indicative of prospective movement of patient 12 and initiate functional electrical stimulation (FES) or transcutaneous electrical stimulation (TENS) of a muscle or muscle group of patient 12 in order to help initiate movement or help patient 12 control movement of a limb or other body part. In the case of FES, IMD 134 may be implanted to deliver stimulation to a muscle, rather than brain 20 of patient 12.

As another example, sensing module 136 may be incorporated into an external sensing device that is coupled to an external sensor, such as external sensing device 14 shown in FIG. 1A. In some examples, external sensing device 14 (FIG. 5) may monitor a brain signal within DLPF cortex 132 of brain 20 via external sensing electrodes 24A-24E and processes the signals to determine if the signals are indicative of prospective movement of patient 12. Upon detecting a signal indicative of prospective movement, sensing device 14 may provide an input to IMD 62 (FIG. 5) via wireless telemetry, such as with RF communication techniques. In response to receiving the input from sensing device 14, processor 72 of IMD 134 may control delivery of therapy to patient 12, such as initiating the delivery of electrical stimulation to patient via therapy module 70, or adjusting parameters of the stimulation.

Figure 16:
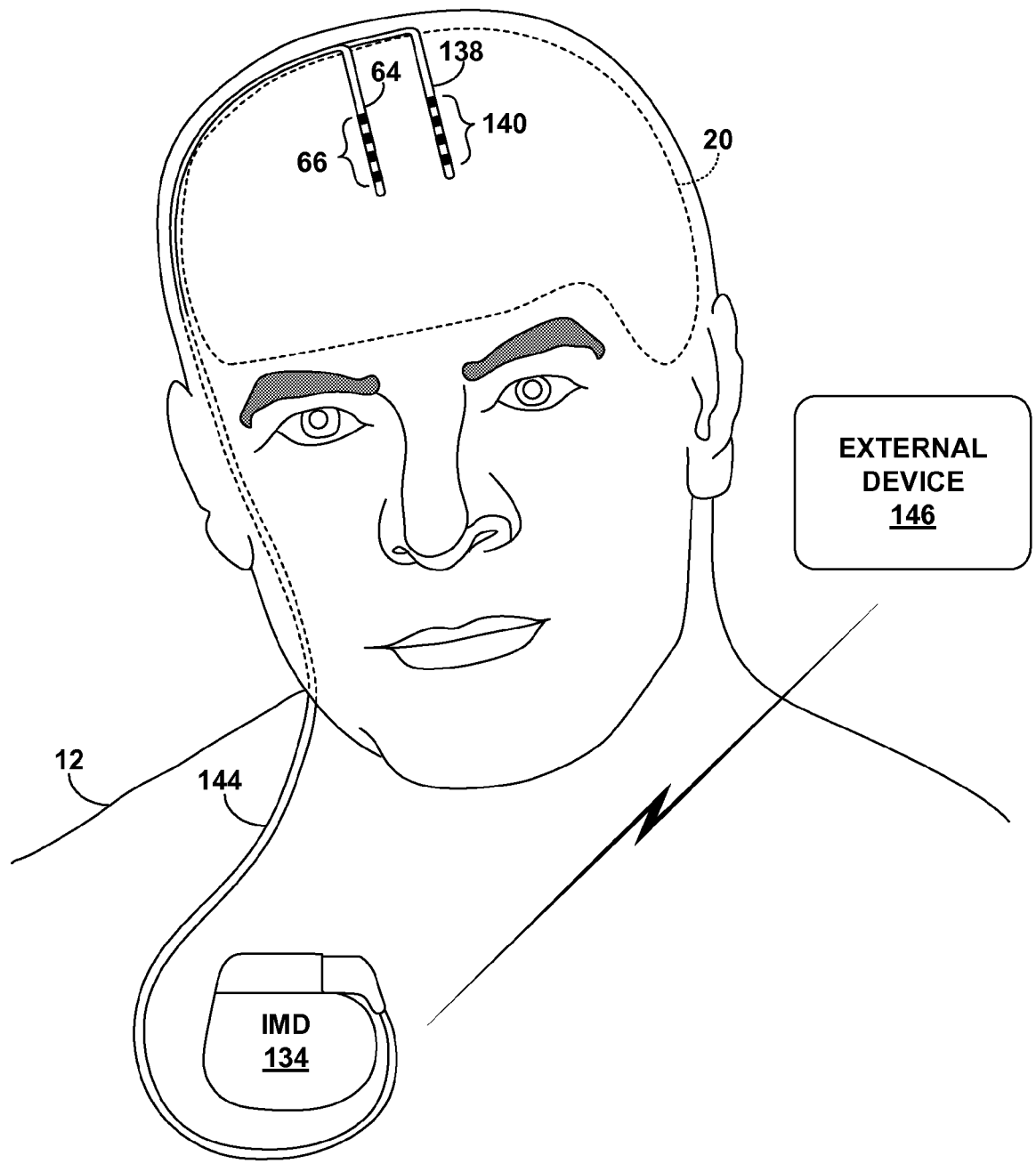
FIG. 16 illustrates a therapy system in which activity sensed within a dorsal lateral prefrontal cortex (DLPF) is used to control an external device.

FIG. 16 illustrates the therapy delivery system shown in FIG. 15, in which IMD 134 includes both therapy module 70 to provide electrical stimulation therapy via electrodes 66A-66D (collectively "electrodes 66") and sensing module 136 to sense activity in DLPF cortex 132 via implanted sensing electrodes 140A-140D (collectively "electrodes 140"). In the example shown in FIG. 16, leads 64, 138 are coupled to a common lead extension 144. In other examples, however, at least one of the leads 64, 138 may be directed coupled to IMD 134 without the aid of lead extension 144. In FIG. 16, instead of or in addition to controlling therapy module 70 upon sensing a particular level of activity within DLPF cortex 132, processor 72 (or another controller within IMD 134) is configured to control external device 146.

FIG. 16 also illustrates external device 146, which may be any device that is not fully-implanted within patient 12. Processor 72 may communicate with external device 146 via telemetry module 74 of IMD 134 (FIG. 15) according to any suitable wireless communication technique known in the art, such as RF communication techniques. External device 146 and IMD 134 may be configured for unidirectional communication (i.e., one-way communication from IMD 134 to external device 146) or bidirectional communication. Thus, in some examples, external device 146 may include a transceiver for sending data to and receiving data from IMD 134, or merely a receiver configured to receive data (e.g., commands or instructions) from processor 72 of IMD 134.

Examples of external devices 146 that processor 72 may control include a device mounted to patient 12 to provide a sensory cue to help initiate patient movement, a prosthetic limb, a patient transport device, or even non-medically related devices, such as appliances (e.g., light source, stove, television, radio, computing device, semi-automated doors, and so forth). An "appliance" generally refers to a device that is used for a particular use or purpose unrelated to therapy delivery to patient 12.

In general, brain signals detected within DLPF cortex 132 may be used to control external device 146, regardless of whether device 146 is configured to treat or otherwise control a movement disorder or whether device 146 is unrelated to the movement disorder. IMD 134 or another sensing device may monitor signals within DLPF cortex 132 of brain 20 of patient 12 and upon detecting a signal indicative of prospective patient movement, processor 72 may send a control signal to external device 146 via telemetry module 74.

In examples in which external device 146 includes a prosthetic limb or the like, external device 146 may include a power source to provide power to a sensing circuitry to sense movement of a particular muscle or muscle group of patient 12 or other components. The prosthetic limb may include a sleep mode during periods of disuse of the prosthetic in order to conserve power. Upon detecting the early signs that patient 12 wants to initiate movement (via a signal within DLPF cortex 132), IMD 134 may send a signal to external device 146 in order to wake the prosthetic up from its sleep state. If external device 146 includes a patient transport device, such as a wheelchair, the wheelchair may be configured to activate or propel in a particular direction based on detection of a signal within DLPF cortex 132 that indicates patient 12 is executing thoughts of movement. In examples in which external device 146 includes a lamp or another nonmedical appliance, IMD 134 may send a signal to a receiver on the lamp to turn the lamp on if IMD 134 detects a signal indicative of prospective movement of patient 12.

In other examples, an external device, such as external sensing device 14 (FIG. 1A) may be used to sense brain signals within DLPF cortex 132 of brain 20 and control external device 146 upon determining patient 12 is in a movement stated based on the sensed brain signals. Moreover, in some examples, external device 146 may be controlled by an external or an implanted medical device that does not include therapy module 70 to deliver therapy to patient 12.

Figure 17:
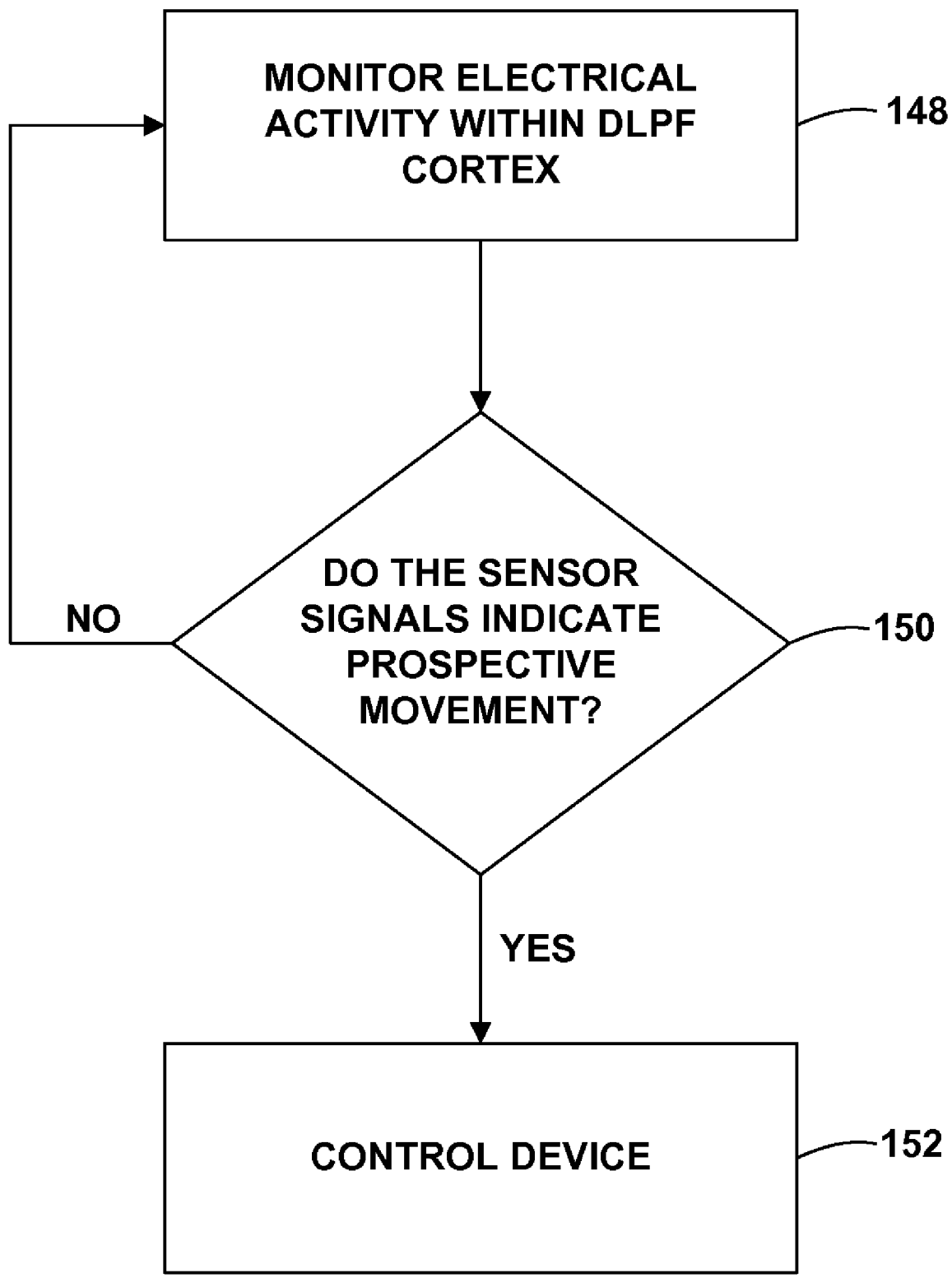
FIG. 17 is a flow diagram of an example technique for controlling a device, such as an external device or therapy delivery device, based on a brain signal within the DLPF cortex of a patient.

FIG. 17 is a flow diagram of an example technique for controlling a device, such as an external device 146 (FIG. 16) or therapy delivery to patient 12, e.g., via therapy module 70 within IMD 134 (FIG. 15). While the techniques shown in FIGS. 17-19 and 21 are primarily described as being performed by processor 72 of IMD 134, in other examples, a processor of another device, such as external sensing device 14, external cue device 16 or implanted sensing device 32, may perform any part of the techniques described herein.

Processor 72 may monitor brain signals within DLPF cortex 132 (FIG. 15) substantially continuously or at regular intervals (148). In examples in which a therapy system includes implanted sense electrodes 140 (FIG. 15), sensing electrodes 140 may be positioned proximate to DLPF cortex 132. In examples in which a therapy system includes external sensing electrodes 24A-24E (FIG. 1B), sensing electrodes 24A-24E may be positioned on a surface of patient 12 proximate to DLPF cortex 132. In some cases, implanted sensing electrodes 140 may monitor the activity of DLPF cortex 132 better than external sensing electrodes 24A-24E due to the proximity to DLPF cortex 132. In either case sensing module 136 (FIG. 15) of IMD 134 may receive signals from sensing electrodes 24A-24E or 140 that are indicative of the bioelectrical activity within DLPF cortex 132.

Processor 72 of IMD 134 may receive sensor signals from sensing module 136 and process the sensor signals to determine whether the sensor signals indicate a prospective movement of patient 12 (150). If the sensor signals are not indicative of prospective movement, sensing module 136 may continue sensing activity within DLPF cortex 132 under the control of processor 72 (148). If the sensor signals are indicative of prospective movement, processor 72 may control of a device (152). As previously discussed, the device may be external device 146 (FIG. 16) or a therapy delivery device (e.g., external cue device 16 or therapy module 70). For example, upon processing the DLPF cortex signals received from sensing module 136 and determining that patient 12 is initiating thoughts of movement, processor 72 may activate therapy module 70 of IMD 132. Therapy module 70 may activate therapy in response to detection of prospective movement of patient 12 via the signals from DLPF cortex 132 or adjust therapy (e.g., increase therapy in order to help patient 12 initiate muscle movement).

A signal processor within processor 72 or sensing module 136 of IMD 134 may determine whether the DLPF cortex signals sensed by sensing module 136 are indicative of prospective movement using any suitable technique. As various examples, the electrical signals may be analyzed for amplitude, temporal correlation or frequency correlation with a template signal, or combinations thereof. For example, the instantaneous or average amplitude of the electrical signal over a period of time may be compared to an amplitude threshold. As another example, a slope of the amplitude of the signal over time or timing between inflection points or other critical points in the pattern of the amplitude of the electrical signal over time may be compared to trend information. A correlation between the inflection points in the amplitude waveform of the electrical signal or other critical points and a template may indicate prospective movement. Sensing module 136 or processor 72 may condition the signals, if necessary.

As another example, the signal processor within processor 72 or sensing module 136 may perform temporal correlation by sampling the waveform generated by the electrical signals within DLPF cortex 132 with a sliding window and comparing the waveform with a stored template waveform. For example, processor 72 of IMD 134 or a processor of another device, implanted or external, may perform a correlation analysis by moving a window along a digitized plot of the amplitude waveform of DLPF cortex 132 signals at regular intervals, such as between about one millisecond to about ten millisecond intervals, to define a sample of the brain signal. The sample window may be slid along the plot until a correlation is detected between the waveform of the template and the waveform of the sample of the brain signal defined by the window. By moving the window at regular time intervals, multiple sample periods are defined. The correlation may be detected by, for example, matching multiple points between the template waveform and the waveform of the plot of the brain signal over time, or by applying any suitable mathematical correlation algorithm between the sample in the sampling window and a corresponding set of samples stored in the template waveform.

Frequency correlation is described in further detail below. In general, in some examples, the brain signal from DLPF cortex 132 may be analyzed in the frequency domain to compare selected frequency components of an amplitude waveform of the signal within DLPF cortex 132 to corresponding frequency components of a template signal. For example, one or more specific frequency bands may be more revealing of prospective movement of patient 12 than others, and the correlation analysis may include a spectral analysis of the electrical signal component in the revealing frequency bands. The frequency component of the electrical signal may be compared to a frequency component of a template.

Figure 18A:
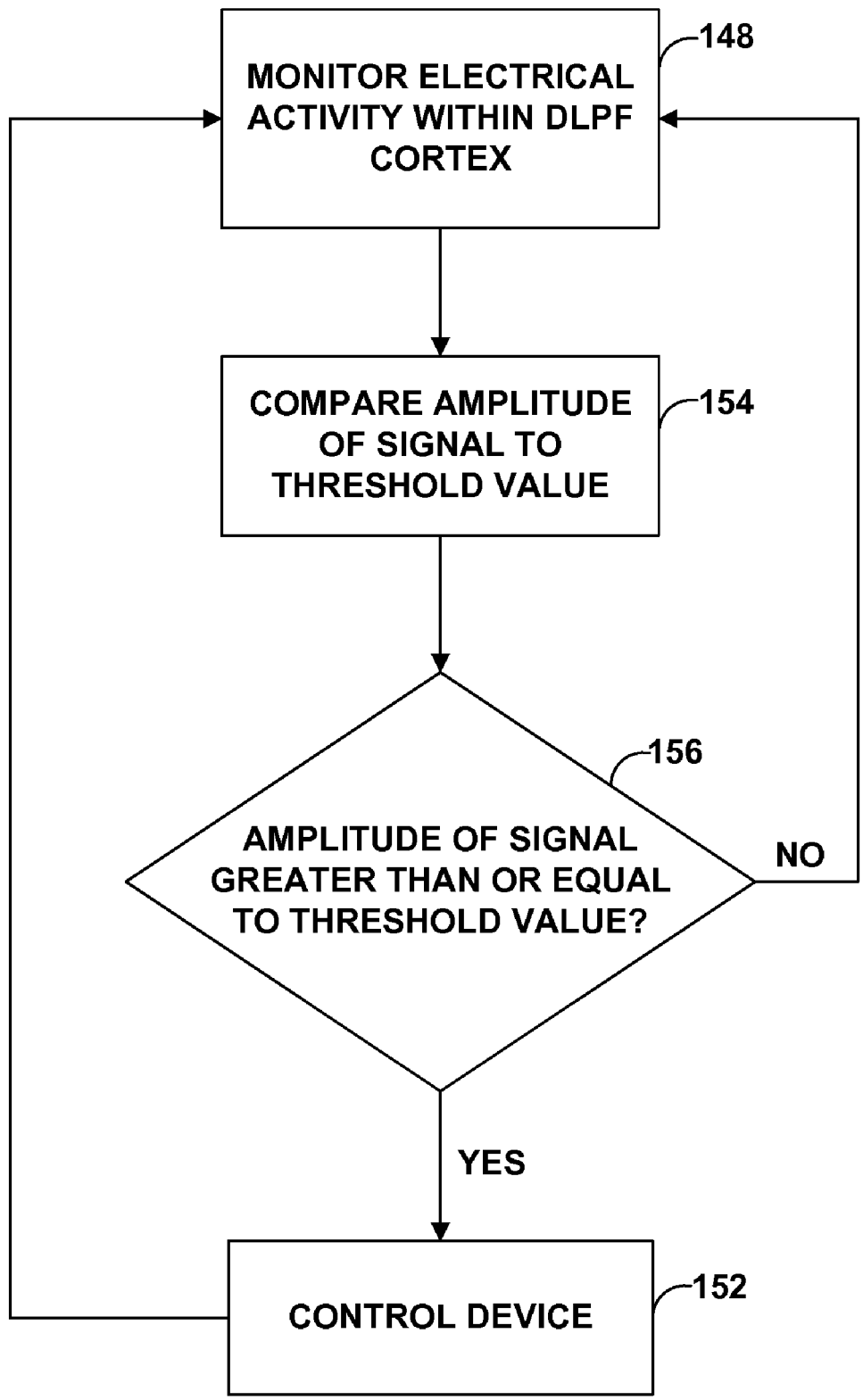
FIG. 18A is a flow diagram illustrating an example technique for analyzing electrical activity within the DLPF cortex to determine whether the activity indicates prospective patient movement.

FIG. 18A is a flow diagram illustrating an example technique for analyzing electrical activity within DLPF cortex 132 to determine whether the activity indicates prospective patient movement. Processor 72 of IMD 134 may implement the technique shown in FIG. 18A in order to process electrical signals sensed within DLPF cortex 132 and predict movement of patient 12. Sensing module 136 of IMD 134 may substantially continuously or intermittently monitors electrical activity within DLPF cortex 132 via one or more electrodes 140 (148). Processor 72 may compare an amplitude of the monitored electrical signal to a predetermined threshold value (154). The relevant amplitude may be, for example, the instantaneous amplitude of an incoming electrical signal or an average amplitude of electrical signal over period of time. In one example, which is described below with reference to FIG. 18B, the threshold value is determined during the trial phase that precedes the implementation of a chronic therapy delivery device within patient 12.

If the measured electrical signal from within DLPF cortex 132 is greater than the threshold value (156), processor 72 may control the operation of a device based on the brain signal within the (152). In one example, if the measured electrical signal from within DLPF cortex 132 is greater than the threshold value (156), processor 72 may control therapy module 70 of IMD 132 to initiate therapy delivery or adjust at least one therapy parameter value. Processor 72 may adjust a therapy parameter value by switching therapy programs that defines the therapy parameter values for therapy module 70 or by modifying one or more therapy parameter values. A clinician may limit the extent to which processor 72 may adjust a therapy parameter value, such as, for example, by setting a minimum and maximum value for various therapy parameter values (e.g., stimulation amplitude or frequency or a frequency of a delivery of a drug bolus). In other examples, therapy may be delivered to patient 12 via a therapy delivery device that is separate from sensing module 136. In another example, processor 72 may control external device 146 to deliver a sensory cue or perform another function (e.g., turn a light on or propel a patient transport device). In addition, other actions may be triggered if the amplitude of the electrical signal within DLPF cortex 132 exceeds or equals the amplitude threshold. For example, IMD 132, external device 146 or another device, such as an external programming device may also record the electrical signals for later analysis by a clinician. On the other hand, if the amplitude of the electrical signal is less than or equal to the threshold value (156), processor 72 may continue monitoring the electrical activity within DLPF cortex 132.

After processor 72 controls a device in response to receiving the signal within DLPF cortex 132 that is indicative of prospective movement (152), sensing module 136 may continue measuring the electrical activity within DLPF cortex 132 (148). This pattern of responsive therapy delivery may continue indefinitely. Alternatively, the electrical activity may be measured for a limited period of time, such as periodically during relevant times during the day (e.g., when the patient is awake).

Figure 18B:
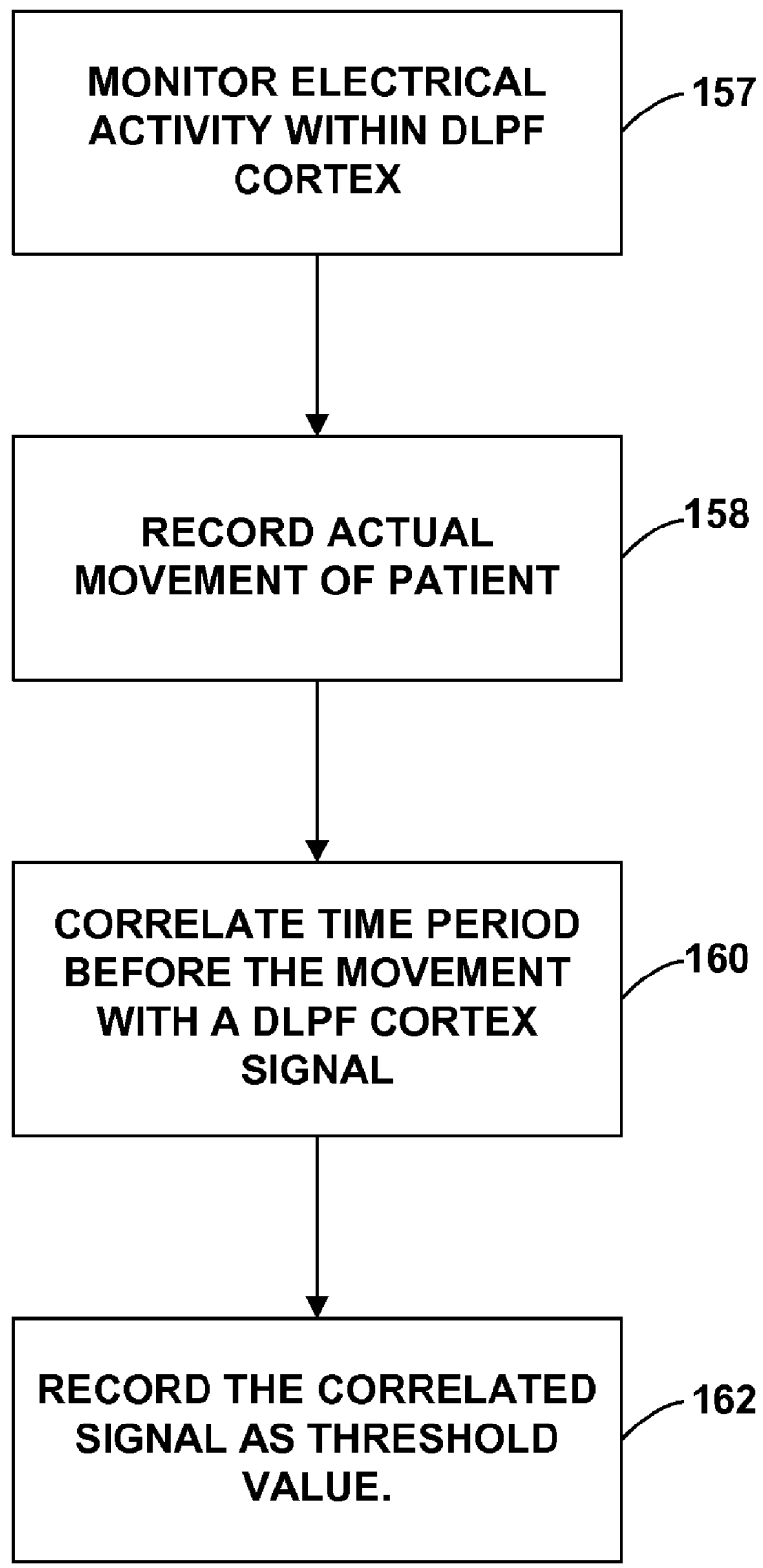
FIG. 18B is a flow diagram illustrating a technique for determining one or more threshold amplitude values for determining whether electrical activity within the DLPF cortex is indicative of prospective movement.

FIG. 18B is a flow diagram illustrating an example technique for determining one or more threshold amplitude values that suggest a sensed signal from within DLPF cortex 132 is indicative of prospective movement of patient 12. The absolute amplitude value that indicates intended movement may differ depending on the patient. Factors that may affect the threshold value may include factors such as the age, size, and relative health of the patient. The relevant threshold amplitude may even vary for a single patient, depending on fluctuating factors such as the state of hydration, which may affect the fluid levels within the brain of the patient. Accordingly, it may be desirable in some cases to measure the DLPF cortex 132 activity of a particular patient over a finite trial period of time that may be anywhere for less than one week to one or more months in order to tune the trending data or threshold values to a particular patient.

It may be possible for the relevant threshold values to be the same for two or more patients. In such a case, one or more previously generated threshold values may be a starting point for a clinician, who may adapt (or "calibrate" or "tune") the threshold values to a particular patient. The previously generated threshold values may be, for example, an average of threshold values for a large number (e.g., hundreds, or even thousands) of patients.

The electrical activity within DLPF cortex 132 is monitored during a trial period of time with IMD 134 (FIG. 15), although an external sensing device 14 or another type of sensing device may also be used in other examples (157). Sensing module 136 of IMD 134 may measure the amplitude of the electrical activity substantially continuously or at regular intervals, such as at a frequency of about 1 Hz to about 100 Hz. The trial period is preferably long enough to measure the amplitude of the electrical signal within DLPF cortex 132 at different hydration levels and during the course of the initiation of different patient movements (e.g., moving an arm or leg, running, walking, and so forth). During the same trial period of time, actual movement of patient 12 is sensed and recorded (158). Any suitable technique may be used for detecting the actual movement of the patient, such as using an external or implanted accelerometer or patient input via a patient programmer or another device to indicate patient 12 moved or attempted to move. If possible, patient 12 may, for example, press a button on a device prior to, during or after a movement to cause the device to record the date and time, or alternatively, cause the trial device or a programming device to record the date and time of the movement.

The time period prior to the movement, which substantially correlates to the time period in which patient 12 initiated thoughts of movement within DLPF cortex 132, are associated (or correlated) with measured DLPF cortex 132 signals (160) in order to determine the amplitude of the signal or other threshold values that are indicative prospective movement. In one example, a clinician or computing device may review the data relating to the actual movement of patient 12, and associate the electrical activity measurements taken within a certain time range prior to the actual movement, e.g., 1 millisecond (ms) to about 3 seconds, with the actual patient movement. The clinician or computing device may review the relevant amplitude values for two or more recorded movements in order to confirm that the threshold value is indicative of prospective movement.

After correlating the electrical activity with an actual movement, the clinician may record the amplitude of the relevant electrical brain signal(s) as the relevant threshold value (162). Alternatively, the correlation and threshold value recording may be automatically performed by a computing device or with the aid of a computing device. In each of the examples described above, the one or more templates may be stored within memory 76 (FIG. 15) of IMD 134 or a memory of another implanted or external device, such as a programming device for IMD 134.

In some cases, a clinician or computing device may also correlate a particular signal within DLPF cortex 132 with a particular movement. For example, if patient 12 is afflicted with tremor that affects the patient's arm during arm movement, and gait freeze that affects both the patient's legs, processor 72 may distinguish between a DLPF cortex 132 signal that indicates prospective movement of the patient's arm, and a DLPF cortex 132 signal that indicates prospective movement of the patient's legs. Therapy module 136 may then be configured to deliver therapy to PPN 142 (FIG. 15) or different parts of brain 20 or the patient's body based on the particular movement indicated by signals sensed within DLPF cortex 132.

Any suitable means may be used to correlate particular movement with a DLPF cortex signal. For example, an accelerometer may indicate the movement during the trial period or patient 12 may record the type of movement occurring at a particular time, e.g., via a patient programmer or another portable input mechanism. The clinician or computing device may then associate the accelerometer outputs or the patient input with DLPF cortex signals in order to determine what types of prospective movements the DLPF cortex signals indicate.

Figure 19A:
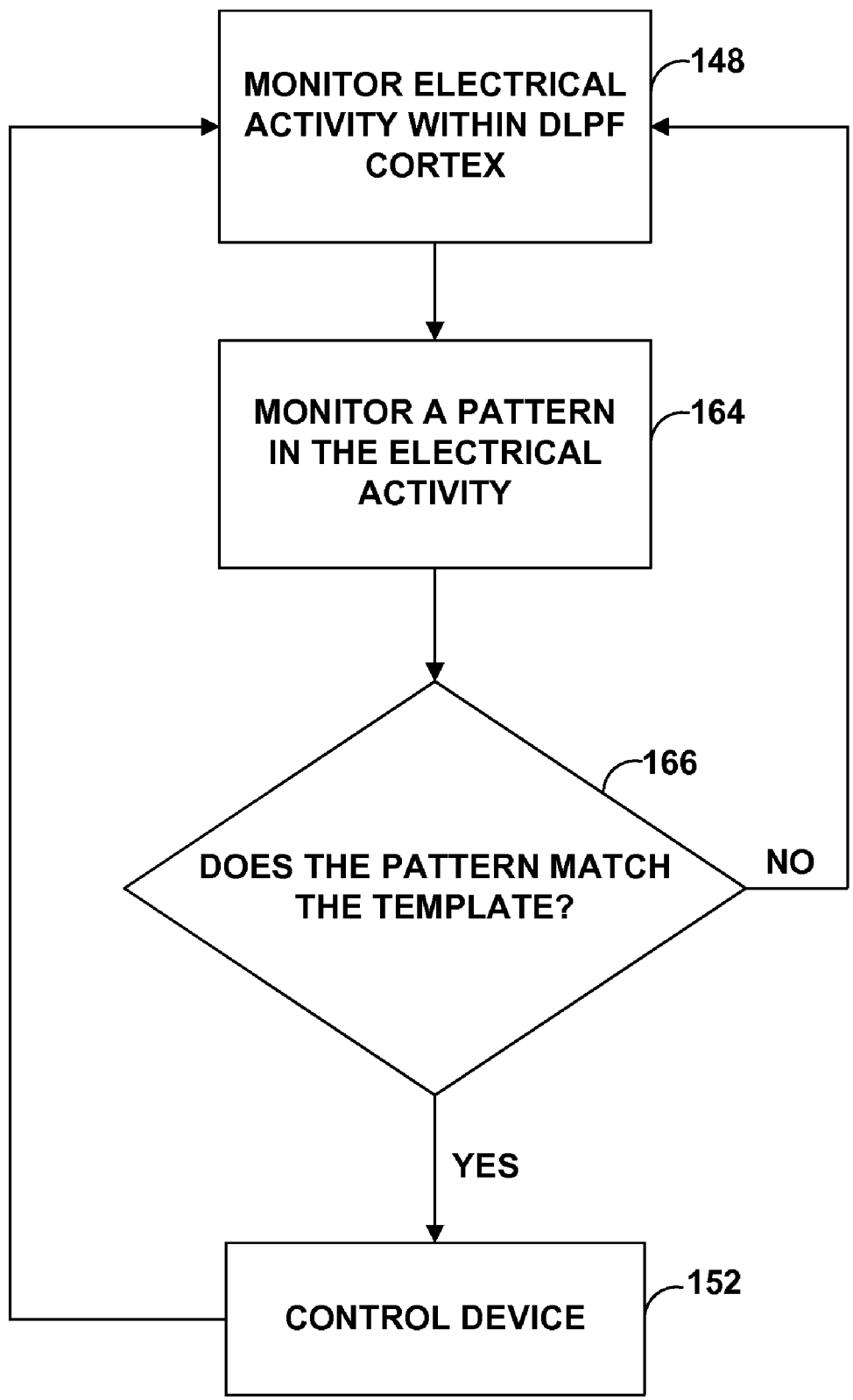
FIG. 19A is a flow diagram illustrating an example technique for analyzing electrical activity within the DLPF cortex to determine whether the activity indicates prospective patient movement.

FIG. 19A is a flow diagram illustrating an example technique for determining whether electrical signals within DLPF cortex 132 are indicative of prospective movement of patient 12. The method shown in FIG. 19A is similar to that shown in FIG. 18A, except that rather than comparing an amplitude of the measured electrical signal from within DLPF cortex 132 to a threshold value (154) and controlling a device if the amplitude of the measured signal is greater than or equal to the threshold value (156, 152), the technique shown in FIG. 19A involves monitoring a pattern (also referred to as a trend) in the amplitude of the measured electrical signal (164). In this way, the method may use signal analysis techniques, such as correlation, to monitor for prospective patient movement and implement a closed-looped system for controlling a device. In other examples, a trend in a signal characteristic other than the amplitude may be compared to a template.

Processor 72 may perform temporal correlation with a template by sampling the DLPF cortex signal with a sliding window and comparing the sampled waveform with a stored template waveform. For example, processor 72 may perform a correlation analysis by moving a window along a digitized plot of the amplitude waveform of a DLPF cortex signal at regular intervals, such as between about one millisecond to about ten millisecond intervals, to define a sample of the DLPF cortex signal. The sample window may be slid along the plot until a correlation is detected between the waveform of the template and the waveform of the sample of the DLPF cortex signal defined by the window. By moving the window at regular time intervals, multiple sample periods are defined. The correlation may be detected by, for example, matching multiple points between the template waveform and the waveform of the plot of the DLPF cortex signal over time, or by applying any suitable mathematical correlation algorithm between the sample in the sampling window and a corresponding set of samples stored in the template waveform.

If the pattern in the signal amplitude over time substantially matches a pattern template (166), processor 72 controls a device, e.g., initiates or adjusts therapy delivery to patient 12 to help patient 12 initiate movement or maintain movement (152). In some examples, the template matching algorithm that is employed to determine whether the pattern matches the template (166) may not require a one hundred percent (100%) correlation match, but rather may only match some percentage of the pattern. For example, if the amplitude waveform of the DLPF cortex signal exhibits a pattern that matches about 75% or more of the template, the algorithm employed by processor 72 within IMD 134 or external sensing device 14 may determine that there is a substantial match between the pattern and the template.

In one example, a pattern in the amplitude of the electrical signals from DLPF cortex 132 that is indicative prospective movement may represent a rate of change of the amplitude measurements over time. For example, a positive increase in the time rate of change (i.e., the slope or first derivative) of the signal amplitude may indicate patient 12 is intending to move. Accordingly, if the time rate of change of the amplitude measurements matches or exceeds the time rate of change of the template, processor 72 may control therapy module 36, external device 146 or another device (152). The exact trend that is indicative of prospective movement may be determined during a trial phase, which is described below with reference to FIG. 19B.

Figure 19B:
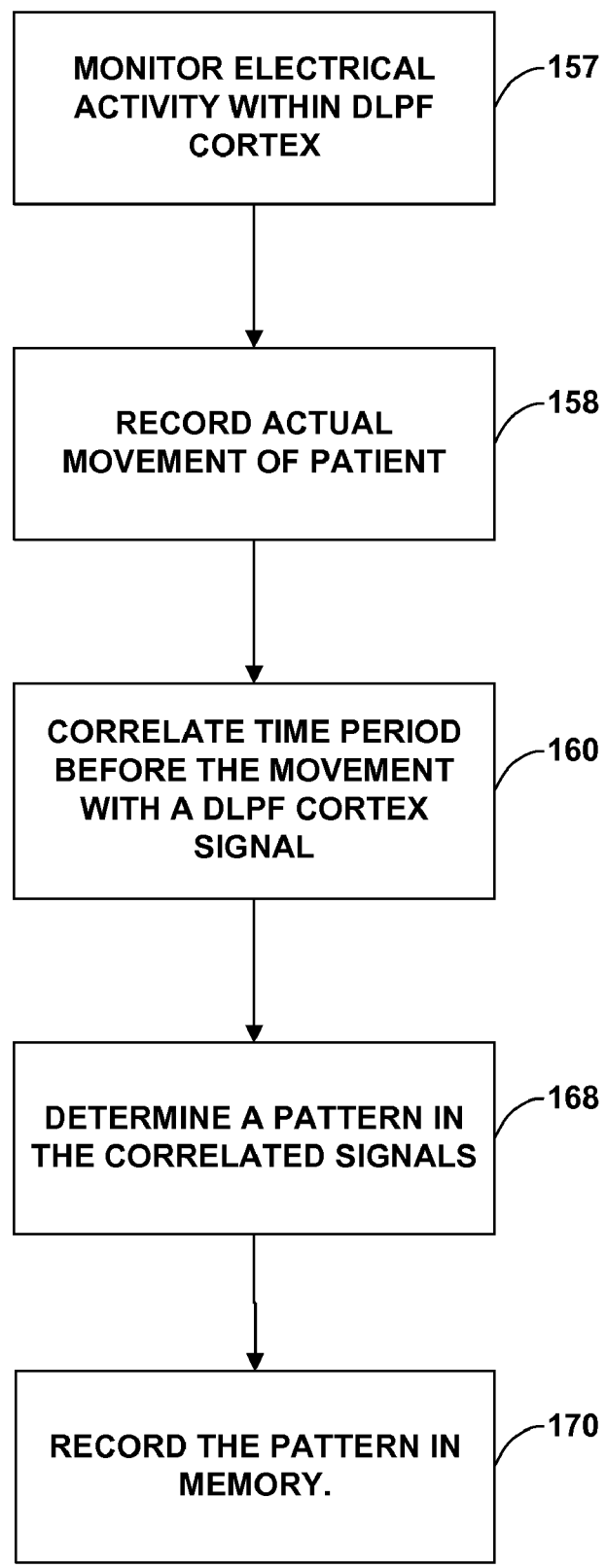
FIG. 19B is a flow diagram illustrating an example technique for determining one or more trend templates to compare to a pattern of amplitude measurements of electrical activity within the DLPF cortex in order to determining whether the electrical activity is indicative of prospective movement.

FIG. 19B is a flow diagram illustrating an example technique for determining one or more trend templates for determining whether a signal measured within DLPF cortex 132 is indicative of prospective patient movement. The technique shown in FIG. 19B is similar that shown in FIG. 18B, except that rather than associating actual movement with a specific amplitude value or range of amplitude values, a pattern of a characteristic of the signal is associated with an actual movement in order to generate a template. As with the threshold values, the trend in the amplitude or other characteristic that indicates prospective movement may differ depending on the patient. It is also believed that it is possible for the relevant trending data to be the same for two or more patients. In such a case, one or more previously generated trend templates may be a starting point for a clinician, who may adapt (or "calibrate" or "tune") the template to a particular patient.

In the technique shown in FIG. 19B, after correlating (or associating) an actual movement or actual attempted movement with electrical signals that were sensed within DLPF cortex 132 prior to the movement or attempted movement (160), a pattern in signals may be determined (168). As previously discussed, the trend may be a rate of change, i.e., slope, of the amplitude of the measured signals over time or a series of different slopes and transition points in an amplitude waveform.

A pattern may be determined (168) by any suitable means. In one example, the clinician may plot the amplitude of the relevant electrical signal over time and use the slope of the plot in the slope as the trend template. The clinician may review the amplitude waveforms associated with two or more recorded movements in order to confirm that the template is indicative of prospective movement. Alternatively, a computing device may generate the plot. In other examples, a pattern or trend other than a simple slope of the impedance measurements over time may define the template. For example, the template may include a series of different slopes and transition points in the amplitude waveform of the measured DLPF cortex signal. After determining the relevant trend in the electrical signals that indicates prospective patient movement, the clinician and/or computing device may record the trend in memory 76 (FIG. 15) of IMD 134 or another device, and the trend may define a template for determining prospective movements in the future.

While processing any electrical activity within DLPF cortex 132 may be useful, focusing on a specific frequency band of the sensed electrical activity may also yield useful information, and in some cases, more useful information. For example, frequency components of the electrical activity waveform of may be analyzed and compared to frequency components of a template waveform. As previously described, different frequency bands are associated with different activity in brain 20. Some frequency ranges may be more revealing of prospective patient movement than other frequency ranges. This concept may be applied to determining whether activity within the DLPF cortex 132 indicates the early signs of movement (i.e., prospective movement).

For example, sensing module 136 may monitor the electrical activity within DLPF cortex 132, and either sensing module 136 or processor 72 may tune the electrical data to a particular frequency in order to detect the power level (also referred to as the "energy" or an indication of the signal strength) within a low frequency band (e.g., the alpha or delta frequency band from Table 1), the power level with a high frequency band (e.g., the beta or high gamma frequency bands in Table 1) or both the power within the low and high frequency bands. The power level within the selected frequency band may be indicative of whether the DLPF cortex 132 activity is indicative of prospective patient movement. In some cases, the high gamma band component of the DLPF cortex 132 bioelectrical signal may be easier to extract than the alpha band component because the gamma band includes less noise than the alpha band. The noise may be due to, for example, other bioelectrical signals (e.g., an ECG signal).

Figure 20:
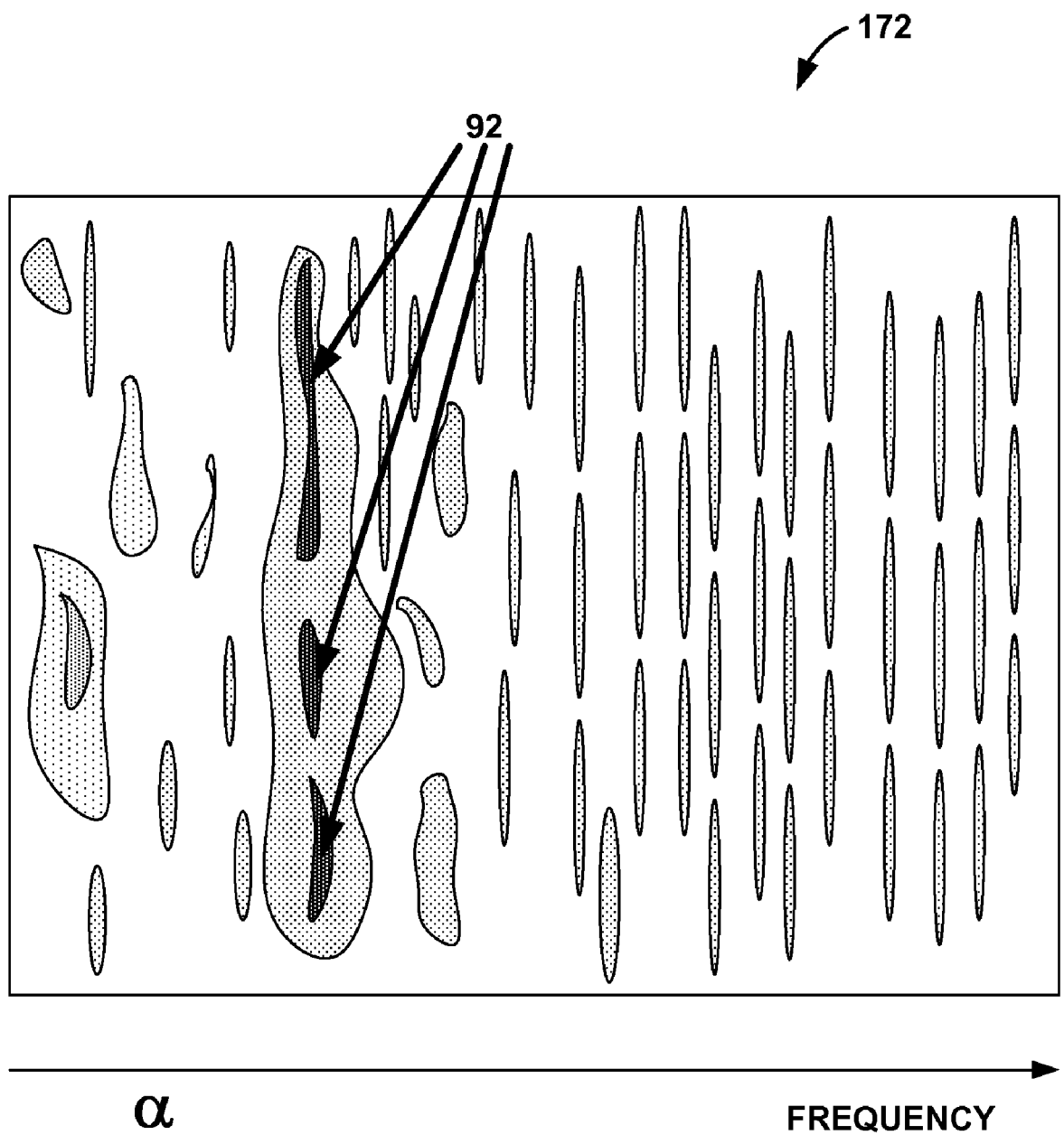
FIG. 20 is a conceptual frequency domain electroencephalogram plot taken by a sensor positioned near an occipital cortex of a human subject, and demonstrates that tuning to a particular frequency band may reveal more useful information about certain brain activity.

FIG. 20 illustrates a conceptual spectrogram 172 of the alpha ($\alpha$) band components of an EEG plot generated with external surface electrodes monitoring electrical activity within an occipital cortex of a brain of a human subject. Strong signals within the relatively low frequency band, i.e., the alpha band, as shown in regions 174 indicate that the activity within the alpha frequency band is high, and accordingly, the human subject is probably not executing thoughts of movement. The spectrogram shown in FIG. 20 may occur when, for example, a patient is sitting, sleeping, or otherwise stagnant. Strong signals falling within a relatively low frequency band, as shown via the spectrogram shown in FIG. 20, are not indicative of prospective movement.

Based on this relationship between the strength of the bioelectrical signals within brain 20 and a signal strength within a relatively low frequency band, in some examples, processor 72 of IMD 134 may determine whether the signal strength of the electrical activity sensed within DLPF cortex 132 within a relatively low frequency band is relatively low in order to determine whether the biosignal sensed within DLPF cortex 132 is indicative of prospective patient movement. A technique similar to the technique shown in FIG. 8 may be used by processor 72. As described above, FIG. 8 illustrates a technique for determining whether an EEG signal indicates patient 12 is in a movement state.

In some examples, a signal processor, e.g., within processor 72 of IMD 134, may analyze the strength of the monitored DLPF cortex signal within a relatively low frequency band (e.g., the alpha or delta frequency bands from Table 1 above). If the power level within the low frequency band is relatively low, the brain signals may indicate that the power level is ramping up to a higher frequency band (e.g., the beta or high gamma frequency bands from Table 1 above) and patient 12 is initiating thoughts of movement. Thus, a brain signal sensed within DLPF cortex 132 that includes a relatively low power level within a low frequency band may be indicative of prospective movement. Alternatively, processor 72 may determine whether the power within the low frequency band increased or decreased relatively quickly over time. A decrease in the power in the low frequency band may indicate patient 12 wants to initiate motion because the power level is ramping up to a higher frequency band, which is associated with prospective movement.

In response to detecting the signal indicative of prospective movement based on the power of the brain signal sensed within DLPF cortex 132 within one or more frequency bands, processor 72 may control a device, which may include therapy module 70 (FIG. 15) and/or control an external device 146 (FIG. 16). On the other hand, if the power of the brain signal sensed within DLPF cortex 132 in the lower frequency band is relatively high, patient 12 may not be initiating thoughts of movement, and processor 72 may not take any action, while sensing module 136 of IMD 134 may continue monitoring the activity within DLPF cortex 132.

In other examples, sensing module 136 may monitor the power level within a high frequency band (e.g., gamma or beta bands), and an increased power level in the high frequency band may indicate patient 12 is in the early stages of movement (e.g., patient 12 is thinking about moving). That is, a higher power level in a relatively high frequency band (e.g., beta or gamma frequency bands) may be a brain signal indicative of prospective movement of patient 12. In general, if the strong signals fall within a high frequency band (e.g., the beta or gamma bands from Table 1), or otherwise do not fall within the lower frequency band, therapy may be activated or adjusted to help patient 12 initiate and/or maintain movement. In some cases, sensing module 136 may monitor the power level within both the low and high frequency bands.

In each of the described examples in which processor 72 of IMD 134 controls therapy module 70 or external device 146 to initiate therapy delivery to patient 12 in response to detecting prospective movement of patient 12, the therapy delivery may be initiated for a predetermined amount of time or until processor 72 receives an indication that patient 12 has stopped moving. In the case of a movement disorder, it may be useful to deliver therapy to patient 12 for a defined period of time, rather than substantially continuously, in order to help patient 12 initiate movement, while conserving power source 78 of IMD 134 (FIG. 15).

Similarly, in examples in which processor 72 controls therapy module 70 or external device 146 to adjust therapy delivery in response to detecting prospective movement of patient 12 based on brain signals sensed within DLPF cortex 132, therapy module 70 or external device 146 may continue delivering therapy at an adjusted level for a predetermined amount of time or until processor 72 receives an indication that patient 12 has initiated movement or stopped moving. The predetermined amount of time may be selected to be sufficient to initiate patient movement or otherwise control a movement disorder. For example, if initiation of patient movement is desired (e.g., to treat hypokinesia), the predetermined amount of time may be relatively short (e.g., less than five seconds). As another example, if functional electrical stimulation to help increase an execution of a movement (e.g., to treat bradykinesia) is desired, the predetermined amount of time may be relatively long (e.g., on the duration of minutes).

As previously indicated, an indication that patient 12 has initiated movement or stopped moving may be generated any suitable way. For example, processor 72 may receive a signal from a motion sensor (e.g., an accelerometer) that is placed to detect actual movement of patient 12, and, accordingly, may detect the cessation of movement. The motion sensor may be, for example, integrated with IMD 134, external device 146, implanted within an arm or leg of patient 12 or otherwise carried externally (e.g., on a belt or arm band). The brain signals detected within DLPF cortex 132 may be used to make relatively fast and responsive adjustments to therapy, whereas the motion sensor may also be used to make longer term adjustments to therapy based, as described above with respect to FIG. 12.

As another example, processor 72 may analyze a brain signal from within DLPF cortex 132 to determine if patient 12 is no longer executing thoughts of movement. For example, if the amplitude of the signal falls below an amplitude threshold or longer matches a template, the brain signal may indicate patient 12 is no longer executing thoughts of movement. In other examples, the ratio of the power level in particular frequency bands (e.g., delta/gamma) may be compared to a threshold value to determine whether a brain signal from within DLPF cortex 132 indicates prospective movement of patient 12.

In another example, the correlation of changes of power between two or more frequency bands may be compared to a stored value to determine whether the signal from DLPF cortex 132 indicates patient 12 is in a movement state or in a rest state (i.e., not in the movement state). For example, if the power level within the alpha band decreases and indicates prospective movement of patient 12, and within a certain amount of time or at substantially the same time, the power level within the high gamma band of the DLPF cortex signal increases, processor 72 may confirm that patient 12 is intending on moving. This correlation of changes in power of different frequency bands may be implemented into an algorithm that helps processor 72 eliminate false positives of the prospective movement detection, i.e., by providing confirmation that the low power level (e.g., as compared to a stored value or trend template) within the alpha band or high power level within the gamma band (e.g., as compared to a stored value or trend template) indicates prospective movement state.

Figure 21:
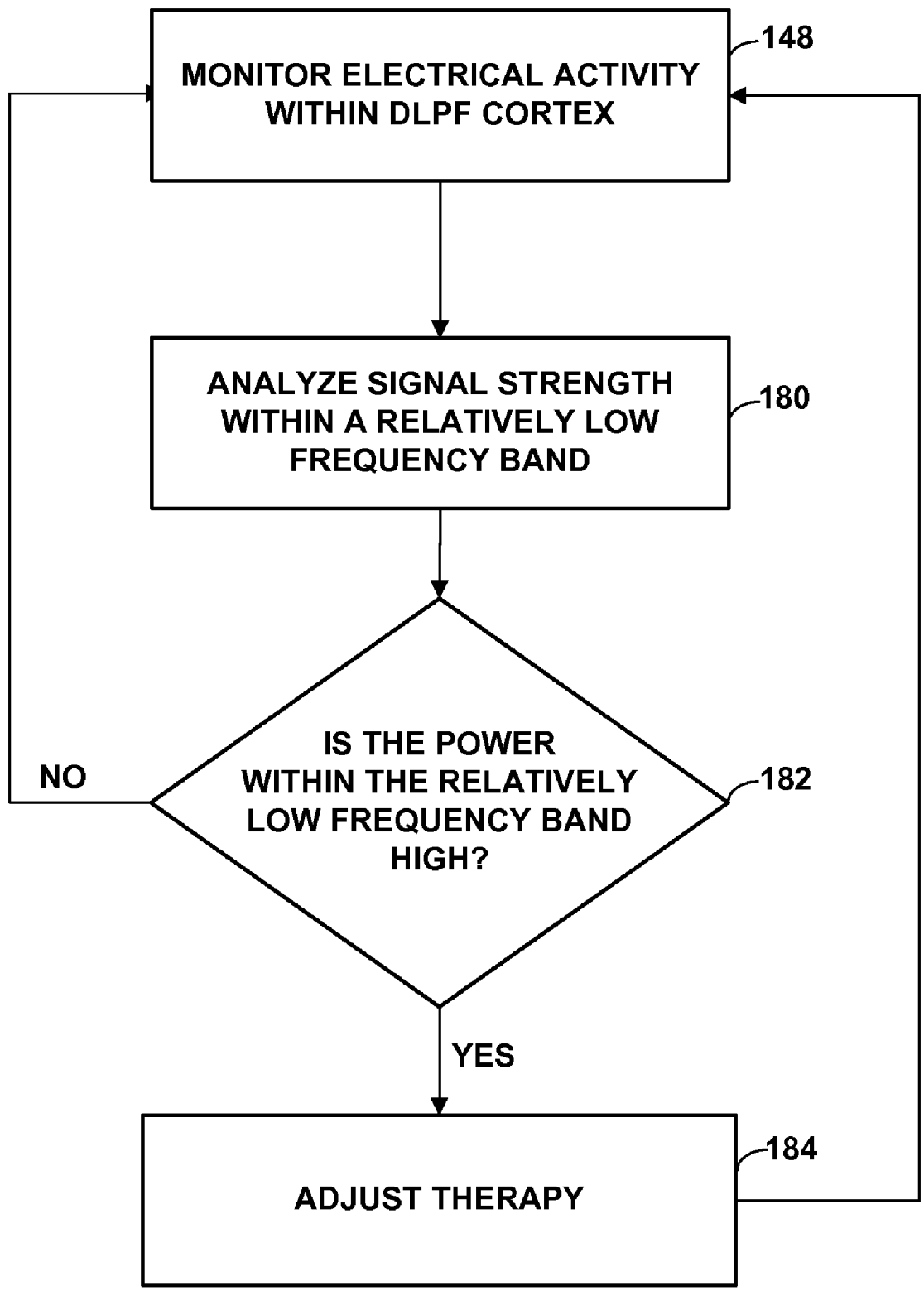
FIG. 21 is flow diagram of an example technique for controlling therapy delivery based on one or more frequency characteristics of a brain signal within a DLPF cortex of a patient.

FIG. 21 illustrates an example technique that processor 72 may implement to deactivate or adjust therapy after initiating or adjusting therapy in response to detecting a brain signal within DLPF cortex 132 that is indicative of prospective movement. Sensing module 136 of IMD 134 may monitor activity with DLPF cortex 132 (148) and processor 72 may receive the DLPF cortex signal from sensing module 136 and analyze a strength of the signal within a relatively low frequency band (180), such as an alpha band. Rather than determining whether the power level within the lower frequency band is low, processor 72 may determine whether the power within the relatively low frequency band is high (182), which may indicate that patient 12 is no longer moving or initiating thoughts of movement. If the power level within the low frequency band is high (180), processor 72 may adjust therapy (184), such as by terminating therapy or decreasing the intensity of therapy by adjusting one or more therapy parameter values. Alternatively, processor 72 may focus on the power level within a high frequency band, and a relatively low power level in the high frequency band may indicate a lack of prospective movement.

Figure 22:
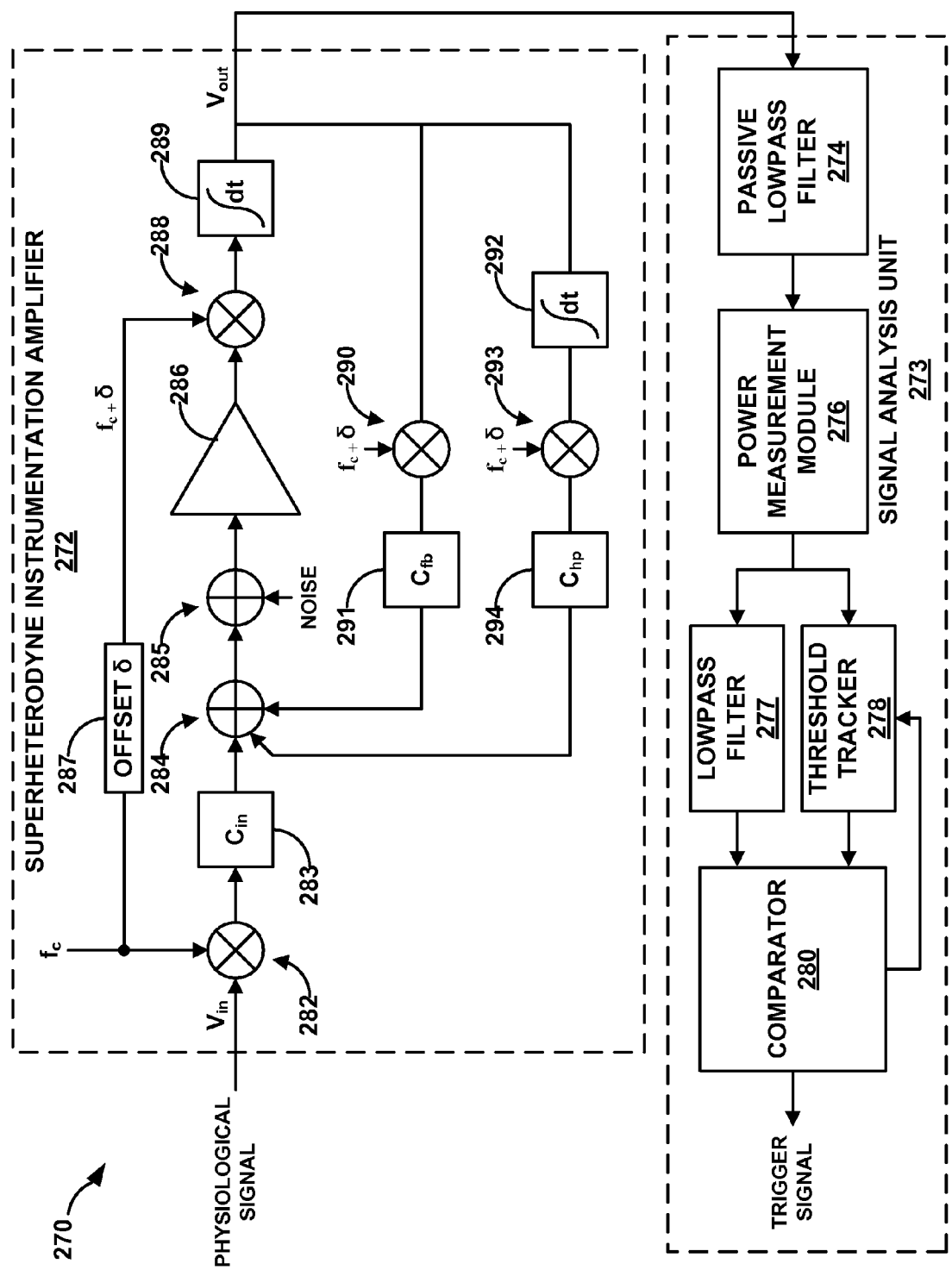
FIG. 22 is a block diagram illustrating an example frequency selective signal monitor that includes a chopper-stabilized superheterodyne amplifier and a signal analysis unit.

FIG. 22 is a block diagram illustrating an exemplary frequency selective signal monitor 270 that includes a chopper-stabilized superheterodyne instrumentation amplifier 272 and a signal analysis unit 273. Amplifier 272 is described in further detail in commonly-assigned U.S. Provisional Application No. 60/975,372 to Denison et al., entitled "FREQUENCY SELECTIVE MONITORING OF PHYSIOLOGICAL SIGNALS," and filed on Sep. 26, 2007, commonly-assigned U.S. Provisional Application No. 61/025,503 to Denison et al., entitled "FREQUENCY SELECTIVE MONITORING OF PHYSIOLOGICAL SIGNALS", and filed on Feb. 1, 2008, and commonly-assigned U.S. Provisional Application No. 61/083,381, entitled, "FREQUENCY SELECTIVE EEG SENSING CIRCUITRY," and filed on Jul. 24, 2008. The entire contents of above-identified U.S. Provisional Application Nos. 60/975,372, 61/025,503, and 61/083,381 are incorporated herein by reference. Amplifier 272 is also described in further detail in commonly-assigned U.S. patent application Ser. No. 12/237,868 to Denison et al., entitled, "FREQUENCY SELECTIVE MONITORING OF PHYSIOLOGICAL SIGNALS" and filed on the same date as the present disclosure. U.S. patent application Ser. No. 12/237,868 to Denison et al., is incorporated herein by reference in its entirety.

Signal monitor 270 may utilize a heterodyning, chopper-stabilized amplifier architecture to convert a selected frequency band of a physiological signal to a baseband for analysis. The physiological signal may be analyzed in one or more selected frequency bands to trigger therapy delivery to patient 12, trigger adjustment to therapy delivery, and/or trigger recording of diagnostic information. In some cases, signal monitor 270 may be utilized within a separate sensor that communicates with a medical device. For example, signal monitor 270 may be utilized within sensing device 14 positioned external to patient 12 and coupled to external cue device 16 (FIG. 1A). In other examples, signal monitor 270 may be included within an external or implanted medical device, such as IMD 62 (FIG. 5) or sensing module 136 of IMD 134 (FIG. 15).

In general, frequency selective signal monitor 270 provides a physiological signal monitoring device comprising a physiological sensing element that receives a physiological signal, an instrumentation amplifier 272 comprising a modulator 282 that modulates the signal at a first frequency, an amplifier that amplifies the modulated signal, and a demodulator 288 that demodulates the amplified signal at a second frequency different from the first frequency. A signal analysis unit 273 that analyzes a characteristic of the signal in the selected frequency band. The second frequency is selected such that the demodulator substantially centers a selected frequency band of the signal at a baseband.

The signal analysis unit 273 may comprise a lowpass filter 274 that filters the demodulated signal to extract the selected frequency band of the signal at the baseband. The second frequency may differ from the first frequency by an offset that is approximately equal to a center frequency of the selected frequency band. In one example, the physiological signal is an EEG signal and the selected frequency band is one of an alpha, beta or gamma frequency band of the EEG signal. The characteristic of the demodulated signal is power fluctuation of the signal in the selected frequency band. The signal analysis unit 273 may generate a signal triggering at least one of control of therapy to the patient or recording of diagnostic information when the power fluctuation exceeds a threshold.

In some examples, the selected frequency band comprises a first selected frequency band and the characteristic comprises a first power. The demodulator 288 demodulates the amplified signal at a third frequency different from the first and second frequencies. The third frequency being selected such that the demodulator 288 substantially centers a second selected frequency band of the signal at a baseband. The signal analysis unit 273 analyzes a second power of the signal in the second selected frequency band, and calculates a power ratio between the first power and the second power. The signal analysis unit 273 generates a signal triggering at least one of control of therapy to the patient or recording of diagnostic information based on the power ratio.

In the example of FIG. 22, chopper-stabilized, superheterodyne amplifier 272 modulates the physiological signal with a first carrier frequency $f_c$, amplifies the modulated signal, and demodulates the amplified signal to baseband with a second frequency equivalent to the first frequency $f_c$ plus (or minus) an offset δ. Signal analysis unit 273 measures a characteristic of the demodulated signal in a selected frequency band.

The second frequency is different from the first frequency $f_c$ and is selected, via the offset δ, to position the demodulated signal in the selected frequency band at the baseband. In particular, the offset may be selected based on the selected frequency band. For example, the frequency band may be a frequency within the selected frequency band, such as a center frequency of the band.

If the selected frequency band is 5 to 15 Hz, for example, the offset δ may be the center frequency of this band, i.e., 10 Hz. In some examples, the offset δ may be a frequency elsewhere in the selected frequency band. However, the center frequency generally will be preferred. The second frequency may be generated by shifting the first frequency by the offset amount. Alternatively, the second frequency may be generated independently of the first frequency such that the difference between the first and second frequencies is the offset.

In either case, the second frequency may be equivalent to the first frequency $f_c$ plus or minus the offset δ. If the first frequency $f_c$ is 4000 Hz, for example, and the selected frequency band is 5 to 15 Hz (the alpha band for EEG signals), the offset δ may be selected as the center frequency of that band, i.e., 10 Hz. In this case, the second frequency is the first frequency of 4000 Hz plus or minus 10 Hz. Using the superheterodyne structure, the signal is modulated at 4000 Hz by modulator 282, amplified by amplifier 286 and then demodulated by demodulator 288 at 3990 or 4010 Hz (the first frequency $f_c$ of 4000 Hz plus or minus the offset δ of 10 Hz) to position the 5 to 15 Hz band centered at 10 Hz at baseband, e.g., DC. In this manner the 5 to 15 Hz band can be directly downconverted such that it is substantially centered at DC.

As illustrated in FIG. 22, superheterodyne instrumentation amplifier 272 receives a physiological signal (e.g., $V_{in}$) from sensing elements positioned at a desired location within a patient or external to a patient to detect the physiological signal. For example, the physiological signal may comprise one of an EEG, ECoG, EMG, EDG, pressure, temperature, impedance or motion signal. Again, an EEG signal will be described for purposes of illustration. Superheterodyne instrumentation amplifier 272 may be configured to receive the physiological signal ($V_{in}$) as either a differential or signal-ended input. Superheterodyne instrumentation amplifier 272 includes first modulator 282 for modulating the physiological signal from baseband at the carrier frequency ($f_c$). In the example of FIG. 22, an input capacitance ($C_{in}$) 283 couples the output of first modulator 282 to feedback adder 284. Feedback adder 284 will be described below in conjunction with the feedback paths.

Adder 285 represents the inclusion of a noise signal with the modulated signal. Adder 285 represents the addition of low frequency noise, but does not form an actual component of superheterodyne instrumentation amplifier 272. Adder 285 models the noise that comes into superheterodyne instrumentation amplifier 272 from non-ideal transistor characteristics. At adder 285, the original baseband components of the signal are located at the carrier frequency $f_c$. As an example, the baseband components of the signal may have a frequency within a range of 0 to approximately 1000 Hz and the carrier frequency $f_c$ may be approximately 4 kHz to approximately 10 kHz. The noise signal enters the signal pathway, as represented by adder 285, to produce a noisy modulated signal. The noise signal may include 1/f noise, popcorn noise, offset, and any other external signals that may enter the signal pathway at low (baseband) frequency. At adder 285, however, the original baseband components of the signal have already been chopped to a higher frequency band, e.g., 4000 Hz, by first modulator 282. Thus, the low-frequency noise signal is segregated from the original baseband components of the signal.

Amplifier 286 receives the noisy modulated input signal from adder 285. Amplifier 286 amplifies the noisy modulated signal and outputs the amplified signal to a second modulator 288. Offset (δ) 287 may be tuned such that it is approximately equal to a frequency within the selected frequency band, and preferably the center frequency of the selected frequency band. The resulting modulation frequency ($f_c \pm \delta$) used by demodulator 288 is then different from the first carrier frequency $f_c$ by the offset amount δ. In some cases, offset δ 287 may be manually tuned according to the selected frequency band by a physician, technician, or the patient. In other cases, the offset δ 287 may by dynamically tuned to the selected frequency band in accordance with stored frequency band values. For example, different frequency bands may be scanned by automatically or manually tuning the offset δ according to center frequencies of the desired bands. As an example, when monitoring akinesia, the selected frequency band may be the alpha frequency band (5 Hz to 15 Hz). In this case, the offset δ may be approximately the center frequency of the alpha band, i.e., 10 Hz. As another example, when monitoring tremor, the selected frequency band may be the beta frequency band (15 Hz-35 Hz). In this case, the offset δ may be approximately the center frequency of the beta band, i.e., 25 Hz.

As another example, when monitoring intent in the cortex, the selected frequency band may be the high gamma frequency band (100 Hz-200 Hz). In this case, the offset δ may be approximately the center frequency of the high gamma band, i.e., 175 Hz. When monitoring pre-seizure biomarkers in epilepsy, the selected frequency may be fast ripples (500 Hz), in which case the offset δ may be approximately 500 Hz. As another illustration, the selected frequency band passed by filter 234 may be the gamma band (30 Hz-80 Hz), in which case the offset δ may be tuned to approximately the center frequency of the gamma band, i.e., 55 Hz.

Hence, the signal in the selected frequency band may be produced by selecting the offset (δ) 287 such that the carrier frequency plus or minus the offset frequency ($f_c \pm \delta$) is equal to a frequency within the selected frequency band, such as the center frequency of the selected frequency band. In each case, as explained above, the offset may be selected to correspond to the desired band. For example, an offset of 5 Hz would place the alpha band at the baseband frequency, e.g., DC, upon downconversion by the demodulator. Similarly, an offset of 15 Hz would place the beta band at DC upon downconversion, and an offset of 30 Hz would place the gamma band at DC upon downconversion. In this manner, the pertinent frequency band is centered at the baseband. Then, passive low pass filtering may be applied to select the frequency band. In this manner, the superheterodyne architecture serves to position the desired frequency band at baseband as a function of the selected offset frequency used to produce the second frequency for demodulation. In general, in the example of FIG. 22, powered bandpass filtering is not required. Likewise, the selected frequency band can be obtained without the need for oversampling and digitization of the wideband signal.

With further reference to FIG. 22, second modulator 288 demodulates the amplified signal at the second frequency $f_c \pm \delta$, which is separated from the carrier frequency $f_c$ by the offset δ. That is, second modulator 288 modulates the noise signal up to the $f_c \pm \delta$ frequency and demodulates the components of the signal in the selected frequency band directly to baseband. Integrator 289 operates on the demodulated signal to pass the components of the signal in the selected frequency band positioned at baseband and substantially eliminate the components of the noise signal at higher frequencies. In this manner, integrator 289 provides compensation and filtering to the amplified signal to produce an output signal ($V_{out}$). In other examples, compensation and filtering may be provided by other circuitry.

As shown in FIG. 22, superheterodyne instrumentation amplifier 272 may include two negative feedback paths to feedback adder 284 to reduce glitching in the output signal ($V_{out}$). In particular, the first feedback path includes a third modulator 290, which modulates the output signal at the carrier frequency plus or minus the offset δ, and a feedback capacitance ($C_{fb}$) 291 that is selected to produce desired gain given the value of the input capacitance ($C_{in}$) 283. The first feedback path produces a feedback signal that is added to the original modulated signal at feedback adder 284 to produce attenuation and thereby generate gain at the output of amplifier 286.

The second feedback path may be optional, and may include an integrator 292, a fourth modulator 293, which modulates the output signal at the carrier frequency plus or minus the offset δ, and high pass filter capacitance ($C_{hp}$) 294. Integrator 292 integrates the output signal and modulator 293 modulates the output of integrator 292 at the carrier frequency. High pass filter capacitance ($C_{hp}$) 294 is selected to substantially eliminate components of the signal that have a frequency below the corner frequency of the high pass filter. For example, the second feedback path may set a corner frequency of approximately equal to 2.5 Hz, 0.5 Hz, or 0.05 Hz. The second feedback path produces a feedback signal that is added to the original modulated signal at feedback adder 284 to increase input impedance at the output of amplifier 286.

As described above, chopper-stabilized, superheterodyne instrumentation amplifier 272 can be used to achieve direct downconversion of a selected frequency band centered at a frequency that is offset from baseband by an amount δ. Again, if the alpha band is centered at 10 Hz, then the offset amount δ used to produce the demodulation frequency $f_c \pm \delta$ may be 10 Hz. As illustrated in FIG. 22, first modulator 282 is run at the carrier frequency ($f_c$), which is specified by the 1/f corner and other constraints, while second modulator 288 is run at the selected frequency band ($f_c \pm \delta$). Multiplication of the physiological signal by the carrier frequency convolves the signal in the frequency domain. The net effect of upmodulation is to place the signal at the carrier frequency ($f_c$). By then running second modulator 288 at a different frequency ($f_c \pm \delta$), the convolution of the signal sends the signal in the selected frequency band to baseband and 2δ. Integrator 289 may be provided to filter out the 2δ component and passes the baseband component of the signal in the selected frequency band.

As illustrated in FIG. 22, signal analysis unit 273 receives the output signal from instrumentation amplifier. In the example of FIG. 22, signal analysis unit 273 includes a passive lowpass filter 274, a power measurement module 276, a lowpass filter 277, a threshold tracker 278 and a comparator 280. Passive lowpass filter 274 extracts the signal in the selected frequency band positioned at baseband. For example, lowpass filter 274 may be configured to reject frequencies above a desired frequency, thereby preserving the signal in the selected frequency band. Power measurement module 276 then measures power of the extracted signal. In some cases, power measurement module 276 may extract the net power in the desired band by full wave rectification. In other cases, power measurement module 276 may extract the net power in the desired band by a squaring power calculation, which may be provided by a squaring power circuit. As the signal has sine and cosine phases, summing of the squares yields a net of 1 and the total power. The measured power is then filtered by lowpass filter 277 and applied to comparator 280. Threshold tracker 278 tracks fluctuations in power measurements of the selected frequency band over a period of time in order to generate a baseline power threshold of the selected frequency band for the patient. Threshold tracker 278 applies the baseline power threshold to comparator 280 in response to receiving the measured power from power measurement module 276.

Comparator 280 compares the measured power from lowpass filter 277 with the baseline power threshold from threshold tracker 278. If the measured power is greater than the baseline power threshold, comparator 280 may output a trigger signal to a processor of a medical device to control therapy and/or recording of diagnostic information. If the measured power is equal to or less than the baseline power threshold, comparator 280 outputs a power tracking measurement to threshold tracker 278, as indicated by the line from comparator 280 to threshold tracker 278. Threshold tracker 278 may include a median filter that creates the baseline threshold level after filtering the power of the signal in the selected frequency band for several minutes. In this way, the measured power of the signal in the selected frequency band may be used by the threshold tracker 278 to update and generate the baseline power threshold of the selected frequency band for the patient. Hence, the baseline power threshold may be dynamically adjusted as the sensed signal changes over time. A signal above or below the baseline power threshold may signify an event that may support generation of a trigger signal.

In some cases, frequency selective signal monitor 270 may be limited to monitoring a single frequency band of the wide band physiological signal at any specific instant. Alternatively, frequency selective signal monitor 270 may be capable of efficiently hopping frequency bands in order to monitor the signal in a first frequency band, monitor the signal in a second frequency band, and then determine whether to trigger therapy and/or diagnostic recording based on some combination of the monitored signals. For example, different frequency bands may be monitored on an alternating basis to support signal analysis techniques that rely on comparison or processing of characteristics associated with multiple frequency bands.

In some examples, the circuit of FIG. 22 may be modified to further incorporate a nested chopper architecture having an outer chopper and an inner chopper. The inner chopper may operate as a superheterodyning chopper (e.g., with modulation and demodulation frequencies of $f_c$ and $f_c \pm \delta$, respectively) while the outer chopper may operate as a basic chopper with modulation and demodulation frequencies both at $f_c/m$, where $f_c/m$ is lower than $f_c$. The addition of an outer chopper to form a nested chopper may be helpful in suppressing intermodulation.

Figure 23:
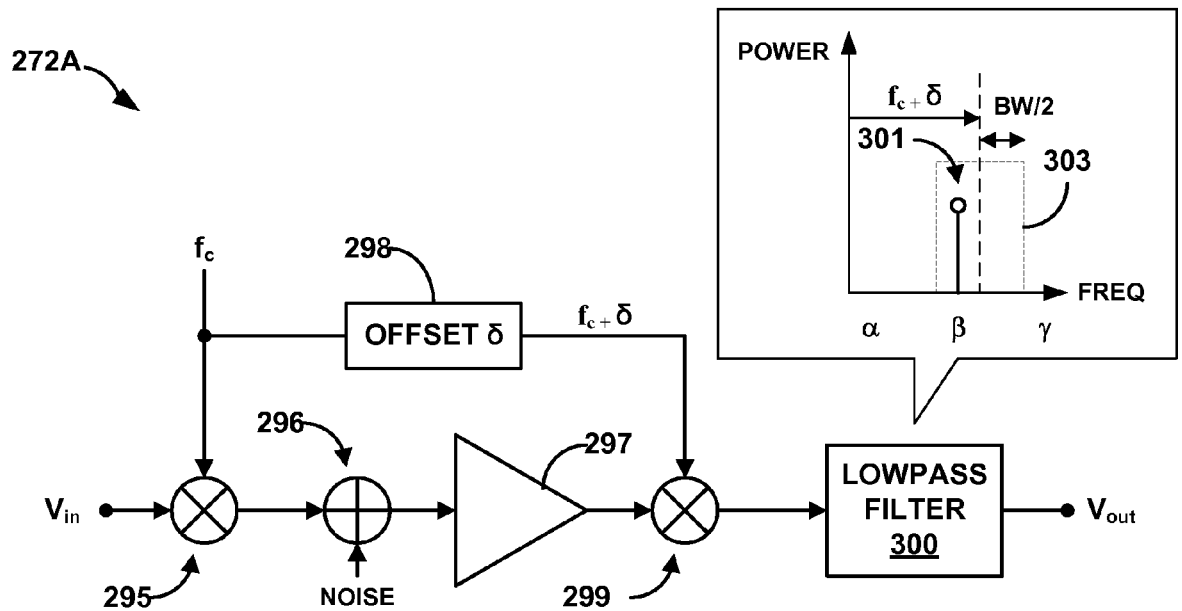
FIG. 23 is a block diagram illustrating a portion of an example chopper-stabilized superheterodyne amplifier that may be used within the frequency selective signal monitor from FIG. 22.

FIG. 23 is a block diagram illustrating a portion of an exemplary chopper-stabilized superheterodyne instrumentation amplifier 272A for use within frequency selective signal monitor 270 from FIG. 22. Superheterodyne instrumentation amplifier 272A illustrated in FIG. 23 may operate substantially similar to superheterodyne instrumentation amplifier 272 from FIG. 22. Superheterodyne instrumentation amplifier 272A includes a first modulator 295, an amplifier 297, a frequency offset 298, a second modulator 299, and a lowpass filter 300. In some examples, lowpass filter 300 may be an integrator, such as integrator 289 of FIG. 22. Adder 296 represents addition of noise to the chopped signal. However, adder 296 does not form an actual component of superheterodyne instrumentation amplifier 272A. Adder 296 models the noise that comes into superheterodyne instrumentation amplifier 272A from non-ideal transistor characteristics.

Superheterodyne instrumentation amplifier 272A receives a physiological signal ($V_{in}$) associated with a patient from sensing elements, such as electrodes, positioned within or external to the patient to detect the physiological signal. First modulator 295 modulates the signal from baseband at the carrier frequency ($f_c$). A noise signal is added to the modulated signal, as represented by adder 296. Amplifier 297 amplifies the noisy modulated signal. Frequency offset 298 is tuned such that the carrier frequency plus or minus frequency offset 298 ($f_c \pm \delta$) is equal to the selected frequency band.

Hence, the offset δ may be selected to target a desired frequency band. Second modulator 299 modulates the noisy amplified signal at offset frequency 98 from the carrier frequency $f_c$. In this way, the amplified signal in the selected frequency band is demodulated directly to baseband and the noise signal is modulated to the selected frequency band.

Lowpass filter 300 may filter the majority of the modulated noise signal out of the demodulated signal and set the effective bandwidth of its passband around the center frequency of the selected frequency band. As illustrated in the detail associated with lowpass filter 300 in FIG. 23, a passband 303 of lowpass filter 300 may be positioned at a center frequency of the selected frequency band. In some cases, the offset δ may be equal to this center frequency. Lowpass filter 300 may then set the effective bandwidth (BW/2) of the passband around the center frequency such that the passband encompasses the entire selected frequency band. In this way, lowpass filter 300 passes a signal 301 positioned anywhere within the selected frequency band. For example, if the selected frequency band is 5 to 15 Hz, for example, the offset δ may be the center frequency of this band, i.e., 10 Hz, and the effective bandwidth may be half the full bandwidth of the selected frequency band, i.e., 5 Hz. In this case, lowpass filter 300 rejects or at least attenuates signals above 5 Hz, thereby limiting the passband signal to the alpha band, which is centered at 0 Hz as a result of the superheterodyne process. Hence, the center frequency of the selected frequency band can be specified with the offset δ, and the bandwidth BW of the passband can be obtained independently with the lowpass filter 300, with BW/2 about each side of the center frequency.

Lowpass filter 300 then outputs a low-noise physiological signal ($V_{out}$). The low-noise physiological signal may then be input to signal analysis unit 273 from FIG. 22. As described above, signal analysis unit 273 may extract the signal in the selected frequency band positioned at baseband, measure power of the extracted signal, and compare the measured power to a baseline power threshold of the selected frequency band to determine whether to trigger patient therapy.

Figure 24A:
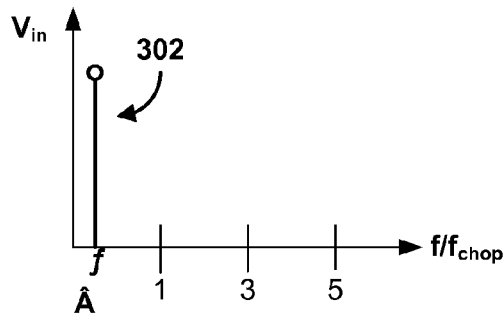
FIGS. 24A-24D are graphs illustrating the frequency components of a signal at various stages within the superheterodyne amplifier of FIG. 23.

FIGS. 24A-24D are graphs illustrating the frequency components of a signal at various stages within superheterodyne instrumentation amplifier 272A of FIG. 23. In particular, FIG. 24A illustrates the frequency components in a selected frequency band within the physiological signal received by frequency selective signal monitor 270. The frequency components of the physiological signal are represented by line 302 and located at offset δ from baseband in FIG. 24A.

Figure 24B:
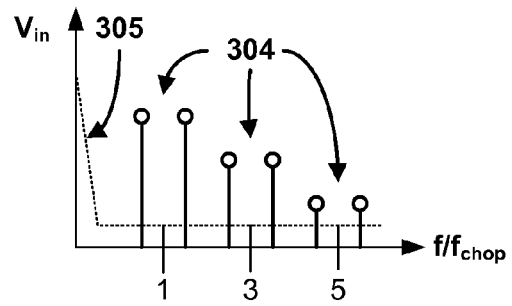

FIG. 24B illustrates the frequency components of the noisy modulated signal produced by modulator 295 and amplifier 297. In FIG. 24B, the original offset frequency components of the physiological signal have been up-modulated at carrier frequency $f_c$ and are represented by lines 304 at the odd harmonics. The frequency components of the noise signal added to the modulated signal are represented by dotted line 305. In FIG. 24B, the energy of the frequency components of the noise signal is located substantially at baseband and energy of the frequency components of the desired signal is located at the carrier frequency ($f_c$) plus and minus frequency offset (δ) 298 and its odd harmonics.

Figure 24C:
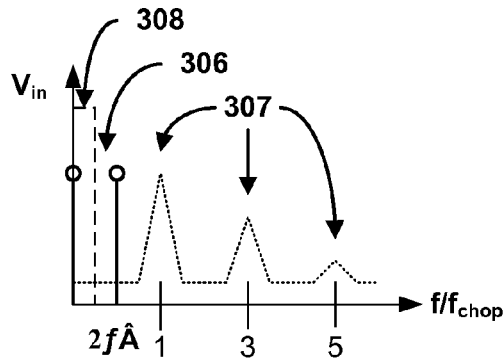

FIG. 24C illustrates the frequency components of the demodulated signal produced by demodulator 299. In particular, the frequency components of the demodulated signal are located at baseband and at twice the frequency offset (2δ), represented by lines 306. The frequency components of the noise signal are modulated and represented by dotted line 307. The frequency components of the noise signal are located at the carrier frequency plus or minus the offset frequency (δ) 298 and its odd harmonics in FIG. 24C. FIG. 24C also illustrates the effect of lowpass filter 300 that may be applied to the demodulated signal. The passband of lowpass filter 300 is represented by dashed line 308.

Figure 24D:
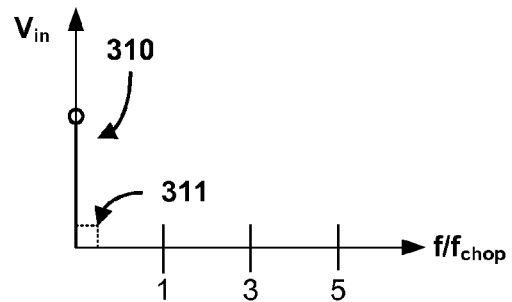

FIG. 24D is a graph that illustrates the frequency components of the output signal. In FIG. 24D, the frequency components of the output signal are represented by line 310 and the frequency components of the noise signal are represented by dotted line 311. FIG. 24D illustrates that lowpass filter 300 removes the frequency components of the demodulated signal located at twice the offset frequency (2δ). In this way, lowpass filter 300 positions the frequency components of the signal at the desired frequency band within the physiological signal at baseband. In addition, lowpass filter 300 removes the frequency components from the noise signal that were located outside of the passband of lowpass filter 300 shown in FIG. 24C. The energy from the noise signal is substantially eliminated from the output signal, or at least substantially reduced relative to the original noise signal that otherwise would be introduced.

Figure 25:
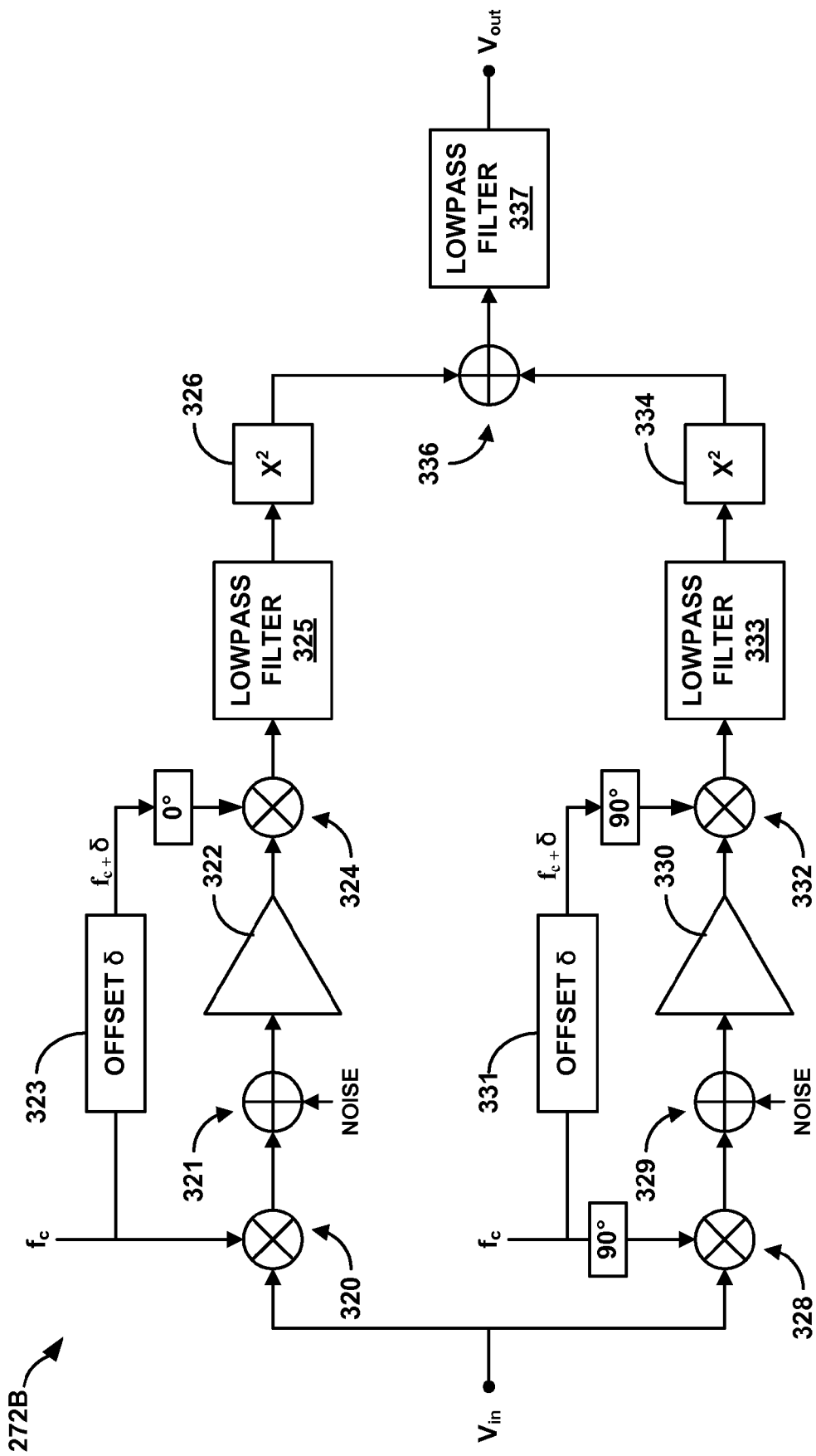
FIG. 25 is a block diagram illustrating a portion of an example chopper-stabilized superheterodyne amplifier with in-phase and quadrature signal paths for use within a frequency selective signal monitor.

FIG. 25 is a block diagram illustrating a portion of an exemplary chopper-stabilized superheterodyne instrumentation amplifier 272B with in-phase and quadrature signal paths for use within frequency selective signal monitor 270 from FIG. 22. The in-phase and quadrature signal paths substantially reduce phase sensitivity within superheterodyne instrumentation amplifier 272B. Because the signal obtained from the patient and the clocks used to produce the modulation frequencies are uncorrelated, the phase of the signal should be taken into account. To address the phasing issue, two parallel heterodyning amplifiers may be driven with in-phase (I) and quadrature (Q) clocks created with on-chip distribution circuits. Net power extraction then can be achieved with superposition of the in-phase and quadrature signals.

An analog implementation may use an on-chip self-cascoded Gilbert mixer to calculate the sum of squares. Alternatively, a digital approach may take advantage of the low bandwidth of the I and Q channels after lowpass filtering, and digitize at that point in the signal chain for digital power computation. Digital computation at the I/Q stage has advantages. For example, power extraction is more linear than a tan h function. In addition, digital computation simplifies offset calibration to suppress distortion, and preserves the phase information for cross-channel coherence analysis. With either technique, a sum of squares in the two channels can eliminate the phase sensitivity between the physiological signal and the modulation clock frequency. The power output signal can lowpass filtered to the order of 1 Hz to track the essential dynamics of a desired biomarker.

Superheterodyne instrumentation amplifier 272B illustrated in FIG. 25 may operate substantially similar to superheterodyne instrumentation amplifier 272 from FIG. 22. Superheterodyne instrumentation amplifier 272B includes an in-phase (I) signal path with a first modulator 320, an amplifier 322, an in-phase frequency offset (δ) 323, a second modulator 324, a lowpass filter 325, and a squaring unit 326. Adder 321 represents addition of noise. Adder 321 models the noise from non-ideal transistor characteristics. Superheterodyne instrumentation amplifier 272B includes a quadrature phase (Q) signal path with a third modulator 328, an adder 329, an amplifier 330, a quadrature frequency offset (δ) 331, a fourth modulator 332, a lowpass filter 333, and a squaring unit 334. Adder 329 represents addition of noise. Adder 329 models the noise from non-ideal transistor characteristics.

Superheterodyne instrumentation amplifier 272B receives a physiological signal ($V_{in}$) associated with a patient from one or more sensing elements. The in-phase (I) signal path modulates the signal from baseband at the carrier frequency ($f_c$), permits addition of a noise signal to the modulated signal, and amplifies the noisy modulated signal. In-phase frequency offset 323 may be tuned such that it is substantially equivalent to a center frequency of a selected frequency band. For the alpha band (5 to 15 Hz), for example, the offset 323 may be approximately 10 Hz. In this example, if the modulation carrier frequency $f_c$ applied by modulator 320 is 4000 Hz, then the demodulation frequency $f_c \pm \delta$ may be 3990 Hz or 4010 Hz.

Second modulator 324 modulates the noisy amplified signal at a frequency ($f_c \pm \delta$) offset from the carrier frequency $f_c$ by the offset amount δ. In this way, the amplified signal in the selected frequency band may be demodulated directly to baseband and the noise signal may be modulated up to the second frequency $f_c \pm \delta$. The selected frequency band of the physiological signal is then substantially centered at baseband, e.g., DC. For the alpha band (5 to 15 Hz), for example, the center frequency of 10 Hz is centered at 0 Hz at baseband. Lowpass filter 325 filters the majority of the modulated noise signal out of the demodulated signal and outputs a low-noise physiological signal. The low-noise physiological signal may then be squared with squaring unit 326 and input to adder 336. In some cases, squaring unit 326 may comprise a self-cascoded Gilbert mixer. The output of squaring unit 126 represents the spectral power of the in-phase signal.

In a similar fashion, the quadrature (Q) signal path modulates the signal from baseband at the carrier frequency ($f_c$). However, the carrier frequency applied by modulator 328 in the Q signal path is 90 degrees out of phase with the carrier frequency applied by modulator 320 in the I signal path. The Q signal path permits addition of a noise signal to the modulated signal, as represented by adder 329, and amplifies the noisy modulated signal via amplifier 330. Again, quadrature offset frequency (δ) 331 may be tuned such it is approximately equal to the center frequency of the selected frequency band. As a result, the demodulation frequency applied to demodulator 332 is ($f_c \pm \delta$). In the quadrature signal path, however, an additional phase shift of 90 degrees is added to the demodulation frequency for demodulator 332. Hence, the demodulation frequency for demodulator 332, like demodulator 324, is $f_c \pm \delta$. However, the demodulation frequency for demodulator 332 is phase shifted by 90 degrees relative to the demodulation frequency for demodulator 324 of the in-phase signal path.

Fourth modulator 332 modulates the noisy amplified signal at the quadrature frequency 331 from the carrier frequency. In this way, the amplified signal in the selected frequency band is demodulated directly to baseband and the noise signal is modulated at the demodulation frequency $f_c \pm \delta$. Lowpass filter 333 filters the majority of the modulated noise signal out of the demodulated signal and outputs a low-noise physiological signal. The low-noise physiological signal may then be squared and input to adder 336. Like squaring unit 326, squaring unit 334 may comprise a self-cascoded Gilbert mixer. The output of squaring unit 334 represents the spectral power of the quadrature signal.

Adder 336 combines the signals output from squaring unit 326 in the in-phase signal path and squaring unit 334 in the quadrature signal path. The output of adder 336 may be input to a lowpass filter 337 that generates a low-noise, phase-insensitive output signal ($V_{out}$). As described above, the signal may be input to signal analysis unit 273 from FIG. 22. As described above, signal analysis unit 273 may extract the signal in the selected frequency band positioned at baseband, measure power of the extracted signal, and compare the measured power to a baseline power threshold of the selected frequency band to determine whether to trigger patient therapy. Alternatively, signal analysis unit 273 may analyze other characteristics of the signal. The signal Vout may be applied to the signal analysis unit 273 as an analog signal. Alternatively, an analog-to-digital converter (ADC) may be provided to convert the signal Vout to a digital signal for application to signal analysis unit 273. Hence, signal analysis unit 273 may include one or more analog components, one or more digital components, or a combination of analog and digital components.

Figure 26:
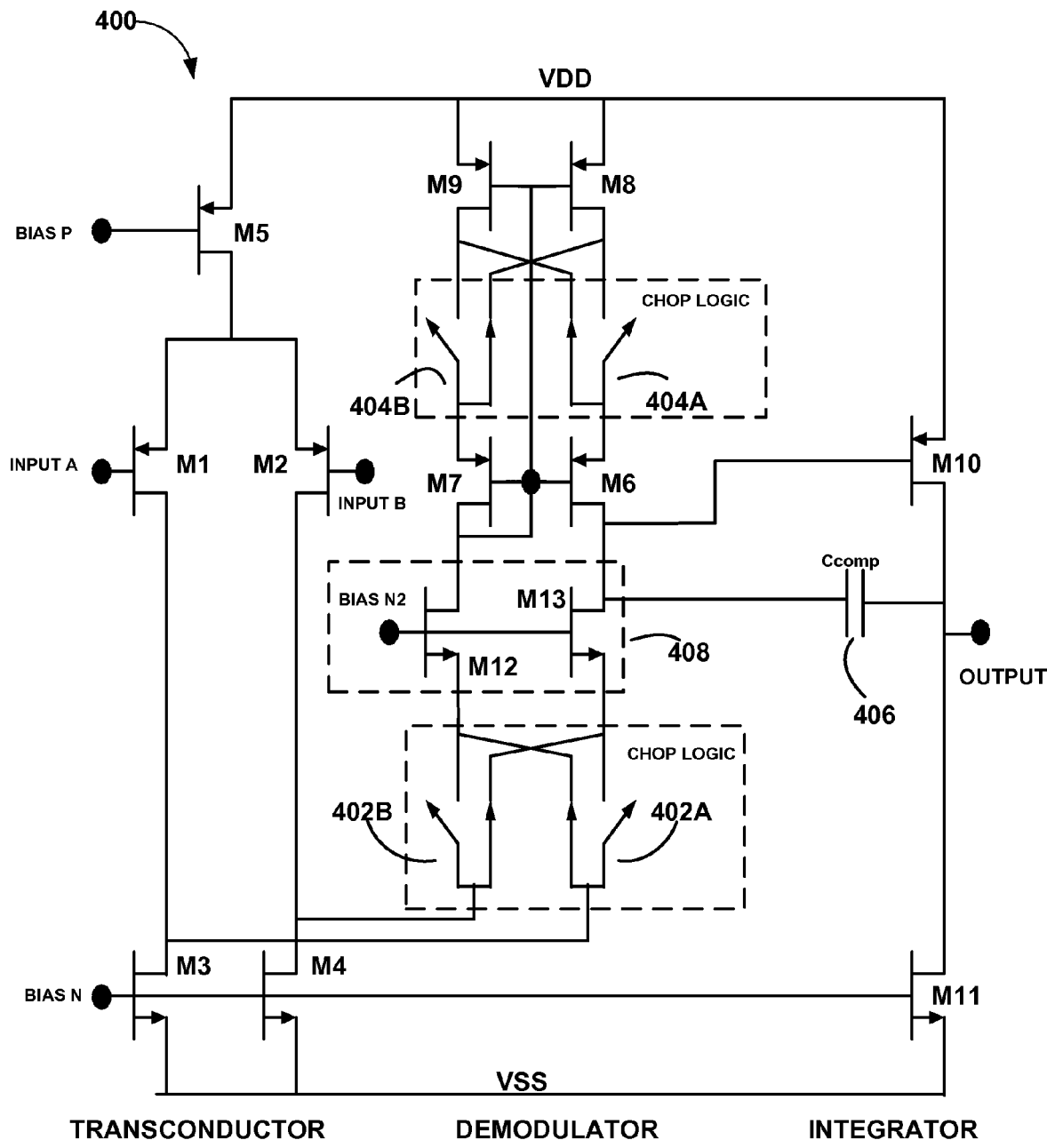
FIG. 26 is a circuit diagram illustrating an example chopper-stabilized mixer amplifier that may be used within the frequency selective signal monitor of FIG. 22.

FIG. 26 is a circuit diagram illustrating an example mixer amplifier circuit 400 for use in superheterodyne instrumentation amplifier 272 of FIG. 22. For example, circuit 400 represents an example of amplifier 286, demodulator 288 and integrator 289 in FIG. 22. Although the example of FIG. 26 illustrates a differential input, circuit 400 may be constructed with a single-ended input. Accordingly, circuit 400 of FIG. 26 is provided for purposes of illustration, without limitation as to other examples. In FIG. 26, VDD and VSS indicate power and ground potentials, respectively.

Mixer amplifier circuit 400 amplifies a noisy modulated input signal to produce an amplified signal and demodulates the amplified signal. Mixer amplifier circuit 400 also substantially eliminates noise from the demodulated signal to generate the output signal. In the example of FIG. 26, mixer amplifier circuit 400 is a modified folded-cascode amplifier with switching at low impedance nodes. The modified folded-cascode architecture allows currents to be partitioned to maximize noise efficiency. In general, the folded cascode architecture is modified in FIG. 26 by adding two sets of switches. One set of switches is illustrated in FIG. 26 as switches 402A and 402B (collectively referred to as "switches 402") and the other set of switches includes switches 404A and 404B (collectively referred to as "switches 404").

Switches 402 are driven by chop logic to support the chopping of the amplified signal for demodulation at the chop frequency. In particular, switches 402 demodulate the amplified signal and modulate front-end offsets and 1/f noise. Switches 404 are embedded within a self-biased cascode mirror formed by transistors M6, M7, M8 and M9, and are driven by chop logic to up-modulate the low frequency errors from transistors M8 and M9. Low frequency errors in transistors M6 and M7 are attenuated by source degeneration from transistors M8 and M9. The output of mixer amplifier circuit 400 is at baseband, allowing an integrator formed by transistor M10 and capacitor 406 (Ccomp) to stabilize a feedback path (not shown in FIG. 26) between the output and input and filter modulated offsets.

In the example of FIG. 26, mixer amplifier circuit 400 has three main blocks: a transconductor, a demodulator, and an integrator. The core is similar to a folded cascode. In the transconductor section, transistor M5 is a current source for the differential pair of input transistors M1 and M2. In some examples, transistor M5 may pass approximately 800 nA, which is split between transistors M1 and M2, e.g., 400 nA each. Transistors M1 and M2 are the inputs to amplifier 286. Small voltage differences steer differential current into the drains of transistors M1 and M2 in a typical differential pair way. Transistors M3 and M4 serve as low side current sinks, and may each sink roughly 500 nA, which is a fixed, generally nonvarying current. Transistors M1, M2, M3, M4 and M5 together form a differential transconductor.

In this example, approximately 100 nA of current is pulled through each leg of the demodulator section. The AC current at the chop frequency from transistors M1 and M2 also flows through the legs of the demodulator. Switches 402 alternate the current back and forth between the legs of the demodulator to demodulate the measurement signal back to baseband, while the offsets from the transconductor are up-modulated to the chopper frequency. As discussed previously, transistors M6, M7, M8 and M9 form a self-biased cascode mirror, and make the signal single-ended before passing into the output integrator formed by transistor M10 and capacitor 406 (Ccomp). Switches 404 placed within the cascode (M6-M9) upmodulate the low frequency errors from transistors M8 and M9, while the low frequency errors of transistor M6 and transistor M7 are suppressed by the source degeneration they see from transistors M8 and M9. Source degeneration also keeps errors from Bias N2 transistors 408 suppressed. Bias N2 transistors M12 and M13 form a common gate amplifier that presents a low impedance to the chopper switching and passes the signal current to transistors M6 and M7 with immunity to the voltage on the drains.

The output DC signal current and the upmodulated error current pass to the integrator, which is formed by transistor M10, capacitor 406, and the bottom NFET current source transistor M1. Again, this integrator serves to both stabilize the feedback path and filter out the upmodulated error sources. The bias for transistor M10 may be approximately 100 nA, and is scaled compared to transistor M8. The bias for lowside NFET M11 may also be approximately 100 nA (sink). As a result, the integrator is balanced with no signal. If more current drive is desired, current in the integration tail can be increased appropriately using standard integrate circuit design techniques. Various transistors in the example of FIG. 26 may be field effect transistors (FETs), and more particularly CMOS transistors.

Figure 27:
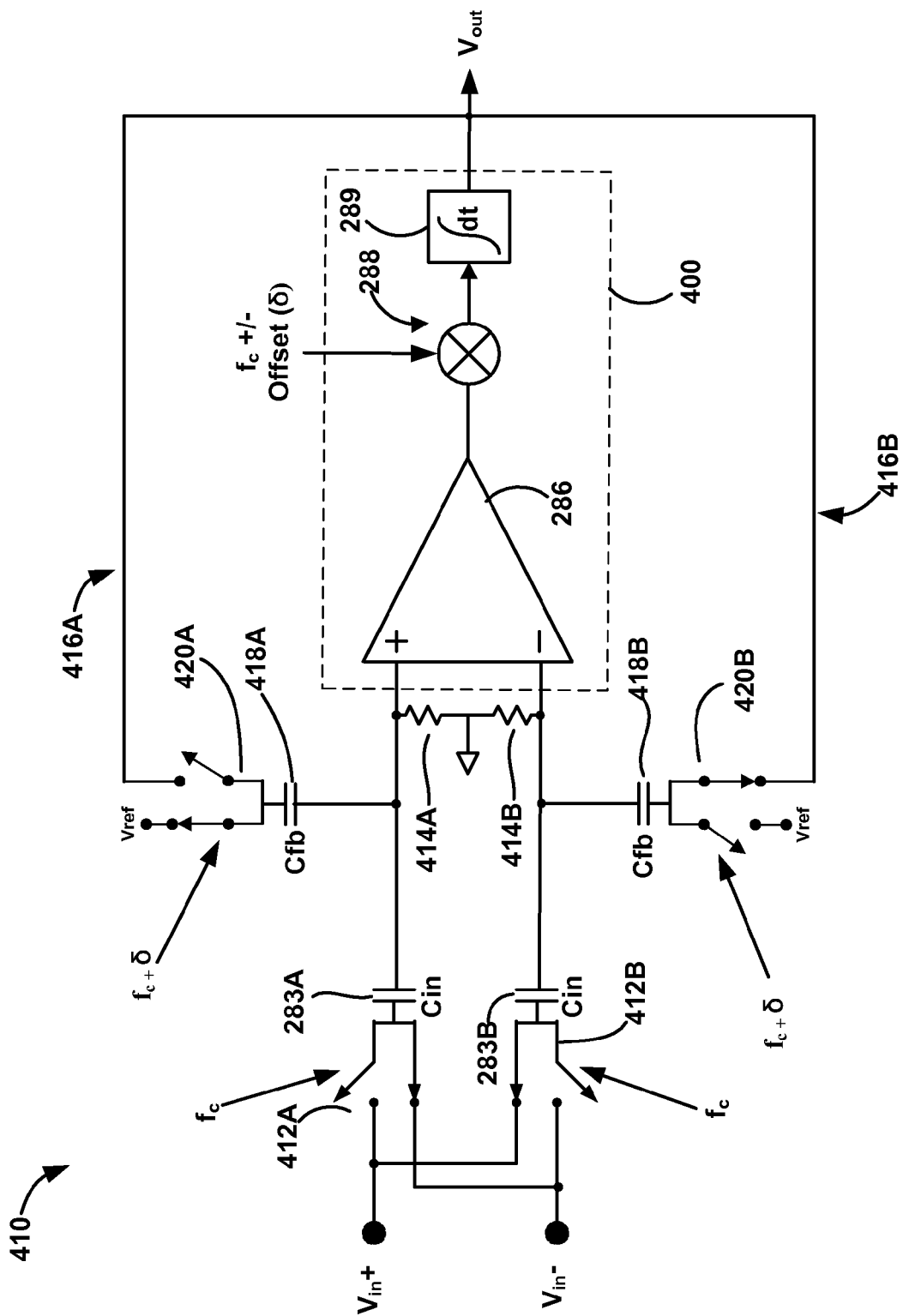
FIG. 27 is a circuit diagram illustrating an example chopper-stabilized, superheterodyne instrumentation amplifier with differential inputs.

FIG. 27 is a circuit diagram illustrating an instrumentation amplifier 410 with differential inputs $V_{in}+$ and $V_{in}-$. Instrumentation amplifier 410 is an example superheterodyne instrumentation amplifier 272 previously described in this disclosure with reference to FIG. 22. FIG. 27 uses several reference numerals from FIG. 22 to refer to like components. However, the optional high pass filter feedback path comprising components 292, 293 and 294 is omitted from the example of FIG. 27. In general, instrumentation amplifier 410 may be constructed as a single-ended or differential amplifier. The example of FIG. 27 illustrates example circuitry for implementing a differential amplifier. The circuitry of FIG. 27 may be configured for use in each of the I and Q signal paths of FIG. 25.

In the example of FIG. 27, instrumentation amplifier 410 includes an interface to one or more sensing elements that produce a differential input signal providing voltage signals $V_{in}+$, $V_{in}-$. The differential input signal may be provided by a sensor comprising any of a variety of sensing elements, such as a set of one or more electrodes, an accelerometer, a pressure sensor, a force sensor, a gyroscope, a humidity sensor, a chemical sensor, or the like. For brain sensing, the differential signal $V_{in}+$, $V_{in}-$ may be, for example, an EEG or EcoG signal.

The differential input voltage signals are connected to respective capacitors 283A and 283B (collectively referred to as "capacitors 283") through switches 412A and 412B, respectively. Switches 412A and 412B may collectively form modulator 282 of FIG. 22. Switches 412A, 412B are driven by a clock signal provided by a system clock (not shown) at the carrier frequency $f_c$. Switches 412A, 412B may be cross-coupled to each other, as shown in FIG. 27, to reject common-mode signals. Capacitors 283 are coupled at one end to a corresponding one of switches 412A, 412B and to a corresponding input of amplifier 286 at the other end. In particular, capacitor 283A is coupled to the positive input of amplifier 286, and capacitor 283B is coupled to the negative input of amplifier 286, providing a differential input. Amplifier 286, modulator 288 and integrator 289 together may form a mixer amplifier, which may be constructed similar to mixer amplifier 400 of FIG. 26.

In FIG. 27, switches 412A, 412B and capacitors 283A, 283B form a front end of instrumentation amplifier 410. In particular, the front end may operate as a continuous time switched capacitor network. Switches 412A, 412B toggle between an open state and a closed state in which inputs signals $V_{in}+$, $V_{in}-$ are coupled to capacitors 283A, 283B at a clock frequency $f_c$ to modulate (chop) the input signal to the carrier (clock) frequency. As mentioned previously, the input signal may be a low frequency signal within a range of approximately 0 Hz to approximately 1000 Hz and, more particularly, approximately 0 Hz to 500 Hz, and still more particularly less than or equal to approximately 100 Hz. The carrier frequency may be within a range of approximately 4 kHz to approximately 10 kHz. Hence, the low frequency signal is chopped to the higher chop frequency band.

Switches 412A, 412B toggle in-phase with one another to provide a differential input signal to amplifier 286. During one phase of the clock signal $f_c$, switch 412A connects Vin+ to capacitor 283A and switch 412B connects Vin− to capacitor 283B. During another phase, switches 412A, 412B change state such that switch 412A decouples Vin+ from capacitor 283A and switch 412B decouples Vin− from capacitor 283B. Switches 412A, 412B synchronously alternate between the first and second phases to modulate the differential voltage at the carrier frequency. The resulting chopped differential signal is applied across capacitors 283A, 283B, which couple the differential signal across the positive and negative inputs of amplifier 286.

Resistors 414A and 414B (collectively referred to as "resistors 414") may be included to provide a DC conduction path that controls the voltage bias at the input of amplifier 286. In other words, resistors 414 may be selected to provide an equivalent resistance that is used to keep the bias impedance high. Resistors 414 may, for example, be selected to provide a 5 GΩ equivalent resistor, but the absolute size of the equivalent resistor is not critical to the performance of instrumentation amplifier 410. In general, increasing the impedance improves the noise performance and rejection of harmonics, but extends the recovery time from an overload. To provide a frame of reference, a 5 GΩ equivalent resistor results in a referred-to-input (RTI) noise of approximately 20 nV/rt Hz with an input capacitance (Cin) of approximately 25 pF. In light of this, a stronger motivation for keeping the impedance high is the rejection of high frequency harmonics which can alias into the signal chain due to settling at the input nodes of amplifier 286 during each half of a clock cycle.

Resistors 414 are merely exemplary and serve to illustrate one of many different biasing schemes for controlling the signal input to amplifier 286. In fact, the biasing scheme is flexible because the absolute value of the resulting equivalent resistance is not critical. In general, the time constant of resistor 414 and input capacitor 283 may be selected to be approximately 100 times longer than the reciprocal of the chopping frequency.

Amplifier 286 may produce noise and offset in the differential signal applied to its inputs. For this reason, the differential input signal is chopped via switches 412A, 412B and capacitors 283A, 283B to place the signal of interest in a different frequency band from the noise and offset. Then, instrumentation amplifier 410 chops the amplified signal at modulator 88 a second time to demodulate the signal of interest down to baseband while modulating the noise and offset up to the chop frequency band. In this manner, instrumentation amplifier 410 maintains substantial separation between the noise and offset and the signal of interest.

Modulator 288 may support direct downconversion of the selected frequency band using a superheterodyne process. In particular, modulator 288 may demodulate the output of amplifier 86 at a frequency equal to the carrier frequency $f_c$ used by switches 412A, 412B plus or minus an offset δ that is substantially equal to the center frequency of the selected frequency band. In other words, modulator 88 demodulates the amplified signal at a frequency of $f_c\pm\delta$. Integrator 289 may be provided to integrate the output of modulator 288 to produce output signal Vout. Amplifier 286 and differential feedback path branches 416A, 416B process the noisy modulated input signal to achieve a stable measurement of the low frequency input signal output while operating at low power.

Operating at low power tends to limit the bandwidth of amplifier 286 and creates distortion (ripple) in the output signal. Amplifier 286, modulator 288, integrator 289 and feedback paths 416A, 416B may substantially eliminate dynamic limitations of chopper stabilization through a combination of chopping at low-impedance nodes and AC feedback, respectively.

In FIG. 27, amplifier 286, modulator 288 and integrator 289 are represented with appropriate circuit symbols in the interest of simplicity. However, it should be understood that such components may be implemented in accordance with the circuit diagram of mixer amplifier circuit 400 provided in FIG. 26. Instrumentation amplifier 410 may provide synchronous demodulation with respect to the input signal and substantially eliminate 1/f noise, popcorn noise, and offset from the signal to output a signal that is an amplified representation of the differential voltage Vin+, Vin−.

Without the negative feedback provided by feedback path 416A, 416B, the output of amplifier 286, modulator 288 and integrator 289 could include spikes superimposed on the desired signal because of the limited bandwidth of the amplifier at low power. However, the negative feedback provided by feedback path 416A, 416B suppresses these spikes so that the output of instrumentation amplifier 410 in steady state is an amplified representation of the differential voltage produced across the inputs of amplifier 286 with very little noise.

Feedback paths 416A, 216B, as shown in FIG. 27, include two feedback path branches that provide a differential-to-single ended interface. Amplifier 286, modulator 288 and integrator 289 may be referred to collectively as a mixer amplifier. The top feedback path branch 416A modulates the output of this mixer amplifier to provide negative feedback to the positive input terminal of amplifier 286. The top feedback path branch 416A includes capacitor 418A and switch 420A. Similarly, the bottom feedback path branch 416B includes capacitor 418B and switch 420B that modulate the output of the mixer amplifier to provide negative feedback to the negative input terminal of the mixer amplifier. Capacitors 418A, 418B are connected at one end to switches 420A, 420B, respectively, and at the other end to the positive and negative input terminals of the mixer amplifier, respectively. Capacitors 418A, 418B may correspond to capacitor 291 in FIG. 22. Likewise, switches 420A, 420B may correspond to modulator 290 of FIG. 22.

Switches 420A and 420B toggle between a reference voltage (Vref) and the output of the mixer amplifier 400 to place a charge on capacitors 418A and 418B, respectively. The reference voltage may be, for example, a mid-rail voltage between a maximum rail voltage of amplifier 286 and ground. For example, if the amplifier circuit is powered with a source of 0 to 2 volts, then the mid-rail Vref voltage may be on the order of 1 volt. Switches 420A and 420B should be 180 degrees out of phase with each other to ensure that a negative feedback path exists during each half of the clock cycle. One of switches 420A, 420B should also be synchronized with the mixer amplifier 400 so that the negative feedback suppresses the amplitude of the input signal to the mixer amplifier to keep the signal change small in steady state. Hence, a first one of the switches 420A, 420B may modulate at a frequency of $f_c \pm \delta$, while a second switch 420A, 420B modulates at a frequency of $f_c \pm \delta$, but 180 degrees out of phase with the first switch. By keeping the signal change small and switching at low impedance nodes of the mixer amplifier, e.g., as shown in the circuit diagram of FIG. 26, the only significant voltage transitions occur at switching nodes. Consequently, glitching (ripples) is substantially eliminated or reduced at the output of the mixer amplifier.

Switches 412 and 420, as well as the switches at low impedance nodes of the mixer amplifier, may be CMOS SPDT switches. CMOS switches provide fast switching dynamics that enables switching to be viewed as a continuous process. The transfer function of instrumentation amplifier 210 may be defined by the transfer function provided in equation (1) below, where Vout is the voltage of the output of mixer amplifier 400, Cin is the capacitance of input capacitors 283, ΔVin is the differential voltage at the inputs to amplifier 286, Cfb is the capacitance of feedback capacitors 418A, 418B, and Vref is the reference voltage that switches 420A, 420B mix with the output of mixer amplifier 400.

$$Vout = Cin(\Delta Vin)/Cfb + Vref \qquad (1)$$

From equation (1), it is clear that the gain of instrumentation amplifier 410 is set by the ratio of input capacitors Cin and feedback capacitors Cfb, i.e., capacitors 283 and capacitors 418. The ratio of Cin/Cfb may be selected to be on the order of 100. Capacitors 418 may be poly-poly, on-chip capacitors or other types of MOS capacitors and should be well matched, i.e., symmetrical.

Although not shown in FIG. 27, instrumentation amplifier 410 may include shunt feedback paths for auto-zeroing amplifier 410. The shunt feedback paths may be used to quickly reset amplifier 410. An emergency recharge switch also may be provided to shunt the biasing node to help reset the amplifier quickly. The function of input capacitors 283 is to up-modulate the low-frequency differential voltage and reject common-mode signals. As discussed above, to achieve up-modulation, the differential inputs are connected to sensing capacitors 283A, 283B through SPDT switches 412A, 412B, respectively. The phasing of the switches provides for a differential input to amplifier 286. These switches 412A, 412B operate at the clock frequency, e.g., 4 kHz. Because capacitors 283A, 283B toggle between the two inputs, the differential voltage is up-modulated to the carrier frequency while the low-frequency common-mode signals are suppressed by a zero in the charge transfer function. The rejection of higher-bandwidth common signals relies on this differential architecture and good matching of the capacitors.

Blanking circuitry may be provided in some examples for applications in which measurements are taken in conjunction with stimulation pulses delivered by a cardiac pacemaker, cardiac defibrillator, or neurostimulator. Such blanking circuitry may be added between the inputs of amplifier 286 and coupling capacitors 283A, 283B to ensure that the input signal settles before reconnecting amplifier 86 to the input signal. For example, the blanking circuitry may be a blanking multiplexer (MUX) that selectively couples and de-couples amplifier 286 from the input signal. This blanking circuitry may selectively decouple the amplifier 286 from the differential input signal and selectively disable the first and second modulators, i.e., switches 412, 420, e.g., during delivery of a stimulation pulse.

A blanking MUX is optional but may be desirable. The clocks driving switches 412, 420 to function as modulators cannot be simply shut off because the residual offset voltage on the mixer amplifier would saturate the amplifier in a few milliseconds. For this reason, a blanking MUX may be provided to decouple amplifier 86 from the input signal for a specified period of time during and following application of a stimulation by a cardiac pacemaker or defibrillator, or by a neurostimulator.

To achieve suitable blanking, the input and feedback switches 412, 420 should be disabled while the mixer amplifier continues to demodulate the input signal. This holds the state of integrator 289 within the mixer amplifier because the modulated signal is not present at the inputs of the integrator, while the demodulator continues to chop the DC offsets. Accordingly, a blanking MUX may further include circuitry or be associated with circuitry configured to selectively disable switches 412, 420 during a blanking interval. Post blanking, the mixer amplifier may require additional time to resettle because some perturbations may remain. Thus, the total blanking time includes time for demodulating the input signal while the input switches 412, 420 are disabled and time for settling of any remaining perturbations. An example blanking time following application of a stimulation pulse may be approximately 8 ms with 5 ms for the mixer amplifier and 3 ms for the AC coupling components.

Examples of various additional chopper amplifier circuits that may be suitable for or adapted to the techniques, circuits and devices of this disclosure are described in U.S. patent application Ser. No. 11/700,404, filed Jan. 31, 2007, to Timothy J. Denison, entitled "Chopper Stabilized Instrumentation Amplifier," the entire content of which is incorporated herein by reference.

Various examples of systems and techniques for controlling a therapy delivery device have been described. These and other examples are within the scope of the following claims. While some therapy systems and methods have primarily been described with reference to determining whether patient 12 is in a movement state based on EEG signals, in other examples, other neural based bioelectrical signals may be useful. Other useful neural-based bioelectrical signals include electrical signals from regions of brain 20 deeper than the signals reflected in the EEG, such as an ECoG signal that measures electrical signals on a surface of brain 20. As other examples of bioelectrical signals of brain 20 that may be used to detect a movement state of patient 12, electrodes placed within the motor cortex or other regions of brain 20 may detect field potentials within the particular region of the brain, and the field potential may be indicative of a movement state. The particular bioelectrical signal that is indicative of the movement state may be determined during a trial stage, as described above with respect to the EEG signal.

In addition, a processor may employ any suitable signal processing technique to determine whether the bioelectrical signal indicates the movement state. For example, as described above with respect to EEG signals, an ECoG or field potential signal may be analyzed for a relationship between a voltage or amplitude of the signal and a threshold value, temporal correlation or frequency correlation with a template signal, power levels within one or more frequency bands, ratios of power levels within two or more frequency bands, or combinations thereof.

While the above techniques for analyzing a brain signal within the DLPF cortex 132 (FIG. 15) were described primarily with reference to IMD 134 (FIG. 15), in other examples, a processor within another device, implanted or external, may determine whether a brain signal within the DLPF cortex 132 indicates prospective movement. In addition, while signal processing is described primarily with reference to processor 72 of IMD 134, in other examples, the signal processor for processing the electrical activity sensed within DLPF cortex 132 may be integrated with sensing module 136 of IMD 134, external sensing device 14 (FIG. 1A) or any other suitable device.

The invention claimed is:

1. A method comprising:
monitoring a bioelectrical brain signal from a brain of a patient;
determining the brain signal indicates the patient is in a movement state, wherein the brain signal that indicates the patient is in the movement state results from a volitional patient movement or volitional intention to move;
at a first time, controlling delivery of therapy to the patient based on determining the brain signal indicates the patient is in the movement state;
at a second time following the first time, determining whether the patient is in the movement state; and
controlling the delivery of the therapy to the patient based on whether the patient is in the movement state at the second time following the first time.

2. The method of claim 1, wherein the bioelectrical brain signal comprises at least one of an electroencephalogram (EEG) signal, an electrocorticogram (ECoG) signal, a signal generated from measured field potentials within one or more regions of the brain or action potentials from single cells within the brain.

3. The method of claim 2, wherein determining whether the electroencephalogram (EEG) signal indicates the patient is in a movement state comprises determining whether a mu rhythm of the EEG signal indicate the patient in the movement state.

4. The method of claim 1, wherein monitoring the bioelectrical brain signal comprises monitoring a bioelectrical brain signal within a dorsal-lateral prefrontal cortex of the patient.

5. The method of claim 1, wherein determining whether the bioelectrical brain signal indicates the patient is in the movement state comprises evaluating one or more frequency characteristics of the bioelectrical brain signal.

6. The method of claim 5, wherein the frequency characteristics comprise signal power levels within at least one of an alpha frequency band comprising a range of about 5 hertz to about 15 hertz or a high gamma frequency band comprising a range of about 100 hertz to about 200 hertz.

7. The method of claim 1, wherein the movement state comprises at least one of an intention to initiate movement, initiation of movement, an attempt to initiate movement or actual movement.

8. The method of claim 1, wherein controlling delivery of therapy at the first time comprises initiating delivery of the therapy.

9. The method of claim 1, wherein controlling delivery of therapy at the first time comprises adjusting a therapy parameter value.

10. The method of claim 1, wherein controlling delivery of therapy at the first time comprises controlling the delivery of an external cue to the patient.

11. The method of claim 1, wherein controlling delivery of the therapy at the first time comprises controlling delivery of a sensory cue to the patient.

12. The method of claim 1, wherein controlling the delivery of the therapy to the patient based on whether the patient is in the movement state at the second time following the first time comprises modifying a therapy parameter value.

13. The method of claim 1, wherein controlling delivery of the therapy at the first time comprises controlling the delivery of the therapy to the patient according to a first therapy program, and wherein controlling the delivery of the therapy to the patient based on whether the patient is in the movement state at the second time following the first time comprises controlling the delivery of therapy to the patient according to the first therapy program.

14. The method of claim 1, further comprising stopping the delivery of therapy after a predetermined period of time.

15. The method of claim 1, further comprising:
determining whether the patient is no longer in the movement state; and
stopping delivery of therapy if the patient is no longer in the movement state.

16. The method of claim 15, wherein determining whether the patient is no longer in the movement state comprises determining whether the brain signal indicates the patient is in a rest state.

17. The method of claim 15, wherein determining whether the patient is no longer in the movement state comprises receiving input from a motion sensor.

18. The method of claim 1, wherein determining whether the patient is in the movement state at the second time comprises, at the second time, determining whether the brain signal indicates the patient is in a movement state.

19. The method of claim 1, wherein determining whether the patient is in the movement state at the second time comprises receiving input from a motion sensor and determining whether the patient is in the movement state based on the input from the motion sensor.

20. The method of claim 1, wherein determining whether the patient is in the movement state at the second time comprises determining whether the patient is in the movement state based on a signal other than the brain signal.

21. A system comprising:
a sensing module that monitors an bioelectrical brain signal of a patient; and
a processor that determines the bioelectrical brain signal indicates the patient is in a movement state and, at a first time, controls delivery of therapy to the patient based on determining the bioelectrical brain signal indicates the patient is in a movement state, wherein the processor, at a second time following the first time, determines whether the patient is in the movement state and controls the delivery of the therapy to the patient based on whether the patient is in the movement state at the second time following the first time, and wherein the brain signal that indicates the patient is in the movement state results from a volitional patient movement or volitional intention to move.

22. The system of claim 21, wherein the bioelectrical brain signal comprises at least one of an electroencephalogram (EEG) signal, an electrocorticogram (ECoG) signal, a signal generated from measured field potentials within one or more regions of the brain or action potentials from single cells within the brain.

23. The system of claim 21, wherein the sensing module monitors the bioelectrical brain signal within a dorsal-lateral prefrontal cortex of a brain of the patient.

24. The system of claim 21, wherein the processor determines whether the bioelectrical brain signal indicates the patient is in a movement state based on one or more frequency characteristics of the bioelectrical brain signal.

25. The system of claim 21, wherein the processor controls the delivery of therapy to the patient at the first time if the bioelectrical brain signal indicates the patient is in the movement state by at least initiating the delivery of the therapy.

26. The system of claim 21, wherein the processor controls the delivery of therapy to the patient at the first time if the bioelectrical brain signal indicates the patient is in the movement state by at least adjusting a therapy parameter value of the therapy.

27. The system of claim 21, wherein the movement state comprises at least one of intending to initiate movement, initiating movement, attempting to initiate movement or undergoing movement.

28. The system of claim 21, further comprising a therapy delivery device, wherein the processor transmits a control signal to the therapy delivery device to control the delivery of the therapy to the patient by the therapy delivery device.

29. The system of claim 21, further comprising a device configured to delivery a sensory cue to the patient, wherein the therapy comprises the sensory cue.

30. The system of claim 21, wherein the processor controls the delivery of the therapy to the patient based on whether the patient is in the movement state at the second time following the first time by at least modifying a therapy parameter value.

31. The system of claim 21, wherein the processor determines whether the patient is no longer in the movement state and stops delivery of the therapy if the bioelectrical brain signal indicates the patient is no longer in the movement state.

32. The system of claim 21, further comprising a motion sensor, wherein the processor determines whether the patient is in the movement state at the second time based on input from the motion sensor.

33. The system of claim 21, wherein the processor determines whether the patient is in the movement state at the second time based on a signal other than the brain signal.

34. A non-transitory computer-readable medium comprising instructions that cause a processor to:
receive a bioelectrical brain signal;
determine the bioelectrical brain signal indicates the patient is in a movement state, wherein the brain signal that indicates the patient is in the movement state results from a volitional patient movement or volitional intention to move;
at a first time, control operation of a therapy device based on determining the bioelectrical brain signal indicates the patient is in a movement state;
at a second time following the first time, determine whether the patient is in the movement state; and
control the operation of the therapy device based on whether the patient is in the movement state at the second time following the first time.

* * * * *